(12) United States Patent
Moe et al.

(10) Patent No.: US 7,595,307 B2
(45) Date of Patent: Sep. 29, 2009

(54) POLYSACCHARIDE DERIVATIVES AND USES IN INDUCTION OF AN IMMUNE RESPONSE

(75) Inventors: Gregory R. Moe, Alameda, CA (US); Dan M. Granoff, Berkeley, CA (US)

(73) Assignee: Children's Hospital and Research Center at Oakland, Oakland, CA (US)

( * ) Notice: Subject to any disclaimer, the term of this patent is extended or adjusted under 35 U.S.C. 154(b) by 239 days.

(21) Appl. No.: 11/166,781

(22) Filed: Jun. 23, 2005

(65) Prior Publication Data
US 2007/0010482 A1    Jan. 11, 2007

Related U.S. Application Data

(60) Provisional application No. 60/582,672, filed on Jun. 23, 2004.

(51) Int. Cl.
A61K 31/715    (2006.01)
C07H 1/00    (2006.01)
C07H 5/04    (2006.01)
C07H 5/05    (2006.01)

(52) U.S. Cl. .......................... 514/54; 514/55; 536/123.1

(58) Field of Classification Search .................. None
See application file for complete search history.

(56) References Cited

U.S. PATENT DOCUMENTS

| | | | |
|---|---|---|---|
| 4,727,136 A | | 2/1988 | Jennings et al. |
| 5,811,102 A | | 9/1998 | Jennings et al. |
| 5,846,951 A | * | 12/1998 | Gregoriadis ................. 514/54 |
| 5,969,130 A | | 10/1999 | Jennings et al. |
| 6,030,619 A | | 2/2000 | Granoff et al. |
| 6,048,527 A | | 4/2000 | Granoff et al. |
| 6,350,449 B1 | | 2/2002 | Jennings et al. |
| 6,638,513 B2 | | 10/2003 | Seid |
| 2002/0034518 A1 | | 3/2002 | Seid |

FOREIGN PATENT DOCUMENTS

| | | |
|---|---|---|
| EP | 0504 202 B1 | 3/1995 |
| WO | WO99/10372 | 3/1999 |
| WO | WO 01/09298 | 2/2001 |
| WO | WO 02/09744 | 2/2002 |
| WO | WO 2006/002402 | 1/2006 |

OTHER PUBLICATIONS

Jennings et al. 1986 J Immunol 137:1708-1713.*
Singh et al. 1999 Nature Biotechnology 17:1075-1081.*
Chapman et al. Sequential Immunization of Melanoma Patients with GD3 Ganglioside Vaccine and Anti-Idiotypic Monoclonal Antibody that Mimics GD3 Ganglioside. Clinical Cancer Research, 2004, vol. 10, 4717-4723.
Chapman et al. Induction of IgG Antibodies Against $G_{D3}$ Ganglioside in Rabbits by an Anti-idiotypic Monocloncal Antibody. Department of Medicine and the Immunology Program, 1991, 88:186-192.

Moe et al. Epitopes Recognized by a Nonautoreactive Murine Anti-N-Propionyl Meningococcal Group B Polysaccharide Monoclonal Antibody (2005) Infect Immun 73, 2123-8.
Moe et al. *GenBank Accession Nos. DQ113491* submitted Jun. 30, 2005; ROD Mar. 8, 2006.
Moe et al. *GenBank Accession Nos. DQ113492* submitted Jun. 30, 2005; ROD Mar. 8, 2006.
Ritter et al. Antibody Response to Immunization with Ganglioside GD3 and GD3 Congeners (Lactones, Amide and Ganliosidol) in Patients with Malignant Melanoma. Int. J. Cancer, (1991) 48, 379-385.
Ritter et al. Analysis of the Antibody Response to Immunization with Purified *O-Acetyl* GD3 Gangliosides in Patients with Malignant Melanoma. Int. J. Cancer, (1995) 62, 668-672.
Finne et al. "Occurrence of alpha 2-8 linked polysialosyl units in a neural cell adhesion molecule", 1983, Biochem Biophys Res Commun 112:482.
Frosch et al. "NZB mouse system for production of monoclonal antibodies to weak bacterial antigens: isolation of an IgG antibody to the polysaccharide capsules of *Escherichia coli* K1 and group B meningococci", 1985 Proc Natl Acad Sci U S A 82:1194.
Griffiss, J. M. 1995. Mechanisms of host immunity, p. 35-70. In K. Cartwright (ed.), Meningococcal disease. John Wiley & Sons, Chichester, England.
Granoff et al., "Bactericidal monoclonal antibodies that define unique meningococcal B polysaccharide epitopes that do not cross-react with human polysialic acid", 1998, J. Immunol; 160: 5028-5036.
Hurpin et al. "Bactericidal activity of two $IgG_{2a}$ murine monoclonal antibodies with distinct fine specificities for group B *Neisseria meningitidis* capsular polysaccharide", 1992 Hybridoma 11:677.
Hayrinen et al. "Antibodies to polysialic acid and its N-propyl derivative: binding properties and interaction with human embryonal brain glycopeptides", 1995, J Infect Dis 171:1481.
Jones D. Epidemiology of meningococcal disease in Europe and the USA. In: Cartwright K, ed. Meningococcal disease. New York: John Wiley & Sons, 1995;147-157.
Jennings et al., "Immunochemistry of groups A, B, and C meningococcal polysaccharide-tetanus toxoid conjugates", 1981, J Immunol 127:1011.
Mandrell et al. "Measurement of antibodies to meningococcal group B polysaccharide: low avidity binding and equilibrium binding constants", 1982 J Immunol 129:2172.

(Continued)

Primary Examiner—Shaojia Anna Jiang
Assistant Examiner—Eric S Olson
(74) Attorney, Agent, or Firm—Carol L. Francis; Bozicevic, Field & Francis, LLP

(57) ABSTRACT

The present invention generally provides compositions comprising a polysaccharide derivative, and methods of their preparation and use for the prevention or treatment of diseases caused by *Neisseria meningitidis* bacteria, particularly group B (NmB) strains, and by *E. coli* K1. The invention provides a de-N-acetylated PS derivative in which one or more residues of the PS has been modified by de-N-acetylation. The invention also includes derivatives in which one or more of the N-acetyl groups of PS containing de-N-acetylated PS are replaced with other N-acyl groups, usually a lower acyl group of $C_2$-$C_3$. Further, the invention includes de-N-acetylated PS derivatives containing long chain hydrocarbons, as well as conjugates in which the de-N-acetylated PS derivative is linked to a carrier, e.g., a carrier protein.

36 Claims, 19 Drawing Sheets
(1 of 19 Drawing Sheet(s) Filed in Color)

OTHER PUBLICATIONS

Moreno et al. Immunological properties of monoclonal antibodies specific for meningococcal polysaccharides: the protective capacity of IgM antibodies specific for polysaccharide group B. 1983 J Gen Microbiol 129 (Pt 8):2451.

Mandrell et al. "Complement-mediated bactericidal activity of human antibodies to poly alpha 2→8 N-acetylneuraminic acid, the capsular polysaccharide of *Neisseria meningitidis* serogroup B.", 1995 J Infect Dis 172:1279.

Raff et al. "Human monoclonal antibody with protective activity for*Escherichia coli* K1 and *Neisseria meningitidis* group B infections", 1988 J Infect Dis 157:118.

Rohr et al. Structure and biosynthesis of surface polymers containing polysialic acid in *Escherichia coli*. 1980 J Biol Chem 255:2332.

Azmi et al. "Variable region sequences and idiotypic expression of a protective human immunoglobulin M antibody to capsular polysaccharides of *Neisseria meningitidis* group B and *Escherichia coli* K1", 1994 Infect Immun 62:1776-1786.

Ashton et al. "Protective efficacy of mouse serum to the N-propionyl derivative of meningococcal group B polysaccharide", 1989 Microb Pathog 6:455-458.

Bruge, et al. "Clinical evaluation of a group B meningococcal N-propionylated polysaccharide conjugate vaccine in adult, male volunteers", Vaccine, 22 (2004) 1087-1096.

Baumann, et al., "Comparison of the conformation of the epitope of $\alpha(2\rightarrow 8)$ polysialic acid with its reduced and N-acyl derivatives", Biochemistyr 1993, 32, 4007-4013.

Brisson et al., "Helical eptope of the group B meningococcal $\alpha(2\rightarrow 8)$-Linked sialic acid polysaccharide", Biochemistry 1992, 31, 4996-5004.

Coquillat et al., "Activity of cross-reactivity of antibodies induced in mice by immunization with a group B meningococcal conjugate", Infect and Immun, 2001, vol. 69, No. 11, 7130-7139.

Devi et al., "Preclinical evaluation of group B *Neisseria meningitidis* and *Escherichia coli* K92 capsular polysaccharide-protein conjugate vaccines in juvenile rhesus monkeys." 1997, Infect Immun 65:1045-52.

Evans, et al., "Evidence for the extended helical nature of polysaccharide epitopes. The 2.8 Å resolution structure and thermodynamics of ligand binding of an antigen binding fragment specific for $\alpha(2\rightarrow 8)$- polysialic acid", Biochemistry, 1995, 34, 6737-6744.

Guo et al., "Protein-polysaccharide conjugation", 2001, Humana Press Inc. p. 49-61.

Fusco et al. "Preclinical evaluation of a novel group B meningococcal conjugate vaccine that elicits bactericidal activity in both mice and nonhuman primates," (1997) J. Infect. Dis. 175:364-72.

Goldschneider et al., "Human Immunity to the Meningocuccus. I The Role of Humoral Antibodies", 1969, *J. Exp. Med*. 129:1307-1326.

Granoff et al. "Bactericidal monoclonal antibodies that define unique meningococcal B polysaccharide eptopes that do not cross-react with human polysialic acid", 1998 J Immunol 160:5028-5036.

Kabat, et al. "The epitope associated with the binding of the capsular polysaccharide of the group B meningococcus and of *Escherichia coli* K1 to a human monoclonal macroglobulin IgMNOV", J. Exp. Med. Aug. 1, 1988;168(2):699-711.

Hong, et al., "Inhibitory effect of K-76 monocarboxylic acid, and anticomplementary agent, on the C3b inactivator system", The J Immunol, 19981, vol. 127, No. 1, pp.104-108.

Jennings et al., "Determinant specificities of the groups B and C polysaccharides of *Neisseria meningitides*", 1981, supra Jennings 1985 J Immunol 134:2651-57.

Jennings et al. "Induction of meningococcal group B polysaccharide-specific IgG antibodies in mice by using an N-propionylated B polysaccharide-tetanus toxoid conjugate vaccine", 1986, J Immunol 137:1708-1713.

Jennings et al. "N-propionylated group B meningococcal polysaccharide mimics a unique eptode on group B *Neisseria meningitides*", 1987, J Exp Med 165:1207-1211.

Jennings et al. "Unique intermolecular bactericidal epitope involving the homosialopolysaccharide capsule on the cell surface of group B *Neisseria meningitidis* and *Escherichia coli* K1¹", 1989 J Immunol 142:3585-3591.

Lifely et al., "Immune responses in mice to different noncovalent complexes of meningococcal B polysaccharide and outer membrane proteins", Infection & Immunity, 1988, vol. 56, No. 12, p. 3221-3227.

Lifely et al., "Sialic acid polysaccharide antigens of *Neisseria meningitidis* and *Escherichia coli*: Esterification between adjacent residues", Carbohydrate Research, 1981, 94, 193-203.

Lifely et al., "Specificity of the immune response to the group B polysaccharide of *Neisseria meningitidis*", Immunology, 1991, 74, 490-496.

Michon, et al., "Conformational differences between linear $\alpha(2\rightarrow 8)$—linked homosialooligosaccharides and the epitope of the group B meaningococcal polysaccharide", Biochemistry, 1987, 26, 8399-8405.

Moreno et al. "Immunity and protection of mice against *Neisseria meningitidis* group B by vaccination, using polysaccharide complexed with outer membrane proteins: a comparison with purified B polysaccharide", Infection & Immunity, 1985, vol. 47, No. 2, 527-533.

Pandey, et al, "Immunoglobulin allotypes and immune response to meningococcal group B polysaccharide", J. Clin. Invest, 1981, vol. 68, 1378-1380.

Pon et al. "N-propionylated group B meningococcal polysaccharide mimics a unique bactericidal capsular epitope in group B *Neisseria meningitidis*", 1997 J Exp Med 185:1929-1938.

R. Roy et al. "Efficient Synthesis of alpha(2-8)-linked N-Acetyl and N-Glycolylneuraminic Acid Disaccharides from Colominic Acid", Glycoconjugate Journal, vol. 7, 1990, pp. 3-12.

Sjoberg, et al. "Expression of De-N-acetyl-gangliosides in human melanoma cells is induced by genistein or nocodazole", The journal of Biological Chemistry, 1995, vol. 270, No. 7, 2921,2930.

Stephens et al. "Insertion of Tn916 in *Neisseria meningitidis* resulting in loss of group B capsular polysaccharide", 1991, Infect Immun 59:4097-4102.

Shin et al. "Monoclonal antibodies specific for *Neisseria meningitidis* group B polysaccharide and their peptide mimotopes", 2001 Infect Immun 69:3335-3342.

Wyle et al., "Immunologic response of man to group B meaningococcal polysaccharide vaccines", 1972, *J. Infect. Dis*. 126: 514-522.

Zollinger, et al., "Complex of meningococcal group B polysaccharide and type 2 outer membrane protein immunogenic in man", 1979, *J. Clin. Invest*. 63: 836-834.

Chammas et al. De-N-acetyl-gangliosides in Humans: Unusual Subcellular Distribution of A Novel Tumor Antigen. Cancer Research. Mar. 15, 1999, vol. 59, pp. 1337.1346, see Table 1, p. 1338, second col., p. 1343, first col., lines 7-8.

Chapman, A. Pegylated antibodies and antibody Fragments for improved therapy: a review. Advanced Drug Delivery Reviews. 2002, vol. 54, pp. 531-545, see abstract.

Gabri et al. Role of cell surface OM3 ganglioside and sialic acid in the antitumor activity of a GM3-based vaccine in the murine B16 melanoma model. Journal of Cancer Research and Clinical Oncology. 2002, vol. 128, pp. 669-677, see p. 670, second col. and p. 672, first col.

Hellstrom et al. Strong antitumor activites of IgG3 antibodies to a human melanoma associated ganglioside. Proceedings of the National Academy of Sciences. Mar. 1985, vol. 82, pp. 1499-1502, see p. 1500 and p. 1502, first col.

Herlyn et al, 'Production and characterization of monoclonal antibodies against human malignant melanoma', Accession No. 84129677, Abstract, Cancer Investigations, 1983, vol. I, No. 3, pp. 215-224.

Moe et al. Epitopes Recognized by a Nonautoreactive Murine Anti-N-Propionyl Meningococcal Group B Polysaccharide Monoclonal Antibody. Infection and immunity. Apr. 2005, vol. 73, pp. 2123-2128, p. 2126, legend for figure 3, p. 2124, first col., p. 2124, second col., lines 3-4 and p. 2126, second col., lines 30-31.

Sjoberg et al. Expression of De-N-acetyl-gangliosides in Human Melanoma Cells Is Induced by Genistein or Nocodazole. The Journal of Biologilcal Chemistry. Feb. 17, 1995, vol. 270, pp. 2921-2930, see pp. 2927-2930 and p. 2924, second col., first full paragraph.

* cited by examiner

FIGURE 2

Fine antigenic specificities of the anti-N-Pr NmB PS mAbs ("SEAM") that have minimal or no reactivity with human polysialic acid antigens[a].

| mAb | IgG subclass | ELISA reactivity to N-Ac NmB PS[b] | ELISA Inhibition of binding by N-Pr NmB PS oligosaccharides[c] | Cross-reactivity with human PSA[d] |
|---|---|---|---|---|
| SEAM 2 | 3 | 0 | 0 | 0 |
| SEAM 3 | 2b | 0 | +++ | 0 |
| SEAM 12 | 2a | ++ | 0 | + |
| SEAM 18 | 2b | +++ | +++ | + |

[a] Data taken from Granoff and Moe, US Pat. No. 6,048,527.

[b] Ab binding to N-Ac NmB PS: 0, OD <0.15; +, OD = 0.15-0.5; ++, OD = 0.5-1.0; +++, OD > 1.0 when tested at 5-25 µg/ml of Ab by ELISA.

[c] Inhibition of Ab binding to N-Pr NmB PS in an ELISA by soluble N-Pr NmB PS (Dp < 6; average Dp = 3.8): 0, < 20%; +, 21%-48%; ++, 49%-74%; +++, 75%-100% inhibition when tested with an [Ab] giving an OD = 0.5 in 30 m.

[d] Binding to polysialic acid on CHP-134 neuroblastoma cells as measured by indirect fluorescence flow cytometry: 0, no binding activity to PSA when tested at 100 µg/ml of Ab; ++, binding activity detected at 10 µg/ml of Ab; +, binding activity detected at 100 µg/ml but not 10 µg/ml.

FIGURE 5

Summary of inhibition of anti-N-Pr NmB PS mAb (SEAM mAb) binding to N-Pr NmB PS by PS derivatives in ELISA[a].

| Inhibitor | SEAM mAb | | | |
|---|---|---|---|---|
| | 2 | 3 | 12 | 18 |
| NmB PS[b] | >100 | >100 | >100 | >100 |
| Colominic acid | >100 | >100 | >100 | >100 |
| Deacetyl colominic acid | >100 | 0.8 | >100 | 1.7 |
| N-Ac NmB PS | >100 | 0.32 | 1.2 | 0.3 |
| Ox N-Ac NmB PS | >100 | 10.1 | >100 | 12.6 |
| H[+] N-Ac NmB PS | >100 | 1.9 | >100 | >100 |
| Ox H[+] N-Ac NmB PS | >100 | 13.4 | >100 | >100 |
| N-Pr NmB PS | 0.1 | 0.004 | 0.004 | 0.001 |
| Ox N-Pr NmB PS | <0.02 | 0.07 | <0.02 | <0.02 |
| H[+] N-Pr NmB PS | 1 | 0.03 | 0.05 | 0.03 |
| Ox H[+] N-Pr NmB PS | 1.5 | 2.2 | 1.3 | 1.8 |

[a]Concentrations in µg/ml inhibiting 50% of maximum OD at 405 nm in 30 min.

[b]Isolated from *N. meningtidis* group B bacteria as described in Constantino et al. (1999 Vaccine 17:1251). The NmB PS used in this assay completely inhibits binding of anti-NmB PS mAb 2-1-B, which binds to both N-Ac NmB PS and N-Pr NmB PS in ELISA, at concentrations less than 0.1 µg/ml (data not shown).

FIGURE 6

Inhibition of complement mediated bactericidal activity of anti-N-Pr NmB PS mAbs as measured against *N. meningitidis* group B strain 8047.

| Inhibitor | Anti-N-Pr NmB PS mAb[a] | | | |
|---|---|---|---|---|
| | SEAM 2 | SEAM 3 | SEAM 12 | SEAM 18 |
| Native N-Ac NmB PS[b] | >50 | >14 | >12 | >50 |
| De-N-Acetyl NmB PS | >50 | 4 | >50 | >50 |
| Resynthesized N-Acetyl NmB PS[d] | >50 | 0.6 | >50 | 12 |
| Synthesized N-Propionyl NmB PS[e] | 0.03 | 0.2 | 0.2 | <0.04 |

[a]Concentrations of NmB PS derivative (μg/ml) that result in inhibition of bactericidal activity of the mAbs against strain 8047. Inhibition was defined by 50% survival of bacteria when incubated with complement and a concentration of mAb that gives 0% survival (that is, 100% killing) in the absence of the inhibitor. The CFU/ml at 60 min was > 200% of the CFU/ml at time 0. Control mAb anti-capsular 2-1-B was inhibited by NmB PS but not by any of the other derivatives including re-synthesized N-Ac NmB PS and a control anti-PorA P1.2 mAb was not inhibited by NmB PS or any of the NmB PS derivatives. None of the mAbs was inhibited by 50 μg/ml of *N. meningitidis* group A polysaccharide.

[b]Isolated from *N. meningitidis* group B bacteria as described in Constantino et al. (1999 Vaccine 17:1251).

[c]Prepared from *E. coli* K1. Colominic acid is chemically and immunologically identical to that of NmB PS (Rohr et al. 1980 J Biol Chem 255:2332; Bhattacharjee et al. 1975 J Biol Chem 250:1926) except that some *E. coli* K1 strains express C7 or C9 O-acetylated polysaccharide (Ørskov et al. 1979 J Exp Med 149:669).

[d]Re-synthesized N-Ac NmB PS that has been de-acetylated and re-N-acetylated as described in Example 1.

[e]NmB PS that has been de-acetylated and N-propionylated as described in Example 1.

FIGURE 9

SUMMARY OF MS DATA FOR POLYSACCHARIDE SELECTED BY SEAM MABS

|  |  |  | Selecting "SEAM" monoclonal antibody | | | |
|---|---|---|---|---|---|---|
| Ion putative structure | Calculated mass (Daltons) | | 2 | 3 | 12 | 18 |
|  | Monoisotopic | Average | Observed mass/charge | | | |
| [II +Na$^+$]$^-$ | 579.16 | 579.46 | 579.378 | 579.400 | 579.482 | 1. 579.328 |
| [I]$^-$ | 559.20 | 559.50 | 559.290 | 559.390 | 559.314 | 559.525 |
| [II]$^-$ | 557.18 | 557.48 | 557.289 | 557.392 | 557.403 | 557.305 |
| [III or IV]$^-$ | 541.17 | 541.45 | 541.162 | 541.128 | 541.168 | - |
| [V]$^-$ | 539.17 | 539.46 | 539.169 | 539.249 | 539.157 | - |
| [VI]$^-$ | 523.18 | 523.47 | 522.731 | 522.867 | 522.813 | - |
| [VII]$^-$ | 515.17 | 515.44 | 514.540 | 514.710 | 514.616 | - |
| [II-CH$_2$O]$^-$ | 527.17 | 527.45 | - | - | 526.975 | 526.991 |
| [Mixture of VII,VIII]$^-$ | 499.18, 497.16 |  | 498.219 | 498.289 | 498.273 | - |

The estimate of error for observed masses is ±0.1%.

Structure I

$C_{20}H_{35}N_2O_{16}^-$
Exact Mass: 559.20
Mol. Wt.: 559.50
C, 42.93; H, 6.31; N, 5.01; O, 45.75

Structure II

$C_{20}H_{33}N_2O_{16}^-$
Exact Mass: 557.18
Mol. Wt.: 557.48
C, 43.09; H, 5.97; N, 5.03; O, 45.92

Structure III

$C_{20}H_{33}N_2O_{15}^-$
Exact Mass: 541.19
Mol. Wt.: 541.48
C, 44.36; H, 6.14; N, 5.17; O, 44.32

Structure IV

$C_{20}H_{33}N_2O_{15}^-$
Exact Mass: 541.19
Mol. Wt.: 541.48
C, 44.36; H, 6.14; N, 5.17; O, 44.32

Structure V

$C_{20}H_{31}N_2O_{15}^-$
Exact Mass: 539.17
Mol. Wt.: 539.46
C, 44.53; H, 5.79; N, 5.19; O, 44.49

Structure VI

$C_{20}H_{31}N_2O_{14}^-$
Exact Mass: 523.18
Mol. Wt.: 523.47
C, 45.89; H, 5.97; N, 5.35; O, 42.79

Structure VII

$C_{18}H_{31}N_2O_{15}^-$
Exact Mass: 515.17
Mol. Wt.: 515.44
C, 41.94; H, 6.06; N, 5.43; O, 46.56

Structure VI

$C_{18}H_{31}N_2O_{14}^-$
Exact Mass: 499.18
Mol. Wt.: 499.44
C, 43.29; H, 6.26; N, 5.61; O, 44.85

Structure VII

C$_{18}$H$_{31}$N$_2$O$_{14}$⁻
Exact Mass: 499.18
Mol. Wt.: 499.44
C, 43.29; H, 6.26; N, 5.61; O, 44.85

Structure VIII

C$_{18}$H$_{29}$N$_2$O$_{14}$⁻
Exact Mass: 497.16
Mol. Wt.: 497.43
C, 43.46; H, 5.88; N, 5.63; O, 45.03

Exact Mass: 1000.5

Exact Mass: 944.47

Exact Mass: 1014.51

Exact Mass: 1000.5

Exact Mass: 1000.5

Exact Mass: 1000.5

Exact Mass: 1000.5

Exact Mass: 1000.5

Exact Mass: 1000.5

Exact Mass: 1016.53

Exact Mass: 1016.53

Exact Mass: 1016.53

Exact Mass: 944.47

Exact Mass: 944.47

Exact Mass: 944.47

Exact Mass: 958.48

Exact Mass: 958.48

Exact Mass: 958.48

Figure 38

Concentration for mAb binding to dodecylamine PS antigens as determined by direct binding ELISA[a,b]

| SEAM mAb | Non-reducing end MBPS | Non-reducing end dodecyl Re-N-Ac MBOS/PS | | | Non-reducing end dodecyl N-Pr MBOS/PS | |
|---|---|---|---|---|---|---|
| | Dp>14 | OS, Dp<7 | PS, Dp>14 | OS, Dp<7 | PS, Dp>14 | |
| 2 | >10 | >10 | >10 | >10 | 0.94 | |
| 3 | >10 | 0.05 | 0.05 | 0.03 | 0.03 | |
| 12 | 0.52 | 0.37 | 0.29 | 0.11 | 0.01 | |
| 18 | >10 | >10 | >10 | 0.87 | 0.05 | |
| 35 | >10 | >10 | >10 | 5.73 | 0.5 | |

[a] Concentration of mAb in micrograms/ml required to give an $OD_{405}$ nm equal to 0.5 in 1 hr by ELISA with the non-reducing end dodecylamine MBPS derivative coated on the plate and the bound mAb detected using goat anti-mouse IgG, M, A alkaline phosphatase conjugate secondary antibody as described in the text. Colominic acid was used to prepare this derivative. Since the colominic acid is from an *E. coli* K1 strain that does not O-acetylate the hydoxyl groups on C7 and C9, the polysaccharide is chemically identical to meningococcal group B polysaccharide (MBPS). N-Pr, N-propionyl; N-Ac, N-acetyl; OS oligosaccharide; PS, polysaccharide; Dp, degree of polymerization.

[b] Preparation and composition of MBPS derivatives are as described in the text.

Figure 39

Concentration for mAb binding to BSA-PS derivative conjugate antigens as determined by direct binding ELISA[a,b]

| SEAM mAb | Non-reducing end MBPS | Non-reducing end dodecyl Re-N-Ac MBOS/PS | | | Non-reducing end dodecyl N-Pr MBOS/PS | |
|---|---|---|---|---|---|---|
| | Dp>14 | OS, Dp<7 | PS, Dp>14 | | OS, Dp<7 | PS, Dp>14 |
| 2 | >10 | >10 | >10 | | 4.6 | 3.8 |
| 3 | >10 | 0.012 | 0.014 | | 0.018 | 0.016 |
| 12 | 0.52 | 0.18 | 0.14 | | 0.01 | 0.02 |
| 18 | >10 | >10 | >10 | | 0.07 | 0.007 |
| 35 | >10 | >10 | >10 | | 33 | 0.23 |

[a] Concentration of mAb in micrograms/ml required to give an OD$_{405}$ nm equal to 0.5 in 1 hr by ELISA with the non-reducing end BSA MBPS derivative coated on the plate and the bound mAb detected using goat anti-mouse IgG, M, A alkaline phosphatase conjugate secondary antibody as described in the text.

[b] Preparation and composition of MBPS derivatives are as described in the text. Colominic acid was used to prepare this derivative. Since the colominic acid is from an *E. coli* K1 strain that does not O-acetylate the hydoxyl groups on C7 and C9, the polysaccharide is chemically identical to meningococcal group B polysaccharide (MBPS). N-Pr, N-propionyl; N-Ac, N-acetyl; OS oligosaccharide; PS, polysaccharide; Dp, degree of polymerization.

POLYSACCHARIDE DERIVATIVES AND USES IN INDUCTION OF AN IMMUNE RESPONSE

CROSS-REFERENCE TO RELATED APPLICATIONS

This application claims priority benefit to U.S. provisional application Ser. No. 60/582,672, filed Jun. 23, 2004, which application is incorporated herein by reference in its entirety.

STATEMENT REGARDING FEDERALLY SPONSORED RESEARCH

This invention was made with government support under grants no. AI46464 and AI45642 awarded by the National Institute of Allergy and Infectious Diseases, and the National Institute of Health. The government may have certain rights in this invention.

FIELD OF THE INVENTION

This invention relates to polysaccharide derivatives, compositions containing same and their methods of use.

BACKGROUND OF THE INVENTION

*Neisseria meningitidis*, a Gram-negative bacterium, is a major human pathogen that causes bacterial meningitis and sepsis. The attack and morbidity rates are highest in children under 2 years of age. Five major capsular groups account for nearly all disease-producing isolates. These are defined by different polysaccharide capsules designated A, B, C, Y and W-135. Vaccines are available for prevention of disease caused by group A, C, Y and W-135 organisms. However, there is no vaccine available for prevention of disease caused by group B strains (hereafter referred to as "NmB"), which account for 50 percent or more of all cases of meningococcal disease in children in the US and Europe (Jones, D., in "Meningococcal Disease," John Wiley & Sons, New York, 1995).

The meningococcal group B capsular polysaccharide (referred to herein as NmB capsular polysaccharide or "NmB PS") is composed of a homolinear polymer of alpha2→8 N-acetyl neuraminic acid (polysialic acid; hereafter referred to as "PSA"). This capsular PS is conserved across all NmB strains, and is also found in pathogenic *Escherichia coli* K1. NmB PS is chemically identical to polysialic acid that is abundantly expressed by fetal tissues, including brain, heart, and kidney.

The Group B capsule is an important virulence determinant. For example, mutants that are deficient in capsular expression are serum-sensitive and non-pathogenic (Stephens 1991, Infect Immun 59:4097). Evidence also indicates that serum antibody to the group B polysaccharide confers protection against disease by activating complement-mediated bacteriolysis and/or opsonization (Griffiss, J. M., in "Meningococcal Disease," John Wiley & Sons, New York, 1995).

However, efforts to employ the NmB capsular polysaccharide as a vaccine component have been hampered by its poor immunogenicity (Wyle et al., 1972, *J. Infect. Dis.* 126: 514-522; Zollinger, et al., 1979, *J. Clin. Invest.* 63: 836-834), even when conjugated to a carrier protein (Devi et al., 1997, Infect Immun 65:1045; Jennings et al., 1981, J Immunol 127:1011). The poor immunogenicity is attributed to immunologic tolerance induced by fetal exposure to cross-reactive polysialated glycoproteins expressed in a variety of host tissues such as the neural cell adhesion molecule ("NCAM") (Finne et al. 1983, Biochem Biophys Res Commun 112:482; Hayrinen et al. 1995, J Infect Dis 171:1481). Anti-NmB PS monoclonal antibodies (mAbs) have been prepared by immunizing mice with killed group B bacteria (Mandrell et al. 1982 J Immunol 129:2172; Moreno et al. 1983 J Gen Microbiol 129 (Pt 8):2451; Shin et al. 2001 Infect Immun 69:3335), or by immunizing NZB mice with plain polysaccharide or bacteria (Frosch et al. 1985 Proc Natl Acad Sci USA 82:1194; Hurpin et al. 1992 Hybridoma 11:677). Human NmB PS-reactive IgM mAbs or paraproteins have also been described (Raff et al. 1988 J Infect Dis 157:118; Rohr et al. 1980 J Biol Chem 255:2332; Azmi et al. 1994 Infect Immun 62:1776; Mandrell et al. 1995 J Infect Dis 172:1279). These mAbs or paraproteins elicit complement-mediated bactericidal activity. Thus development of vaccines based on polysaccharide as an antigen, but with improved immunogenicity, has been a particular focus in the field.

In the 1980s, Jennings and coworkers investigated the immunogenicity of various derivatives of NmB PS (Jennings et al., 1981, supra Jennings 1985 J Immunol 134:2651; Ashton et al. 1989 Microb Pathog 6:455; Pon et al. 1997 J Exp Med 185:1929). Conjugate vaccines containing polysaccharides in which N-acetyl groups of NmB PS were replaced with a variety of more hydrophobic acyl groups, particularly propionyl (N-Pr), were immunogenic and elicited protective bactericidal antibody. The resulting modified polysaccharide was conjugated to a protein carrier (Jennings et al. 1986, J Immunol 137:1708, 1986; Jennings et al. 1987, J Exp Med 165:1207; Jennings et al., 1981, supra; Jennings et al. 1985 supra; Asthon et al. 1989, supra; Pon et al. 1997, supra; U.S. Pat. No. 4,727,136) and found to be immunogenic in experimental animals, eliciting IgG antibodies that activated complement-mediated bacteriolysis in vitro, and conferring passive protection in experimental animals infected with NmB. This vaccine was immunogenic in sub-human primates, inducing serum antibodies that activate complement-mediated bacteriolysis (Fusco et al., 1997, *J. Infect. Dis.* 175: 364-372). In humans, bactericidal antibodies are known to confer protection against developing meningococcal disease (Goldschneider et al.,. 1969, *J. Exp. Med.* 129:1307).

However, a subset of the antibodies induced by the currently available vaccines has anti-host autoantibody activity to unmodified NmB PS (i.e. N-acetyl-NmB PS) (Hayrinen et al. 1995 J Infect Dis 171:1481; Granoff et al., 1998, *J. Immunol;* 160: 5028-5036). Since PSA is abundantly expressed in fetal and newborn tissue, especially on NCAMs found in brain tissue, this approach raises serious safety concerns. Remarkably, a subset of bactericidal antibodies elicited by N-Pr and other derivatives of NmB PS bound specifically with bacteria and not with host tissues, and were not absorbed by NmB PS affinity matrices (Jennings et al. 1989 J Immunol 142:3585; Pon et al. 1997, supra). Granoff et al. immunized mice with N-Pr NmB PS conjugated to tetanus toxoid and prepared a panel of monoclonal anti-N-Pr NmB PS antibodies (mAbs) (Granoff et al. 1998 J Immunol 160:5028). A number of the mAbs elicited complement-mediated bactericidal activity in vitro, and conferred passive protection against bacteremia in an infant rat model. The protective mAbs were subclassified into four different fine antigenic specificity groups based on the presence or absence of cross-reactivity with native NmB PS, and the ability of N-Pr-MB oligosaccharides (average degree of polymerization [Dp]= 3.8) to inhibit anti-N-Pr-NmB PS binding in an ELISA.M-Abs, representative of each of the four fine antigenic specificity groups, showed minimal or no detectable autoreactivity with the host polysialic acid based on flow cytometry studies with the human cell line CHP-134 (Granoff et al. 1998, supra), which express long chain polysialic acid, and immunohistology with human fetal tissue. The mAbs bound to the surface of live encapsulated group B bacteria but riot to a capsular deficient mutant. The epitopes on the bacteria recognized by these anti-N-Pr NmB PS mAbs were not defined.

The present invention overcomes the disadvantages of prior art approaches to vaccination by providing vaccine compositions and meth

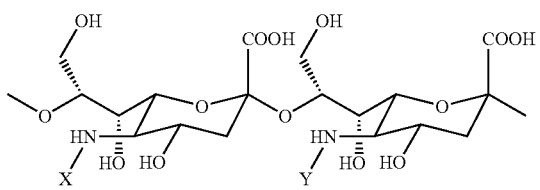

wherein X and Y are independently an amine protecting group, or a saturated or unsaturated acyl group, and wherein the PS derivative is optionally further comprises a carrier protein conjugated to a sialic acid residue of the PS derivative, or optionally further comprises an amidated sialic acid residue having an alkyl secondary amine at a non-reducing end of the PS derivative. PS derivatives generally have one or more such structures positioned within the polymer. In related embodiments, the acyl group is a saturated acyl group and acetyl or propionyl.

In related embodiments, the PS derivative comprises a structure represented by the formula:

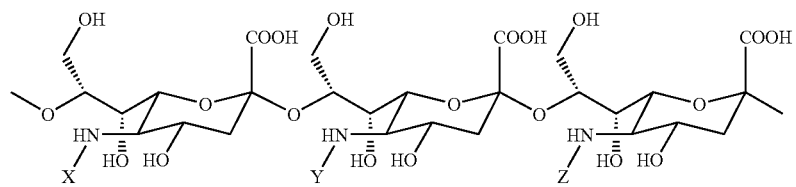

where X, Y and Z are independently an amine protecting group, with the proviso that at least one of X, Y, and Z is an amine protecting group and at least one of X, Y, and Z is a saturated or unsaturated acyl group. PS derivatives in this embodiment generally have one or more such structures positioned within the polymer. In related embodiments, the acyl group is a saturated acyl group and acetyl or propionyl.

In other embodiments, the invention features methods of immunizing a subject by administering an amount of a PS derivative of the invention in an amount effective to elicit an immune response, where such administering is effective to elicit an immune response in the subject against *Neisseria meningitidis* group B. In other embodiments, the invention features methods of immunizing a subject by administering an amount of a PS derivative of the invention in an amount effective to elicit an immune response, where such administering is effective to elicit an immune response in the subject against *E. coli* K1.

In other embodiments, the invention features methods for providing passive protection against a bacterial infection by administering to a subject bactericidal antibodies elicited by immunization of a host with a PS derivative of the invention, where such administering provides for protection of the subject against *Neisseria meningitidis* group B or against *Escherichia coli* K1.

The invention also features methods for producing a PS derivative involving reacting an at least partially de-N-acetylated PS molecule with a mixture comprising an amine protecting reagent and an acylating reagent in the presence of an organic solvent, where the reaction produces a protected PS derivative having an amine protecting group and an N-acylated group. In related embodiments, the methods further involve treating the protected PS derivative under conditions to remove the amine protecting group to produce a PS derivative. In further related embodiments, the methods further involve conjugating the protected PS derivative to a carrier protein to produce a conjugated protected PS derivative and treating the conjugated protected PS derivative under conditions to remove the amine protecting group, so that a conjugated PS derivative is produced. In other related embodiments, the methods further involve reacting the protected PS derivative with an N-acyl amine reagent to produce an amidated protected PS derivative having an amidated sialic acid residue having an alkyl secondary amine, and treating the amidated protected PS derivative under conditions to remove the removing the amine protecting group, so that a PS derivative having an amidated sialic acid residue having an alkyl secondary amine at is produced. The invention also contemplates PS derivatives generated by these methods.

The invention also features methods of producing a polysaccharide (PS) derivative by culturing a *Neisseria meningitidis* Group B bacterium in a growth medium comprising N-acyl-mannosamine and an amine-protected mannosamine, so that culturing provides for production of a protected PS derivative having an amine protecting group and an N-acylated group. In related embodiments, the bacterium is deficient in production of capsule polysaccharide in the absence of supplemental mannosamine. In related embodiments, the method further involves conjugating the protected PS derivative to a carrier protein to produce a conjugated protected PS derivative, and treating the conjugated protected PS derivative under conditions to remove the amine protecting group so as to produce a conjugated PS derivative. In related embodiments, the method further involves reacting the protected PS derivative with an N-acyl amine reagent to provide an alkyl secondary amine on a sialic acid residue of the protected PS derivative, and treating the protected PS derivative treating under conditions to remove the removing the amine protecting group, wherein a PS derivative having a sialic acid residue containing an alkyl secondary amine is produced. The invention also contemplates PS derivatives generated by these methods.

The invention further features methods for identifying a polysialic acid (PSA) epitope bound by an antibody by contacting a PSA derivative with an antibody, said contacting being under conditions suitable for formation of antigen-antibody complexes of the antibody and the PS derivative, and contacting the antigen-antibody complex with a sialidase under conditions suitable for removal of sialidase-accessible PSA derivative residues of the antigen-antibody complex, such that PSA derivative residues remaining in the antigen-antibody complex following sialidase treatment define an epitope bound by the antibody.

The invention is advantageous in that the NmB PS derivatives of the invention can be used to elicit an immune response in a subject, which can include serum bactericidal antibodies that specifically bind NmB bacteria with little or no detectable cross-reactivity with polysialic residues of normal host tissue.

Other advantages of the invention will be readily apparent to the ordinarily skilled artisan upon reading the disclosure herein.

BRIEF DESCRIPTION OF THE DRAWINGS

The patent or application filed contains at least one drawing executed in color. Copies of this patent or patent application publication with color drawings will be provided by the Office upon request and payment of the necessary fee.

FIG. 2 is a table describing the SEAM antibodies used in the Examples to facilitate identification of the epitope(s) of an NmB PS derivative specifically bound by bactericidal anti-NmB PS antibodies, and not by antibodies that cross-react with host PSA.

FIG. 5 is a table providing a summary of the results of ELISA inhibition assays to determine the inhibitory activity of various NmB PS derivatives upon binding of SEAM monoclonal antibodies to N-Pr NmB PS.

FIG. 6 is a table providing a summary of the results of assays to determine activity of various NmB PS derivatives in inhibiting complement-mediated bactericidal activity of anti-N-Pr NmB PS mAbs as measured against *N. meningitidis* group B strain 8047.

FIG. 9 is a table summarizing the observed masses for each sample and theoretical masses of corresponding ions that are consistent with the observed masses.

FIG. 38 is a table summarizing the results of mAb binding to dodecylamine MBPS derivatives as measured by direct binding ELISA. The mAbs SEAM-2, 3, 12, and 18 are described in U.S. Pat. No. 6,048,527. The mAb SEAM 38 is described in Granoff et al. 1998, J. Immunol. 160:5028.

FIG. 39 is a table summarizing the results of mAb binding to BSA-MBPS derivative conjugates as measured by direct binding ELISA. The mAbs SEAM-2, 3, 12, and 18 are described in U.S. Pat. No. 6,048,527. The mAb SEAM 38 is described in Granoff et al. 1998, J. Immunol. 160:5028.

Figure 1:
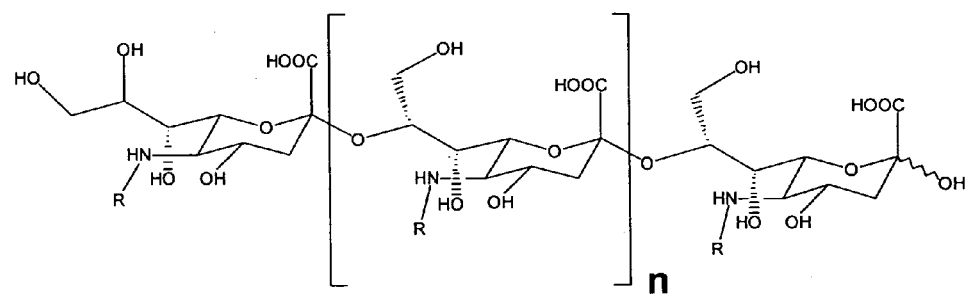
FIG. 1 provides the structure of NmB PS following de-N-acetylation according to the invention. R is H on most residues to provide a free amine (on a deacetylated group). In a small fraction of residues in the de-N-acetylated product, R may be $CH_3C=O$ (an acetyl group). "n" represents a number of sialic acid residues in the polymer, which may have the value of "n" in other formulae described herein.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an antigen" includes a plurality of such antigens and reference to "the peptide" includes reference to one or more peptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention is based on the discovery that NmB contains de-N-acetyl residues in the capsular polysaccharide (PS) and that NmB PS-based vaccines that contain de-N-acetyl residues (about or greater than 25%) can elicit antibodies that are protective against disease caused by NmB, but which do not cross-react or are minimally cross-reactive with self polysialic acid (PSA) antigens expressed by human tissues. Specifically, the inventors have discovered that the minimal epitope of such vaccines is a PS disaccharide in which one or both residues contain de-N-acetyl residues.

The minimal epitope of such anti-NmB PS antibodies is a disaccharide unit of such NmB PS derivatives, where the disaccharide unit comprises one or more residues in which the N-acetyl group on the C-5 amino group has been removed or, where one of the two residues are de-N-acetylated, the second residue contains an N-acetyl group (but, in some embodiments, not an N-propionyl group). The disaccharide unit defining this minimal epitope may be at the reducing end, the non-reducing end, or within the polysaccharide. De-N-acetylated residues in the context of PSA containing N-acylated residues are immunogenic and elicit antibodies that are reactive the NmB capsule but are minimally reactive or not detectably reactive with human PSA antigens. This approach provides a safe and efficacious method for the prevention of disease caused by NmB. Further, since the capsular PS of *E. coli* K1 is chemically and immunologically identical to that of NmB, the invention is also applicable to production of PS derivatives for use in prevention of *E. coli* K1 disease.

The de-N-acetylated NmB polysaccharide epitope was identified using a panel of murine anti-N-Pr NmB polysaccharide mAbs (monoclonal antibodies) described in Granoff et al., 1998, J Immunol 160:5028 (anti-N-Pr NmB PS mAbs); U.S. Pat. No. 6,048,527 (anti-NmB antibodies); and U.S. Pat. No. 6,350,449 (anti-NmB antibodies). These mAbs (hereafter referred to as "SEAM" mAbs) were used to purify NmB polysaccharide derivatives.

The invention thus features de-N-acetylated PS epitopes, and formulations of such adapted for administration to a host to elicit an anti-NmB polysaccharide antibody response. In addition, since the capsular polysaccharide of *E. coli* K1 has the same structure as the capsular polysaccharide of *N. meningitidis*, the invention also features de-N-acetylated PS epitopes, and formulations of such adapted for administration to a host to elicit an anti-*E. coli* K1 polysaccharide antibody response.

The invention also encompasses conjugates of de-N-acetylated polysaccharide epitope-containing compounds in antigenic compositions suitable for administration to a host.

The invention also includes compositions comprising a de-N-acetylated PSA derivative of the invention as a monomeric unit, or a polymeric unit (e.g., two or more residues, which PSA may be provided in the compositions as a homopolymeric or heteropolymeric structure) of the composition. The composition can comprise additional residues attached at the non reducing terminus, reducing-terminus or both the non-reducing- and reducing-termini of a de-N-acetylated PSA of the invention.

The invention also features methods of making de-N-acetylated PS comprising contacting a de-N-acetylated PS with an acylating agent, such as an acyl anhydride, under conditions so that N-acylated residues of the resulting de-N-acetylated PS derivative represents less than 90%, less than 85%, less than 84%, less than 80%, less than 75%, less than 70%, less than 60%, or less than 55%, or less than 50% of the total residues of the compound (e.g.,. where the total residues in the compound is usually at least about 10-20 residues) and de-N-acetylated residues (residues with free amines) is at least 10%, at least 15%, at least 16%, at least 20% at least 25%, at least 30%, at least 40%, at least 45%, or at least 50% of total residues in the compound (e.g.,. where the total residues in the compound is usually at least about 10-20 residues). In this aspect, the invention provides the advantage of controlling the level of acylation of the final product, so as to provide a de-N-acetylated PS derivative having a desired level of acylation.

The invention further features methods of making de-N-acetylated PS comprising contacting an at least partially de-N-acetylated PS with a mixture of acylating agent and an amine protecting agent. In this aspect, the invention provides the advantage of protecting the C-5 amino group from undesirable side reactions that occur during preparation of PS-conjugate derivatives and is easily removed in the final product, so as to provide a de-N-acetylated PS derivative having a desired level of acylation.

The invention further features methods of making de-N-acetylated PS by biosynthesis in an NmB strain by supplementing the growth media with a mixture of N-trihaloacetyl-D-mannosamine and N-acetyl-D-mannosamine under conditions where the trihalo acylating agent represents less than 90%, less than 85%, less than 84%, less than 80%, less than 75%, less than 70%, less than 60%, or less than 55%, or less than 50% of the total N-acyl-D-mannosamine. In this aspect, the invention provides the advantage of efficiently producing PS with the C-5 amino group protected from undesirable side reactions that occur during preparation of PS-conjugate derivatives and is easily removed in the final product, so as to provide a de-N-acetylated PS derivative having a desired level of acylation.

The invention further features methods of eliciting an anti-NmB polysaccharide antibody response in a host by administration of one or more immunogenic doses of de-N-acetylated NmB polysaccharide or conjugate (also referred to herein as "PS conjugate"). The administrations are effective in eliciting an anti-NmB capsular polysaccharide antibody response with no significant or detectable host autoantibody production.

The invention also features methods of identifying PSA epitopes that elicit an immune response, e.g., that is protective against a bacterial pathogen, such as NmB or *E. coli* K1, but not anti-PSA antibodies that are reactive with normal host PSA antigens, comprising the steps of:

(1) contacting antibodies with a PS derivative, e.g., antibodies that bind NmB PS (anti-NmB PS antibodies), host PSA (anti-host PSA antibodies or "autoantibodies"), or both, where contacting is sufficient and under conditions suitable for formation of antigen-antibody complexes with the PS derivative; and (2) identifying epitopes bound to the antibodies as desired, e.g., epitopes that bind antibodies that bind to NmB PS but not host PSA, where epitope identification involves treatment of the antigen-antibody complexes with an appropriate enzyme (e.g., a sialidase, e.g., an endo- or exo-sialidase. Use of neuraminidase is of particular interest.

The method can further comprise affinity purification of the neuraminidase-treated antigen-antibody complexes followed by analysis (e.g., MALDI-TOF analysis) to determine the epitope. In related embodiments, the PSA derivative is presented as a library comprising different PSA derivatives.

Definitions

"PS" as used herein refers to polysaccharide, usually a capsular polysaccharide, particularly a capsular polysaccharide having one or more de-N-acetylated residues, including capsular polysaccharide of *N. meningitidis* or *Escherichia coli*, with *N. meningitidis* Group B and *E. coli* K1 being of particular interest. "NmB PS" as used herein refers to a PS of a Group B *N. meningitidis*. Reference to NmB PS throughout the specification is meant to be exemplary of PS structures amenable for production of compositions and use in methods of the invention.

"PS derivative" as used herein refers to a modified, usually chemically modified, polysaccharide (PS), particularly a PS of *Neisseria meningitidis* Group B or *Escherichia coli* K1, with PS derivatives having a free amine (i.e., a primary amine) in lieu of one or more N-acetyl groups being of particular interest. In general, PS derivatives do not encompass gangliosides or ganglioside derivatives.

"de-N-acetylated PS derivative" as used herein refers to a PS derivative having one or more de-N-acetylated residues, e.g., one or more free amines at the C-5 position of one or more residues of the polysaccharide derivative. The term "de-N-acetylated PS derivative" is not meant to imply that de-N-acetylated PS derivatives are limited to PS derivatives generated by a process involving removing an acetyl group from a PS molecule, but instead, unless specifically indicated otherwise, is meant to encompass de-N-acetylated PS derivatives generated by any suitable method (e.g., by a biosynthetic method in which free amines are generated in a de-N-acetylated PS derivative by removal of a trihaloacyl protecting group incorporated into the PS molecule during PS biosynthesis). Further, "de-N-acetylated residue" is used herein in the context of a PS derivative to refer to a sialic acid residue in the molecule that has, in lieu of a native acetyl group, a primary amine.

"Free amine" and "primary amine" are used interchangeably herein to refer to an NH2 group, as in, for example, $RNH_2$ where "R" is a sialic acid residue of a PS derivative of the invention.

"PS conjugate" as used herein refers to a conjugate of a carrier molecular (such as a carrier protein) and a homolinear polymer of alpha(2→8) N-acetyl neuraminic acid or any other polysaccharide containing this monomeric unit, or derivatives thereof, including de-N-acetylated PS derivatives of the invention. Of particular interest is a conjugate of a carrier protein and a derivative of *Neisseria meningitidis* capsular polysaccharide (particularly a Group B capsular polysaccharide), particularly a de-N-acetylated PS derivative of the invention. Also of particular interest is a conjugate of a carrier protein and a derivative of *E. coli* K1 capsular polysaccharide, particularly a de-N-acetylated PS derivative of the invention.

The terms "NmB conjugate" or "capsular polysaccharide conjugate" or NmB capsular polysaccharide conjugate" are intended to refer to a conjugate between a capsular polysaccharide of *N. meningitidis*, particularly Group B *N. meningitidis* capsular polysaccharide, including PS derivatives of the invention, and a carrier, such as tetanus toxoid, CRM197, recombinant *Neisseria meningitidis* Porin B protein, or proteins contained in *Neisseria meningitidis* outer membrane vesicles.

"Carrier" as used in the context of a carrier conjugated to a de-N-acetylated PS derivative of the invention generally refers to a substance that, when linked to an antigen, serves as a T-dependent antigen which can activate and recruit T-cells and thereby augment T-cell dependent antibody production. The carrier need not be strongly immunogenic by itself, although strongly immunogenic carriers are within the scope of this invention. Carriers in this context are generally polypeptides, which can be all or a fragment of a protein.

"Conjugated" generally refers to a chemical linkage, either covalent or non-covalent, usually covalent, that proximally associates the de-N-acetylated PS with the carrier so that the carrier-conjugated de-N-acetylated PS has increased immunogenicity relative to unconjugated de-N-acetylated PS.

The term "protective immunity" means that a vaccine or immunization schedule that is administered to a mammal induces an immune response that prevents, retards the development of, or reduces the severity of a disease that is caused by a pathogen (e.g., *Neisseria meningitidis*), or diminishes or altogether eliminates the symptoms of the disease. In the case of *N. meningitidis*, protective immunity can be predicted based on the ability of serum antibody to activate complement-mediated bactericidal activity (Goldschneider 1969 J Exp Med 129:1307-26) or confer passive protection against meningococcal bacteremia in a suitable animal challenge model (e.g., the infant rat model (Welsch et al 2003 J Infect Dis 188:1730)).

The phrase "a disease caused by a strain of group B of *Neisseria meningitidis*" encompasses any clinical symptom or combination of clinical symptoms that are present in an infection with a member of group B of *Neisseria meningitidis*. These symptoms include but are not limited to: colonization of the upper respiratory tract (e.g. mucosa of the nasopharynx and tonsils) by a pathogenic strain of group B of *Neisseria meningitidis*, penetration of the bacteria into the mucosa and the submucosal vascular bed, septicemia, septic shock, inflammation, haemmorrhagic skin lesions, activation of fibrinolysis and of blood coagulation, organ dysfunction such as kidney, lung, and cardiac failure, adrenal hemorrhaging and muscular infarction, capillary leakage, edema, peripheral limb ischemia, respiratory distress syndrome, pericarditis and meningitis.

The phrase "specifically binds to an antibody" or "specifically immunoreactive with", when referring to an antigen such as a polysaccharide, phospholipid, protein or peptide, refers to a binding reaction which is based on and/or is probative of the presence of the antigen in a sample which may also include a heterogeneous population of other molecules. Thus, under designated immunoassay conditions, the specified antibody or antibodies bind(s) to a particular antigen or antigens in a sample and does not bind in a significant amount to other molecules present in the sample. Specific binding to an antibody under such conditions may require an antibody or antiserum that is selected for its specificity for a particular antigen or antigens.

By "autoreactive" in the context of antibody binding is meant that the antibody binds to a host antigen (e.g., host polysialic acid (PSA)). Autoreactive antibodies include those that bind to host antigens as well as to foreign antigens (e.g., to NmB PS or *E. coli* K1 PS). A "non-autoreactive antibody" is an antibody that does not significantly or detectably bind to a host antigen, preferably does not detectably bind to a host antigen. Non-autoreactive antibodies of interest are antibodies that specifically bind NmB PS or *E. coli* K1 PS, which antibodies can also be, and preferably are, bactericidal for NmB and/or *E. coli* K1.

The phrase "in a sufficient amount to elicit an immune response" (e.g., to epitopes present in a preparation) means that there is a detectable difference between an immune response indicator measured before and after administration of a particular antigen preparation. Immune response indicators include but are not limited to: antibody titer or specificity, as detected by an assay such as enzyme-linked immunoassay (ELISA), bactericidal assay (e.g., to detect serum bactericidal antibodies), flow cytometry, immunoprecipitation, Ouchter-Lowry immunodiffusion; binding detection assays of, for example, spot, Western blot or antigen arrays; cytotoxicity assays, and the like.

The term "antibody" encompasses polyclonal and monoclonal antibody preparations, as well as preparations including hybrid antibodies, altered antibodies, $F(ab')_2$ fragments, F(ab) molecules, Fv fragments, single chain fragment variable displayed on phage (scFv), single domain antibodies, chimeric antibodies, humanized antibodies, and functional fragments thereof which exhibit immunological binding properties of the parent antibody molecule.

As used herein, the term "monoclonal antibody" refers to an antibody composition having a homogeneous antibody population. The term is not limited by the manner in which it is made. The term encompasses whole immunoglobulin molecules, as well as Fab molecules, $F(ab')_2$ fragments, Fv fragments, single chain fragment variable displayed on phage (scFv), and other molecules that exhibit immunological binding properties of the parent monoclonal antibody molecule. Methods of making polyclonal and monoclonal antibodies are known in the art and described more fully below.

An "antigen" is defined herein to include any substance that may be specifically bound by an antibody molecule. An "immunogen" is an antigen that is capable of initiating lymphocyte activation resulting in an antigen-specific immune response.

By "epitope" is meant a site on an antigen to which specific B cells and/or T cells respond. The term is also used interchangeably with "antigenic determinant" or "antigenic determinant site." B cell epitope sites on proteins, polysaccharides, or other biopolymers may be composed of moieties from different parts of the macromolecule that have been brought together by folding. Epitopes of this kind are referred to as conformational or discontinuous epitopes, since the site is composed of segments the polymer that are discontinuous in the linear sequence but are continuous in the folded conformation(s). Epitopes that are composed of single segments of biopolymers or other molecules are termed continuous or linear epitopes. T cell epitopes are generally restricted to linear peptides. Antibodies that recognize the same epitope can be identified in a simple immunoassay showing the ability of one antibody to block the binding of another antibody to a target antigen.

"Serogroup" or "Group" as used herein refers to classification of *Neisseria meningitides* by virtue of immunologically detectable variations in the capsular polysaccharide. About 12 serogroups are known: A, B, C, X, Y, Z, 29-E, W-135, H, I, K and L. Any one serogroup can encompass multiple serotypes and multiple serosubtypes.

"Serotype" as used herein refers to classification of *Neisseria meningitides* strains based on monoclonal antibody defined antigenic differences in the outer membrane protein Porin B. A single serotype can be found in multiple serogroups and multiple serosubtypes.

"Serosubtype" as used herein refers classification of *Neisseria meningitides* strains based on antibody defined antigenic variations on an outer membrane protein called Porin A, or upon VR typing of amino acid sequences deduced from DNA sequencing (Sacchi et al., 2000, *J. Infect. Dis.* 182: 1169; see also the Multi Locus Sequence Typing web site). Most variability between PorA proteins occurs in two (loops I and IV) of eight putative, surface exposed loops. The variable loops I and IV have been designated VR1 and VR2, respectively. A single serosubtype can be found in multiple serogroups and multiple serotypes.

By "isolated" is meant that a compound is separated from all or some of the components that accompany it in nature. "Isolated" can also refer to the state of a compound separated from all or some of the components that accompany it during manufacture (e.g., chemical synthesis).

By "purified" is meant a compound of interest has been separated from components that accompany it in nature. "Purified" can also be used to refer to a compound of interest separated from components that can accompany it during manufacture (e.g., in chemical synthesis). Typically, a compound is substantially pure when it is at least 50% to 60%, by weight, free from organic molecules with which it is naturally associated or with which it is associated during manufacture. Generally, the preparation is at least 75%, more preferably at least 90%, and most preferably at least 99%, by weight, of the compound of interest. A substantially pure compound can be obtained, for example, by extraction from a natural source (e.g., bacteria), by chemically synthesizing a compound, or by a combination of purification and chemical modification. A substantially pure compound can also be obtained by, for example, enriching a sample having a compound that binds an antibody of interest. Purity can be measured by any appropriate method, e.g., chromatography, mass spectroscopy, HPLC analysis, etc.

"Enriched" means that a substance (e.g., antibody or antigen) in a composition is manipulated by an experimentalist or a clinician so that it is present in at least a three-fold greater concentration by total weight, preferably at least 10-fold greater concentration, more preferably at least 100-fold greater concentration, and most preferably at least 1,000-fold greater concentration than the concentration of that antigen in the strain from which the antigen composition was obtained. Thus, for example, if the concentration of a particular antigen is 1 microgram per gram of total bacterial preparation (or of total bacterial protein), an enriched preparation would contain at least 3 micrograms per gram of total bacterial preparation (or of total bacterial protein).

The term "immunologically naïve with respect to a PS derivative" denotes an individual (e.g., a mammal such as a human patient) that has not been exposed to PS derivative of the invention, either alone or in the context of a larger molecule, in sufficient amounts to cause an immune response (e.g., to prime). If the individual has been exposed to a PS conjugate vaccine (in one or more doses), the individual has a propensity for production of protective antibodies and auto-reactive antibodies. (e.g., a PS conjugate vaccine) has a propensity for developing a mixture of protective and auto-reactive antibodies.

A "primed" subject refers to a subject that has been exposed (e.g., by administration) to an antigen (e.g., a de-N-acetylated PS of the invention) in a sufficient amount to elicit an immune response that, upon subsequent exposure to the same or second antigen (e.g., a PS conjugate), provides for a protective immune response, which response has no significant (e.g., clinically relevant) or detectable autoantibodies.

By "no clinically relevant autoantibody response" is meant that production of autoantibodies is reduced by at least 25%, at least 40%, at least 50%, at least 60%, at least 75%, at least 80% or more using the methods of the invention compared to autoantibody production following immunization of naïve subject with a conventional PS vaccine (e.g., a PS conjugate vaccine as described in U.S. Pat. No. 4,727,136 (N-Pr-NmB conjugate vaccine)).

"Pharmaceutically acceptable excipient" as used herein refers to any suitable substance which provides a pharmaceutically acceptable vehicle for administration of a compound(s) of interest to a subject. "Pharmaceutically acceptable excipient" can encompass substances referred to as pharmaceutically acceptable diluents, pharmaceutically acceptable additives and pharmaceutically acceptable carriers.

Polysaccharide Derivatives and Conjugates

As noted above, the invention is based on the discovery that the minimal epitope recognized by non-autoreactive, bactericidal anti-NmB group B capsular mAbs is a dimer of residues of sialic acid or sialic acid derivative, where the dimer contains at least one de-N-acetylated sialic acid residue adjacent an N-acylated (e.g., acetylated or propionylated) sialic acid residue or a sialic acid derivative residue. This dimeric epitope can be positioned within a de-N-acetylated PS derivative at the reducing end, the non-reducing end, or within the interior of the compound (e.g., 1, 2, 3, 4, 5, 10 or more residues from the reducing end or non-reducing end of the compound). The dimeric epitope can be present as one or more dimeric units within a de-N-acetylated PS derivative (e.g., as consecutive or nonconsecutive dimeric repeating units), or can be present within other units present in the de-N-acetylated PS derivative, e.g., within a trimeric unit, which may be present as consecutive or nonconsecutive repeating units). Exemplary molecules within the scope of the invention are set out in FIGS. 10-19, 20-22, and 23-37.

De-N-acetylated PS derivatives of the invention, and useful in the methods of the invention, generally comprise at least one dimeric epitope, which can be present in a completely de-N-acetylated polysaccharide or an at least partially de-N-acetylated polysaccharide, and can be present in a homopolymeric or heteropolymeric molecule. For example, a PS derivative of the invention can comprise one or more structures as set out below (see, e.g., Formulae I-VII below). PS derivatives can comprise 2, 3, 4, 5, 6, 7, 8, 9, 10, 11, 12, 13, 14, 15, 16, 17, 18, 19, 20, 25, 30, 35, 40, 45, 50, 55, 60 or more sialic acid residues or derivatives thereof, and may have a degree of polymerization (Dp) of about 2 to about 60, about 10 to about 50, about 30 to about 50, about 10 to 20, or about 12 to about 18, with a Dp of about 2 to about 10 being of particular interest. PS derivatives that are smaller in size can comprise further modifications (e.g., be conjugated to a carrier, lipidated, and the like) to provide molecules of suitable size and/or immunogenicity. PS derivatives of the invention can additionally comprise 3, 4, 5, 6, 7, 8, 9 or 10 or more adjacent de-N-acetylated residues, wherein in some embodiments, particularly where the PS derivative is composed of only N-acetylated and de-N-acetylated residues and is not further modified (e.g., by conjugation to a carrier or by modification of a sialic acid residue at the reducing end to contain a secondary alkyl amine), the de-N-acetylated residues of the PS derivative may be 30% or less of the total residues of the molecule, and N-acetylated residues may be about 70% or more of the total residues of the molecule.

De-N-acetylated PS derivatives of the invention, when administered to a subject elicit production of antibodies that bind a bacterium (e.g., an anti-NmB or anti-*E. coli* K1 response). Such antibodies, which can be bactericidal in the case of anti-NmB or anti-*E. coli* K1 antibodies, are not significantly or detectably autoreactive with PSA of the subject (e.g., human PSA).

In general, de-N-acetylated PS derivatives of the invention are at least partially de-N-acylated, so that the PS derivatives are zwitterionic compounds composed of polysaccharide residues or derivatives thereof, and comprise one or more dimers, and/or one or more trimers, which comprise an epitope as described above. The de-N-acetylated PS derivatives in general comprise at least one dimeric epitope, where the dimeric epitope is characterized by having (1) first and second de-N-acetylated residues; (2) a first N-acylated residue and a second adjacent de-N-acylated residue (i.e., a residue having a free amine group), where the N-acylated residue is not an N-propionyl (N-Pr) group; or (3) a first de-N-acylated residue (i.e., a residue having a free amine group) and a second adjacent N-acylated residue. In certain embodiments, the N-acylated residue comprises an unsaturated acyl group; in further embodiments, the N-acylated residue does not comprise an N-propionyl (N-Pr) group (i.e., the sialic acid residue in the dimer is not N-propionylated).

As used herein an "acyl group" includes a saturated or unsaturated acyl group, usually a saturated or unsaturated $C_{2-18}$ acyl group, a saturated or unsaturated $C_{2-16}$ acyl group, a saturated or unsaturated $C_{2-12}$ acyl group, a saturated or unsaturated $C_{2-10}$ acyl group, a saturated or unsaturated $C_{2-8}$ acyl group, a saturated or unsaturated $C_{2-6}$ acyl group, a saturated or unsaturated $C_{2-4}$ acyl group, or a saturated $C_{2-4}$ acyl group. A saturated acyl group as used herein is intended to refer to a carbonyl joined to a saturated alkyl group; an unsaturated acyl group as used herein is intended to refer to a carbonyl joined to an unsaturated alkyl group. In some embodiments, unsaturated acyl groups are of particular interest. The residues of the dimer can be a sialic acid or sialic acid derivative, such as a lactone or cyclic sialic acid.

Accordingly, the PS derivatives of the invention comprise one or more de-N-acetylated residues of a sialic acid moiety or derivative thereof (e.g., a lactone, cyclic sialic acid, and the like), which de-N-acetylated residues can be positioned within the PS derivative at the reducing end, the non-reducing end, or within the interior of the PS derivative (i.e., between the reducing and non-reducing ends), with PS derivatives having de-N-acetylated residues at the reducing end being of particular interest.

The de-N-acetylated PS derivatives of the invention may be provided as a structure comprising a single dimeric epitope, or a polymeric unit comprising two or more dimeric epitopes. De-N-acetylated PS derivatives may be homopolymeric or heteropolymeric structures, which can be composed of one or more of the structures below as well as, in some embodiments, additional de-N-acetylated or N-acetylated sialic acid residues. Where a formula is provided below with reference to "n" units (e.g., units of a dimeric or trimeric structure), the PS derivative can comprise multiple of such "n" units. For example, a PS derivative of the invention can comprise 2, 3, 4, 5, 6, 7, 8, 9 10 or more consecutive or non-consecutive units of a given dimeric or trimeric structure, where "n" refers to the number of consecutive dimeric or trimeric structures within each unit. Such dimeric and trimeric units can be separated by sialic residues.

The PS derivatives of the invention can further comprise additional moieties attached to a sialic acid residue or derivative thereof at the non reducing terminus, reducing-terminus or both the non-reducing- and reducing-termini of the polysaccharide polymer.

In one embodiment, de-N-acetylated PS derivatives of the invention include those comprising a structure represented by the formula:

FORMULA I

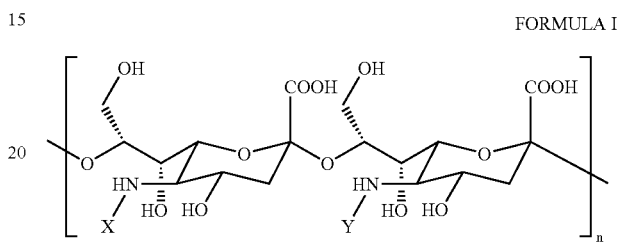

wherein

X and Y are independently H, an amine protecting group (e.g., a trihaloacyl group), or a saturated or unsaturated acyl group (usually a saturated acyl group), where in some embodiments, X and Y are independently 1) H or an amine protecting group; or 2) a saturated or unsaturated acyl group, and n is at least 1, 2, 3, 4, 5, 6, 7, 8, 9, 10, 11, 12, 13, 14, 15, 16, 17, 18, 19, 20, 25, 30, 35, 40, 45, 50, 55, 60 or more, usually 5 or greater, more usually about 10 or greater, and may have a degree of polymerization (Dp) of about 2 to about 60, about 10 to about 50, about 30 to about 50, about 10 to 20, or about 12 to about 18, with a Dp of about 2 to about 10 being of particular interest, and further wherein when X is a saturated or unsaturated acyl group (in some embodiments, other than a propionyl group and, in further embodiments, other than an unsaturated acyl group), Y is H or an amine protecting group; and when Y is a saturated or unsaturated acyl group (in some embodiments, other than a propionyl group and, in further embodiments, other than an unsaturated acyl group); X is H an amine protecting group. In another embodiment of particular interest, X and Y are independently H or a saturated or unsaturated acyl group, usually an unsaturated acyl group, In further embodiments, X and Y are independently an amine protecting group (e.g., a trihaloacyl group) or a saturated or unsaturated acyl group, usually a saturated acyl group. In some embodiments, particularly where X or Y is H or an unsaturated acyl group, the PS derivative is less than 90%, usually less than 85%, or less than 80% N-acylated, particularly where the PS derivative comprises at least 10 or 20 residues.

In an embodiment of interest, X in Formula I is a saturated acyl group and Y is H or an amine protecting group. In an embodiment of particular interest, X in Formula I is an acetyl group and Y is H or an amine protecting group (e.g., a trihaloacyl group (e.g., a trihaloacetyl group)). In another embodiment of interest, X in Formula I is a saturated acyl group and Y is H; or X is an acetyl group and Y is H.

Where either X or Y are an amine protecting group (e.g., a trihaloacyl group), such PS derivatives are referred to herein as "protected PS derivatives", where the amine protecting group acts to prevent the amine group from undergoing a reaction during further modification of the protected PS derivative, e.g., conjugation of the molecular to a carrier (e.g.,. a carrier protein), addition of a lipid moiety (e.g., addition of an acyl amine at a non-reducing end of the protected PS derivative), and the like. The amine protecting group can subsequently be modified to provide a free amine at the residue. Protected PS derivatives in general are exemplified by the structures described herein, where an amine protecting group is present at a variable position in lieu of a hydrogen. That is, where a hydrogen might be desired in a PS derivative to provide a free amine, protected PS derivatives contain an amine protecting group at that residue in lieu of the hydrogen of the free amine.

As used herein "amine protecting group" refers to a radical or group of atoms that is bound to an amine nitrogen atom of a molecule to prevent that nitrogen atom from participating in reactions occurring on other portions of the molecule. The term "amine-protected" denotes the structural characteristic of a molecule containing an amine nitrogen atom by which that nitrogen atom is prevented from participating in reactions occurring on other portions of the molecule.

Exemplary amine protecting groups for use in the invention include, but are not necessarily limited to, carbamates, amides, N-alkyl and N-aryl amines, imine derivatives, enamine derivatives, N-sulfonyls, and the like. Further exemplary amine protecting groups include, but are not necessarily limited to: acyl types such as formyl, trifluoroacetyl, phthalyl, and p-toluenesulfonyl; aromatic carbamate types such as benzyloxycarbonyl (Cbz) and substituted benzyloxy-carbonyls, 1-(p-biphenyl)-1-methylethoxy-carbonyl, and 9-fluorenylmethyloxycarbonyl (Fmoc); aliphatic carbamate types such as tert-butyloxycarbonyl (tBoc), ethoxycarbonyl, diisopropylmethoxycarbonyl, and allyloxycarbonyl; cyclic alkyl carbamate types such as cyclopentyloxycarbonyl and adamantyloxycarbonyl; alkyl types such as triphenylmethyl and benzyl; trialkylsilane such as trimethylsilane; and thiol containing types such as phenylthiocarbonyl and dithiasuccinoyl. Amine protecting groups and protected amine groups are described in, e.g., C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3.

Further exemplary amine protecting groups of particular interest include trihaloacyl groups, such as tribaloacetyl and tribalopropionyl groups (e.g., trichloroacetyl, trifluoroacetyl, trichloropriopionyl, trifluoropriopionyl), and the like, with trihaloacetyl groups being of interest.

In an embodiment of particular interest, the PS derivative comprising a structure of Formula I is conjugated to a carrier, e.g., by covalent attachment through a C2 ketone, a C6 aldehyde, C7 aldehyde, or C8 aldehyde as described below (e.g., C2-NH-carrier protein or C6-NH-carrier protein), where the carrier may be present at either the reducing or non-reducing end or both (e.g., through linkage to a residue at the reducing end of the derivative, to a residue at the non-reducing end of the derivative, or both). In another embodiment of particular interest, the PS derivative comprises at least one dimer of Formula I and comprises at the non-reducing end an N-acylated or de-N-acylated sialic acid residue substituted with an acyl amine (e.g., a saturated or unsaturated acyl amine, usually a saturated or unsaturated fatty acyl amine, usually a saturated acyl amine (e.g.,. $NHC_{2-18}$, $NHC_{2-12}$, $NHC_{2-10}$, $NHC_{2-8}$, $NHC_{4-12}$, and the like) (see, e.g., the moiety at the non-reducing end of Formulae IVa and IVb). These latter embodiments comprising a carrier and/or an acyl amine are of particular interest where the PS derivative comprises a structure of Formula I, wherein X is H and Y is an acetyl group, or where X is an acetyl group and Y is H. In another specific embodiment, where the PS derivative comprises a structure of Formula I, wherein X is H and Y is an acetyl group, or where X is an acetyl group and Y is H, the PS derivative is provided in combination with an adjuvant, as described below, where the PS derivative and adjuvant are preferably provided in a pharmaceutically acceptable carrier (dry or aqueous diluent).

In one embodiment, the dimer is a disaccharide, where the disaccharide comprises one or more residues in which the N-acetyl group on the C-5 amino group has been removed or, where one of the two residues are de-N-acetylated, the second residue contains an N-acetyl group (but in some embodiments not an N-propionyl group). The disaccharide unit defining this minimal epitope may be at the reducing end, the non-reducing end, or within the polysaccharide. Where the de-N-acetylated PS derivative is provided as a disaccharide, the composition can have the structure:

FORMULA II

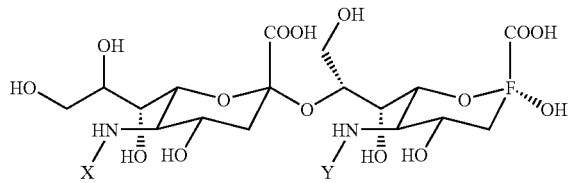

wherein X and Y are independently H, an amine protecting group (e.g., a trihaloacyl group), or a saturated or unsaturated acyl group; preferably further wherein when X is a acyl group (preferably other than a propionyl group), Y is H or an amine protecting group, and when Y is acyl group (preferably other than a propionyl group) X is H or an amine protecting group. In an embodiment of particular interest, X is an acetyl group and Y is H. Where X and/or Y are an amine protecting group, the compound is referred to herein as a protected PS derivative, where the protecting groups can be exploited as described above. Exemplary amine protecting groups are those described above. A PS derivative of Formula II can be further modified to include a carrier and/or an acyl amine, as described above for PS derivatives of Formula I, particularly where X is H and Y is an acetyl group; or where X is an acetyl group and Y is H.

De-N-acetylated PS derivatives of the invention also include those comprising a structure represented by the formula:

FORMULA III

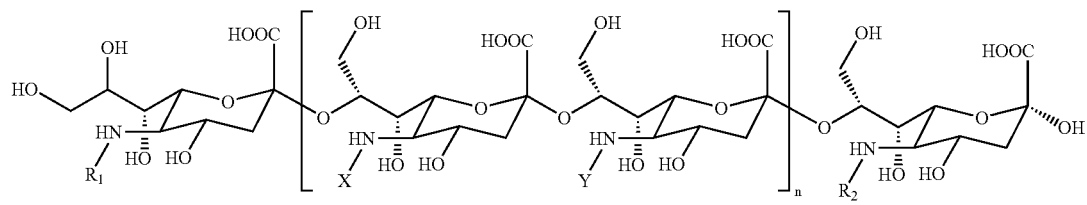

where X, Y, and n are as defined above, and $R_1$ and $R_2$ are independently H or an amine protecting group (e.g., a trihaloacyl group); or an acyl group (e.g., acetyl group) as described above. A PS derivative of Formula III can be further modified to include a carrier and/or an acyl amine, with modification of protected PS derivatives being of interest, as described above for PS derivatives of Formulae I and II, particularly where X is H and Y is an acetyl group and where X is an acetyl group and Y is H.

In another embodiment, the de-N-acetylated PS derivative comprises a structure represented by the formulae:

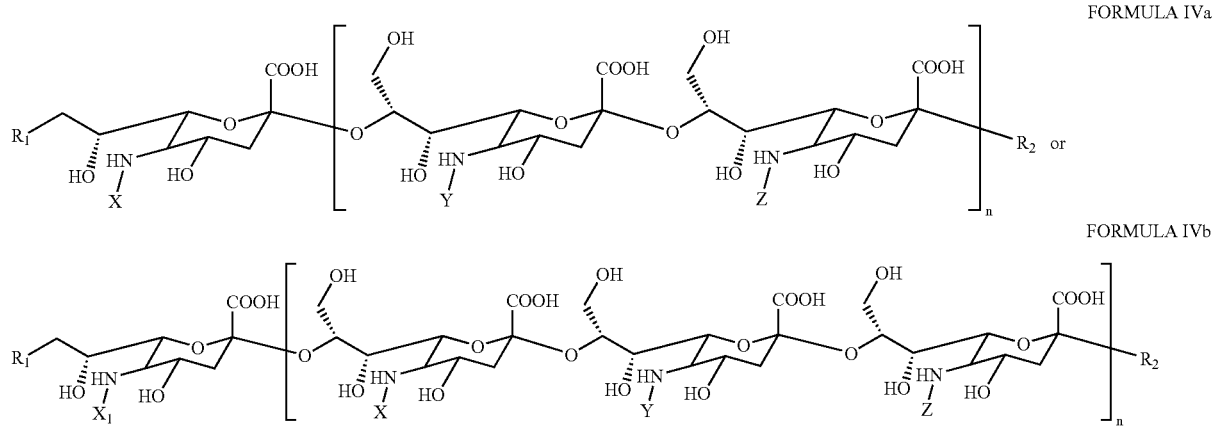

FORMULA IVa

FORMULA IVb wherein $X_1$, X, Y and Z are H, an amine protecting group (e.g., a trihaloacyl group), or a saturated or unsaturated acyl group, usually an unsaturated acyl group, usually wherein $X_1$, X, Y, and Z are 1) H or an amine protecting group, or 2) a saturated or unsaturated acyl group (usually a saturated acyl group); with the proviso that at least one of X, Y, and Z is H or an amine protecting group; and at least one of X, Y, and Z is a saturated or unsaturated (usually saturated) acyl group; with embodiments of particular interest being those in which at least one of X, Y, and Z is H or a an amine protecting group; at least one of X, Y, and Z is an acetyl group, and at least one of X, Y and Z is a propionyl group;

$R_2$ is a hydroxyl or one or more acylated, amine protected (i.e., having an amine protecting group, e.g., trihaloacylated), or de-N-acetylated sialic acid residues as described herein. In one embodiment, $R_2$ is a polymer of de-N-acetylated sialic acid residues and acylated sialic acid residues (usually a sialic acid residue having a saturated N-acyl group, e.g,. acetylated sialic acid residues, propionylated sialic acid residues, and the like).

In embodiments of particular interest, the PS derivatives of Formula IVa and IVb comprises at least one of each of a free amine (or an amine protecting group), an acetyl group, and a propionyl group. In this embodiment, the PS derivative can have the structure of Formula V, wherein when X is H, Y and Z are different acyl groups and are either an acetyl group or a propionyl group; when X is an acetyl group, Y and Z are different moieties and are either H (or an amine protecting group) or a propionyl group; and when X is a propionyl group, Y and Z are different moieties and are either H (or an amine protecting group) or an acetyl group. Exemplary embodiments are set out in FIGS. 23-37.

In another embodiment, the de-N-acetylated PS derivatives of the invention can be described as comprising at least one trimer having a structure represented by the formula:

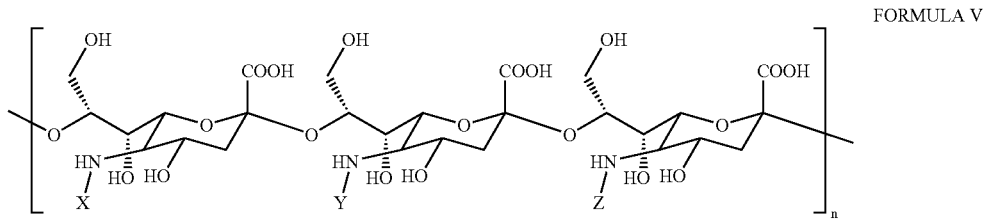

FORMULA V n is at least 1, 2, 3, 4, 5, 6, 7, 8, 9, 10, 11, 12, 13, 14, 15, 16, 17, 18, 19, 20, 25, 30, 35, 40, 45, 50, 55, 60 or more, usually 5 residues or greater, more usually about 10 residues or greater (e.g., having a degree of polymerization (Dp) of about 2 to about 60, about 10 to about 50, about 30 to about 50, about 10 to 20, or about 12 to about 18, with a Dp of about 2 to about 10 being of particular interest);

$R_1$ is a saturated or unsaturated acyl amine, usually a saturated or unsaturated fatty acyl amine, usually a saturated acyl amine (e.g.,. $NHC_{2-18}$, $NHC_{2-12}$, $NHC_{2-10}$, $NHC_{2-8}$, $NHC_{4-12}$, and the like); and wherein X, Y and Z are independently H, an amine protecting group (e.g., a trihaloacyl group), or a saturated or unsaturated acyl group (usually a saturated acyl group); usually where X, Y and Z are independently 1) H or an amine protecting group, or 2) a saturated or unsaturated acyl group, usually a saturated acyl group; with the proviso that at least one of X, Y, and Z is H or an amine protecting group; and at least one of X, Y, and Z is a saturated or unsaturated acyl group, usually a saturated acyl group; with embodiments of particular interest being those in which at least one of X, Y, and Z is H or an amine protecting group; at least one of X, Y, and Z is an acetyl group; and at least one of X, Y and Z is a propionyl group;

n is at least 1, 2, 3, 4, 5, 6, 7, 8, 9, 10, 11, 12, 13, 14, 15, 16, 17, 18, 19, 20, 25, 30, 35, 40, 45, 50, 55, 60 or more, usually about 4 residues or greater, more usually about 10 residues or greater (e.g., having a degree of polymerization (Dp) of about 2 to about 60, about 10 to about 50, about 30 to about 50, about 10 to 20, or about 12 to about 18, with a Dp of about 2 to about 10 being of particular interest).

In embodiments of particular interest, the PS derivative has a mixed acyl structure wherein each trimer comprises at least one of each of a free amine, an acetyl group, and a propionyl group. In this embodiment, the PS derivative has the structure of Formula V, wherein when X is H, Y and Z are different acyl groups and are either an acetyl group or a propionyl group; when X is an acetyl group, Y and Z are different moieties and are either H or a propionyl group; and when X is a propionyl group, Y and Z are different moieties and are either H or an acetyl group.

De-N-acetylated PS derivatives of the invention include acyl derivatives having saturated or unsaturated, usually saturated, alkyl groups of $C_1$-$C_4$, usually $C_1$-$C_3$, including, for example acetyl, propionyl, isopropyl, butionyl, and the like. De-N-acetylated PS derivatives further include mixed acyl derivatives containing one or more de-N-acylated sites, where the de-N-acetylated PS derivatives include different saturated or unsaturated, usually saturated, acyl groups.

De-N-acetylated PS derivatives of the invention further include those containing, a lactone moiety, a cyclic sialic acid moiety, or other sialic acid derivative in addition to or in lieu of one or more sialic acid moieties of a de-N-acetylated PS derivative described herein. For example, PS derivatives having a lactone moiety can comprise the structure:

FORMULA VI

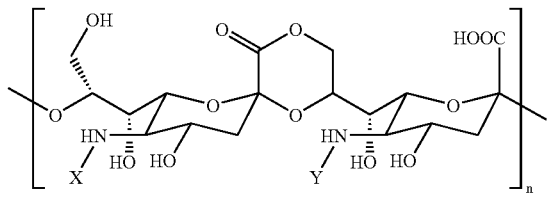

where X, Y and n are defined as above. PS derivatives having a lactone moiety can be present in a heteropolymer comprising one or more polymers (e.g,. dimers, trimers) having a structure as described herein.

In another example, the de-N-acetylated PS derivative comprises a cyclic imine and/or reduced to a cyclic secondary amine moiety (e.g.,. 1-(4-Hydroxy-5-hydroxymethyl-pyrrolidin-2-yl)-ethanone) in lieu of a sialic acid moiety can comprise the structure:

FORMULA VII

Figure 11:
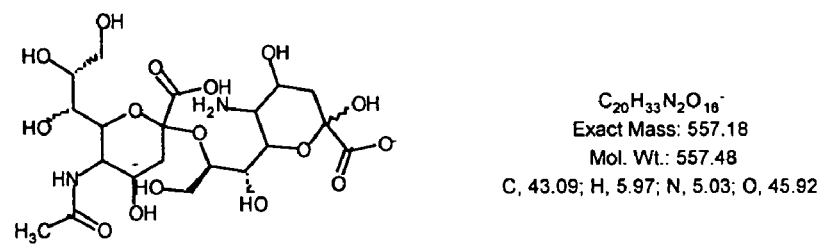
Figure 12:
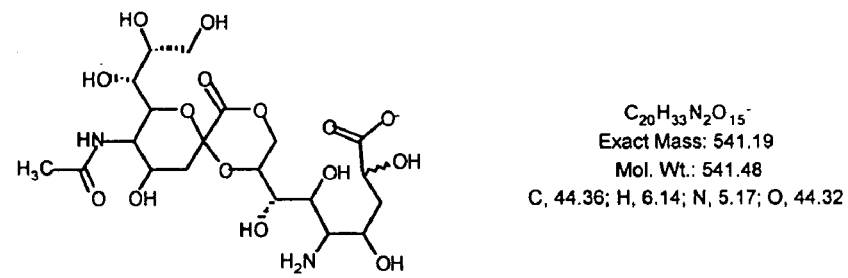
Figure 13:
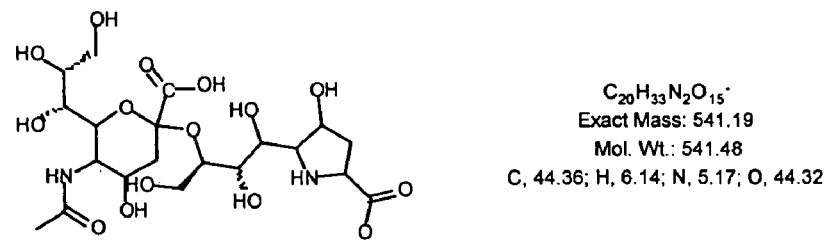
Figure 14:
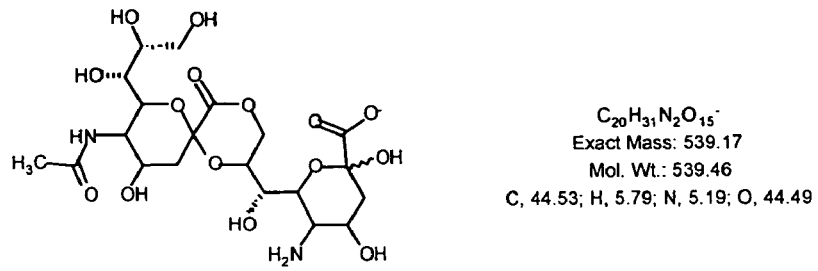
Figure 15:
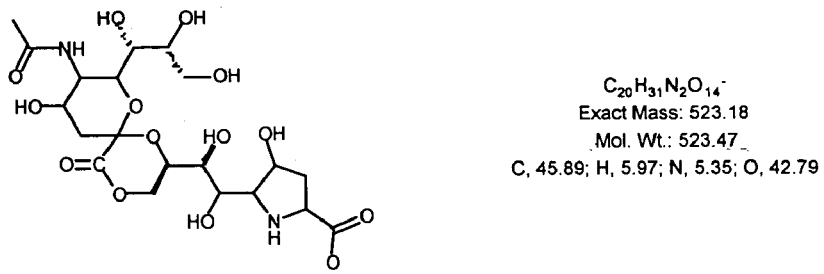
Figure 16:
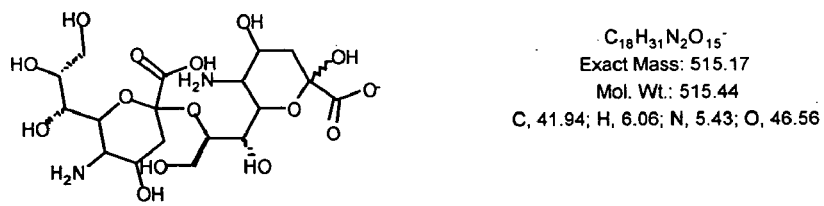
Figure 17:
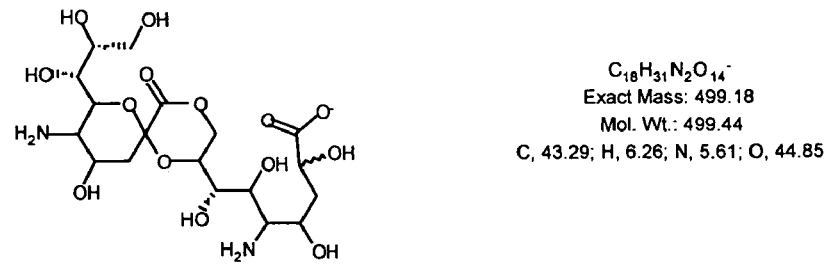
Figure 18:
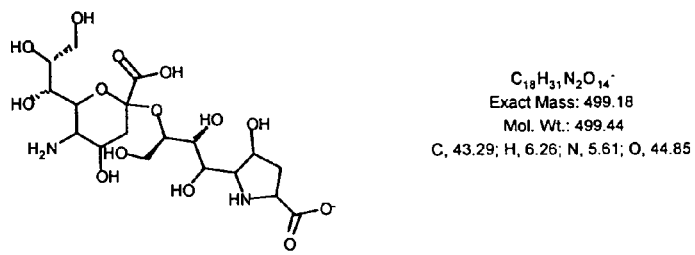
Figure 19:
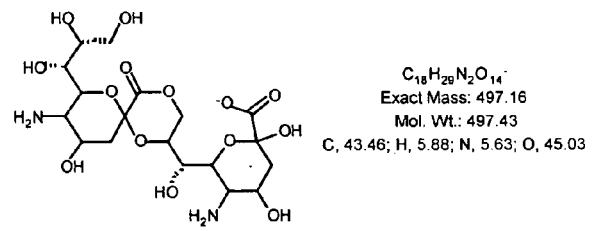

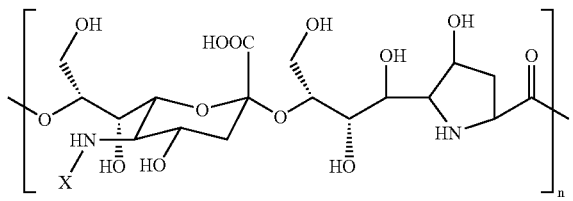

where X and n are defined as above. PS derivatives having a cycling imine or cyclic secondary amine moiety can be present in a heteropolymer comprising one or more polymers (e.g,. dimers, trimers) having a structure as described herein.

Where the de-N-acetylated PS derivative is provided as a single unit of the epitope (i.e., two residues as set out above, or three residues as described below), the de-N-acetylated PS derivative is normally covalently attached to a carrier (e.g., a protein carrier). In general, and particularly where the de-N-acetylated PS derivative is a disaccharide (e.g., as shown in FIG. 11), trisaccharide, or other molecule of 3 or fewer residues, the de-N-acetylated PS derivative can be coupled through the C2 ketone or, after periodate treatment, the C6 aldehyde by reductive amination to a carrier protein (e.g., C2-NH-carrier protein or C6-NH-carrier protein). In other embodiments, the amine is coupled to aldehydes at C7, C6, and/or C8 (see, e.g., FIGS. 20-22), which likely is a result of incomplete oxidation. Coupling to C7 is most common, with coupling to C6 and C8 being less common.

De-N-acetylated PS derivatives of the invention further include those having one or more residues having attached lipid moieties (such as in described in U.S. Pat. No. 6,638, 513). De-N-acetylated PS derivatives of the invention also include those having one or more residues having attached N-fatty acyl groups (e.g. N-lauroyl, N-oleoyl, and the like). Of particular interest are PS derivatives in which N-fatty acyl-containing residues constitute, for example, 50% of residues of the PS derivative or less such that the resulting PS derivatives are still soluble in water. De-N-acetylated PS derivatives of the invention also include those having one or more amidated sialic acid residues, which residues have an alkyl secondary amine, usually at a non-reducing end of the PS derivative. PS derivatives having one or more amidated sialic acid residues can be prepared by, for example, coupling fatty amines (e.g. dodecyl amine, oleoyl amine, and the like) to a C1 carboxyl group by nucleophilic substitution. Of particular interest are PS derivatives in which such C1 amide derivatives constitute, for example, about 50% of residues or less of the PS derivative. De-N-acetylated PS derivatives further include those conjugated to a carrier at either the reducing or non-reducing end or both (e.g., through linkage to a residue at the reducing end of the derivative, to a residue at the non-reducing end of the derivative, or both).

The de-N-acetylated PS derivatives of the invention can be homopolymers or heteropolymers of 2, 3, 4, 5, 6, 7, 8, 9, 10, 11, 12, 13, 14, 15, 16, 17, 18, 19, 20, 25, 30, 35, 40, 45, 50, 55, 60 or more dimeric epitope units (defining the minimal epitope) as described above, which dimeric units can be adjacent or separated by monomers or polymers of sialic acid residues or derivatives thereof. In some embodiments, the N-acylated residues of the de-N-acetylated PS derivative comprises represents less than 90%, less than 85%, less than 84%, less than 80%, less than 75%, less than 70%, less than 60%, or less than 55% of the total residues of the compound.

In other embodiments the ratio of de-N-acetylated residues to N-acylated residues is 1:1, 2:1, 3:1, 4:1, or 5:1 or more. In specific embodiments, the ratio of de-N-acetylated residues to N-acetylated residues is 1:1, 2:1, 3:1, 4:1, or 5:1 or more. In further specific embodiments, the ratio of de-N-acetylated residues to N-propionylated residues is 1:1, 2:1, 3:1, 4:1, or 5:1 or more. In other specific embodiments, the ratio of de-N-acetylated residues to N-alkylated residues is 1:1, 2:1, 3:1, 4:1, or 5:1 or more. In another specific embodiment, the ratio of de-N-acetylated residues to N-acetylated residues is 1:1, 2:1, 3:1, 4:1, or 5:1 or more.

De-N-acetylated PS derivatives of the invention can be provided as a composition that is homogenous or heterogenous with respect to the de-N-acetylated PS derivatives contained therein. For example, the invention contemplates compositions comprising de-N-acetylated PS derivatives that are homogenous or heterogenous with respect to one or more of dimeric epitope structure, position of the dimeric epitope within the de-N-acetylated PS derivative, presence or absence of a conjugated carrier protein, Dp, molecular weight, ratio of de-N-acylated to N-acylated residues, degree of N-acylation (e.g., degree of N-acetylation or N-propionylation), and the like.

It will be understood that the de-N-acetylated PS of the present invention may be modified to provide a variety of desired attributes, e.g. improved pharmacological characteristics, while increasing or at least retaining substantially all of the antigenicity or immunogenicity of the unmodified de-N-acetylated PS. For instance, the PS can be modified by extending, decreasing the number of residues in the polymer (e.g., so as to provide for differing degrees of polymerization (Dp)). By "Dp" is meant the number of residues of a polymer.

Substitutions with different residues, either naturally-occurring or non-naturally occurring, can also be made, e.g., as a result of chemical modification during de-N-acetylation, N-acylation, and the like. For example, the PS derivatives of the invention can be modified by a lipid moiety (as described in, for example, Examples 1 and 5 below, and in U.S. Pat. No. 6,638,513 (Seid)), conjugated to a carrier (e.g., at either the reducing or non-reducing end), and may comprise lactone, cyclic sialic acid, imine and reduced imine structures. In another example, the PS derivatives of the invention can be modified by attachment of an N-fatty acyl groups (e.g. N-laurolyl, N-oleoyl, and the like). In further example, the PS derivatives of the invention can include one or more sialic acid residue having an alkyl secondary amine (e.g., C1 amide derivatives), which can be prepared by, for example, coupling fatty amines (e.g. dodecyl amine, oleoyl amine, and the like) to a C1 keto group by nucleophilic substitution.

The de-N-acetylated PS employed in the subject invention need not be identical to those disclosed in the Examples section below, so long as the subject de-N-acetylated PS are able to induce an immune response in a host that provides for production of antibodies that selectively bind N. meningitidis capsular polysaccharide, with little or no significant binding to host antigens (e.g., to host polysialic acid (PSA)). Thus, one of skill will recognize that a number of derivatives (described in more detail below), can be made without substantially affecting the activity of the de-N-acetylated PS.

Methods of Making De-N-Acetylated PS Derivatives

In general, de-N-acetylated PS derivatives of the invention can be produced by de-N-acetylation of a PS of *N. meningitidis* or *E. coli* K1, or other suitable source of bacterial PS, followed by partial re-N-acylation. Partial re-N-acylation provides for production of a de-N-acetylated PS derivative having fewer than 90%, fewer than 85%, fewer than 84%, fewer than 80%, fewer than 75%, fewer than 70%, fewer than 60%, or fewer than 55%, usually about 10%, about 15%, about 16%, about 20%, about 25%, about 30%, about 40%, or about 45% N-acylated residues relative to the total residues of the compound. In this regard, the invention provides for control of the level of acylation of the final product, so as to provide a de-N-acetylated PS having a desired level of acylation. In general, reacylation is controlled or prevented by limiting the amount of acylating reagent.

The de-N-acetylated PS derivatives of the invention can be produced also by de-N-acetylation of a PS of *N. meningitidis* or *E. coli* K1, or other suitable source of bacterial PS, followed by re-N-acylation with a mixture of amine protected group and acyl groups (e.g., trihaloacetyl and acetyl groups) in a desired ratio such that the PS derivative contains fewer than 90%, fewer than 85%, fewer than 84%, fewer than 80%, fewer than 75%, fewer than 70%, fewer than 60%, fewer than 55% amine protected residues, usually about 10%, about 15%, about 16%, about 20%, about 25%, about 30%, about 40%, or about 45% amine protected residues (e.g., N-trihaloacylated residues) relative to the total residues of the compound (where the compound generally contains at least 10 or at least 20 residues). In this regard, the invention provides for control of the level of acylation of the final product after removal of the amine protecting group and avoiding undesirable side reactions with free amino groups, so as to provide a de-N-acetylated PS having a desired level of acylation. Removal of the amine protecting groups for a free amine at the deprotected residue. In general, the proportion of de-N-acetyl residues is controlled by limiting the amount of amine protecting reagent (e.g, the amount of a trihaloacylting reagent).

The de-N-acetylated PS derivatives of the invention can also be produced by biosynthesis of a PS of *N. meningitidis* or *E. coli* K1, or other suitable source of bacterial PS, in which the bacterial growth media is supplemented with a mixture of an amine-protected mannosamine (e.g., N-trihaloacyl mannosamine) and acyl mannosamine (e.g., N-trihaloacetyl and N-acetyl mannosame) in a desired ratio such that the PS derivative expressed by the bacteria contains fewer than 90%, fewer than 85%, fewer than 84%, fewer than 80%, fewer than 75%, fewer than 70%, fewer than 60%, or fewer than 55% amine-protected (e.g., N-trihalo acylated) residues relative to the total residues of the PS produced.

In this regard, the invention provides for control of the level of acylation of the final product after removal of the amine protecting group and avoiding undesirable side reactions with free amino groups, so as to provide a de-N-acetylated PS having a desired level of acylation. In general, the proportion of de-N-acetyl residues is controlled by limiting the amount of amine-protected mannosamine reagent (e.g., N-trihalo acetyl mannosamine).

PS, including NmB PS and *E. coli* K1, are exemplary molecules suitable for use in the PS derivatives and conjugates and other molecules in the invention, and such starting materials are known in the art, as are methods for their isolation and conjugation to a carrier.

The de-N-acetylated PS derivatives can be generated through any conventional means suitable. For example, in one embodiment, de-N-acetylation of a PS can be accomplished by contacting a native PS with a basic aqueous medium at elevated temperatures, for example about 90° C. to about 110° C., and at a pH of about 13 to about 14 (e.g., in sodium hydroxide about 2M concentration). Alternatively, hydrazine in aqueous solution may be used. The degree of N-deacetylation at this stage may vary, with at least about 85%, about 90%, about 95%, or about 99% up to about 100% de-N-acetylation being of interest. The de-N-acetylated product can be recovered by, for example, cooling, neutralizing, purification if desired, and lyophilization.

The non-aqueous and biosynthetic production methods are described in more detail below, as well as in the Examples.

Non-Aqueous Production Methods

In an embodiment of particular interest, the de-N-acetylated PS derivatives of the invention are produced in a polar protic organic solvent containing less than 5% water. The inventors have discovered that aqueous solution-based methods used to prepare NmB PS derivatives (as in, for example, Example 1) produce relatively small amounts of material that is reactive with protective non-autoreactive mAbs (e.g. SEAM 2,3). Without being held to theory, this low yield results from one or more of the failure to remove all N-acetyl groups as described above, the failure to quantitatively control the amount of re-N-acylation because of poor reactivity of the PS amino groups (intramolecular $COO^-$ and $NH_3^+$ charge pairing), competing hydrolysis of the acylating reagent, and/or oxidation of the amino group by periodate when preparing non-reducing end aldehydes.

The inventors have found that performing acylation of PS in a polar protic organic solvent, and, where desired, in the presence of a small amount of water (e.g., formamide, mixed formamide/2.5% water, and the like), protecting amino groups (e.g., with a trihaloacyl (e.g., trichloroacetyl or trifluoroacetyl)amide) which is later removed to generate predictable fractions of de-N-acetyl residues, and use of a strong base (e.g., sodium hydroxide or methoxide) during the acylation step to ensure amino group reactivity provides for improved yields and better control of the fraction of residues that a de-N-acetylated).

The organic solvent can be any suitable solvent, usually a polar protic or aprotic organic solvent. Exemplary such solvents include formamide, dimethylformamide, mixed formamide/dimethlformamide, and the like or mixtures of organic solvent and a small percent of water (typically at least about 2% or 2.5% water, but usually less than 10%, less than 5%). Water is added as necessary to ensure solubility of the components, particularly of the PS.

The amine groups of the molecule are protected by modifying them with a suitable amine protecting group. Exemplary amine protecting groups are described above, and include, without limitation, a carbamate or amide, including N-alkyl and N-aryl amines, imine derivatives, enamine derivatives, N-sulfonyl, and the like. In one embodiment of particular interest, the amine protecting groups is a trihaloacyl amide, usually trihaloacyl groups of $C_2$-$C_{12}$, more usually $C_2$-$C_{10}$, more usually $C_2$-$C_8$, more usually $C_2$-$C_6$, most usually a trihaloacetyl or trihalopropionyl, protecting group. Such protecting groups are preferably selected for stability at pH 8 or lower, stability in the presence of periodate, and ease of removal as described below. In general, amine protecting group prevents N-oxidation in the presence of periodate. The form of the PS derivative produced after this protecting step is referred to herein as the "protected PS derivative" or "protected acylated PS derivative", wherein the PS derivative comprises one or more amine protecting groups (e.g., trihaloacyl-protected amine groups).

In general, production of a protected PS derivative is accomplished by contacting an at least partially de-N-acetylated PS molecule with an amine protecting group reagent and an acylating reagent in the presence of an organic solvent as described above. The amine protecting reagent can be, for example, a trihaloacylating reagent, e.g., trihaloaccetic anhydride or alkyl trihaloacetic esters being of particular interest (e.g., trichloroacetic anhydride, trifluoroacetic anhydride, ethyl trifluoroacetyl ester, or ethyl trichloroacetyl ester, and the like). Acylating reagents provide an activated acyl group, wherein the activated acyl group is usually an acetyl group or propionyl group, more usually an acetyl group. Preferably, the trihaloacylating reagent and acylating reagents are contacted with the de-N-acetylated PS molecule as a mixture.

The relative amounts of trihaloacylating reagent and acylating reagent in the mixture are provided so that the end product of the protecting step contains the desired ratio of trihaloacylated residues and acylated residues on the PS derivative, wherein the trihaloacylated groups will generally be removed to provide a free amine in the final product. For example, where the ratio of free amines to acylated residues in the final de-N-acetylated PS derivative product is to be about 1:10, 1:4, or 1:1, the ratio of trihaloacylating reagent to acylating reagent is about is present in the mixture at a ratio of about 1:10, 1:4, or 1:1. Stated differently, the amount of trihaloacylating reagent in the mixture is roughly equal to the fraction of de-N-acetyl groups desired in the final de-N-acetylated PS derivative product after deprotection (e.g., 10%, 25%, 50%, and the like). The acylating reagent can also be provided as a mixture of different activated acyl groups (e.g., acetyl, propionyl) so as to provide for a desired ratio of differently acylated groups in the PS derivative. For example, where the PS derivative is to have a ratio of acetylated residues to propionylated residues of 2:1 or 11, the acylating agents for activated acetyl and propionyl groups is provided in the same or similar ratio in the acylating agent mixture.

After the protecting step, the protected PS derivative can then be modified as desired. For example, the protected PS derivative can be conjugated to a desired carrier, e.g,. by perioidiation followed by reductive amination. The protecting groups can then be removed (e.g. by hydrolysis or reduction) to leave a free amine, thus providing the final de-N-acetylated PS derivative product. The amine protecting groups can be removed by either hydrolysis using a strong aqueous base (e.g., pH 9 or greater), by reduction (e.g., with sodium borohydride), or by the amine added during the preparation of conjugates by reductive amination (see, e.g., Example 5). The PS derivative can then be isolated according to methods well known in the art.

The nonaqueous production methods have several advantages. First, performing the acylation reactions in an organic solvent provides greater flexibility in the type of acyl groups that can be used. For example, the use of an organic solvent facilitates use of fatty acyl groups of greater than 4 carbons which can pose challenges with respect to solubility in aqueous systems, as well as highly reactive activated acyl groups (e.g., trifluoroacetyl and trichloroacetyl). The reaction in organic solvent also provides greater control over the degree of acylation, since there is no or minimal competing reaction with water and OH$^-$ to deplete the reagent. As a result, the acylation reactions with the polysaccharide can be designed so that they proceed to completion.

The non-aqueous approach also allows the use of protected amine groups. When left unprotected, the polysaccharide amine groups may participate in other undesired reactions such as oxidation in the presence of periodate and intramolecular reactions with activated carboxyl groups, or with aldehydes introduced at the non-reducing end and the reducing end ketone. Trifluoroacetyl or trichloroacetyl are preferred protecting groups since they are stable at pH less than about 8, stable in the presence of periodate, and can easily be removed in aqueous base or by reduction with sodium borohydride to produce NmB PS derivatives containing de-N-acetyl residues where the percentage of de-N-acetyl residues is controlled by the amount of amine derivatized with protecting groups.

Biosynthetic Methods of PS Derivative Production

In another embodiment, PS derivatives are generated by culturing *N. meningitidis* bacteria, particularly Group B bacteria, in the presence of one or more N-acyl mannosamine derivatives and under conditions to promote production of PS derivatives having N-acyl sialic acid residues. This can be accomplished by including n the bacterial culture medium a mannosamine derivative having a desired N-acyl group.

In one embodiment, the N-acyl mannosamine derivative is a mannosamine comprising an amine protecting group (a "protected mannosarmine" or "amine protected mannosamine"), exemplified herein by N-trihaloacyl mannosamines, to accomplish "feeding of the mannosamine derivative to the bacteria. Exemplary amine protected mannosamines suitable for use in the invention include any amine protected mannosamine that can incorporated into the bacterium's PS synthetic pathway to provide for production of a protected PS derivative. Exemplary amine protected mannosamine reagents include N-trihaloacyl mannosamine, e.g., N-trihaloacetyl mannosamine (e.g., N-trichloroacetyl mannosamine, trifluoroacetyl mannosamine), N-formyl mannosamine, and the like). In addition to the amine-protected mannosamine, the culture medium generally also includes an N-acetyl mannosamine, to provide for a PS derivative having both protected sialic acid residues and N-acetylated sialic acid residues.

Without being held to theory, when cultured in the presence of the amine protected mannosamine, bacterial enzymes involved in capsule biosynthesis incorporate the amine protected mannosamine into sialic acid, which is then incorporated into capsule polysaccharide. Standard fermentation and purification methods can be used to generate a protected NmB PS derivative containing a desired fraction of monomers having attached protecting groups. The PS derivatives containing these protecting groups can be of the structures described above.

In a related embodiment, where a PS derivative having mixed N-acyl sialic acid residues is desired, the culture medium includes mixed N-acyl mannosamine reagents. For example, the N-acyl mannosamine can comprise saturated or unsaturated acyl groups, usually saturated acyl groups, of from $C_1$-$C_5$, more usually $C_2$-$C_5$, more usually $C_2$-$C_4$, more usually $C_2$-$C_3$, with acetyl or propionyl groups being of particular interest. Culturing the bacteria in the presence of such mixed N-acyl mannosamine reagents can provide for production of a PS derivative having mixed N-acyl sialic acid residues, e.g,. N-acetyl sialic acid, N-propionyl sialic acid, and the like. In one embodiment of particular interest, the bacteria is cultured in the presence of a mixture of a protected mannosamine (e.g., a N-trihaloacyl mannosamine) and N-acyl mannosamines (e.g,. a mixture of N-acetyl mannosamine and N-propionyl mannosamine).

In an embodiment of particular interest, a *N. meningitids* bacteria, preferably a Group B strain, is cultured in the presence of a mixture of an N-acyl mannosamine (e.g., N-acetyl mannosamine) and a N-trihaloacyl mannosamine. In embodiments of particular interest, the bacteria is a non-encapsulated strain, and can be a strain that is defective in PS capsule synthesis in the absence of supplemental N-acetyl mannosamine in the culture medium (e.g., due to a defect in one or more enzymes such that the bacteria cannot synthesize capsule PS unless the growth media is supplemented with N-acetyl mannosamine). For example, the strain can be defective in an N-acetyl-D-glucosamine-6-phosphate 2 epimerase, such as in the NmB strain M7.

The relative amounts of mannosamine reagents in the culture (e.g., the ratio of N-trihaloacyl mannosamine and N-acetyl mannosamine) are provided so that the biosynthetic end product contains the desired ratio of different sialic acid residues and/or derivatives in the PS derivative (e.g., trihaloacylated residues and acylated residues on the PS derivative). In general, the protecting groups (e.g,. the trihaloacylated groups) are removed to provide a free amine in the final PS derivative product. For example, where the ratio of free amines to acylated residues in the final de-N-acetylated PS derivative product is to be about 1:10, 1:4, or 1:1 the ratio of N-trihaloacyl mannosamine to mannosamine is about 1:10, 1:4, or 1:1. Stated differently, the amount of N-trihaloacyl mannosamine in the culture is roughly equal to the fraction of de-N-acetyl sialic acid groups desired in the final de-N-acetylated PS derivative product after deprotection (e.g., 10%, 25%, 50%, and the like).

Similarly, the relative amounts of "unprotected" N-acyl mannosamines (mannosamines that do not contain an amine protecting group, but which can comprise, for example, an acetyl or proprionyl group as the N-acyl group) in the culture can be provided so as to provide for a desired ratio of differently acylated sialic acid residues in the PS derivative. For example, where the PS derivative is to have a ratio of acetylated residues to propionylated residues of 2:1 or 1:1, N-acetyl mannosamine and N-propionyl mannosamine is provided in the same or similar ratio in the culture.

The PS derivatives can then isolated from the bacteria using methods known in the art. Where the PS derivative contains an amine protecting group, such PS derivatives are especially suitable for generating a PS derivative having further modification, e.g., a conjugate (e.g,. by periodate oxidation of the non-reducing end) or modifying a sialic acid residue to provide an alkyl secondary amine, particularly a C1 amide, at a non-reducing end of the PS derivative. After modification is completed, the trihaloacyl protecting groups can be removed as described above. For example, the protecting groups can be removed by reductive amination (e.g., with sodium cyanoborohydride) or further reduction (e.g., with sodium borohydride or treatment with base at pH 9 or greater) to provide a free amine.

Fragments, Re-acylation, and Other Modifications

Fragments of PS are usually produced as a result of N-deacetylation, which fragments generally have an average molecular weight ranging from about 3,000 to about 50,000 Daltons. While the invention contemplates use of full-length derivatives of PS as well as fragments, derivatives of PS fragments may be of particular interest.

Where desired, re-acylation to provide the de-N-acetylated PS derivatives of the invention can be carried out by resuspending the de-N-acetylated PS in an aqueous medium of about pH 8 to 9 (e.g., in sodium hydroxide), followed by addition of an appropriate acyl anhydride. In one embodiment, both the polysaccharide and acylating agent (e.g. acetyl anhydride or propionic anhydride) are provided in an organic solvent/water mixture (e.g., 2% (vol./vol.) water in formamide or dimethylformamide). This embodiment in particular provides for more controlled levels of reacylation. The method of the invention involves use of less than 1 molar equivalent, less than 0.75 mole equivalent, less than 0.5 mole equivalent, less than 0.25 mole equivalent, less than 0.1 mole equivalent, less than 0.05 mole equivalent, less than 0.025 mole equivalent, or as little as 0.02 mole equivalent of acid anhydride or acylating agent (e.g. acyl-active ester such as O-acyl hydroxysuccinimide).

O-acyl groups can be removed by increasing the pH to about 12. The pH is then lowered to about 8 (e.g., by addition of hydrochloric acid), and the derivative purified as desired, e.g., by dialysis. The reaction products can be further purified and lyophilized as desired.

The degree of N-acylation of the resulting de-N-acetylated PS derivatives is generally less than 90%, less than 85%, less than 84%, less than 80%, less than 75%, less than 70%, less than 60%, or less than 55%, usually greater than 10%, 15%, 16%, 25%, 30%, 40%, or 45%. The molecular weight of the de-N-acetylated PS derivatives can vary, with de-N-acetylated PS derivatives described herein ranging in molecular weight from about 0.5 kDa (e.g., a disaccharide) to 80 kDa, about 1 kDa to about 70 kDa, about 2 kDa to about 60 kDa, about 3 kDa to about 50 kDa, about 5 kDa to about 25 kDa, about 10 kDa to 80 kDa, about 20 kDa to 60 kDa, about 30 kDa to about 50 kDa, usually about 0.5 kDa to about 10 kDa.

De-N-Acetylated PS Conjugates

The de-N-acetylated PS or preferably, a protected amine PS can be conjugated to a carrier, so as to provide a de-N-acetylated PS-carrier complex. The conjugated PS-carrier complex can comprise multiple carrier molecules, multiple PS molecules, or both.

As noted above, the PS derivative of the conjugate can be provided as a dimer defining a minimal epitope as described above, or as a polymeric unit (e.g., two or more dimeric units defining the epitope described above). Where the PS derivative is a polymeric structure, the PS derivative can be homopolymeric or heteropolymeric. The composition can comprise additional residues attached at the non reducing terminus, reducing-terminus or both the non-reducing-andreducing-termini of a de-N-acetylated PS or preferably, a protected amine PS derivative.

In one embodiment, the carrier is a protein, a peptide, a T cell adjuvant or any other compound capable of enhancing the immune response. The protein may be selected from a group consisting of but not limited to viral, bacterial, parasitic, animal and fungal proteins. In one embodiment, the carrier is albumin. Alternatively, the carrier is tetanus toxoid, diphtheria toxoid, meningococcal outer membrane protein complexes (see, e.g., U.S. Pat. No. 4,707,543; U.S. Pat. No. 6,476,201; U.S. Pat. No. 6,558,677), or a bacterial outer protein (such as recombinant *N. meningitidis* porin B). Such carriers may be obtained from biochemical or pharmaceutical supply companies or prepared by standard methodology (Cruse, J M (ed.) Conjugate Vaccines in Contributions to Microbiology and Immunology vol. 10 (1989)). Synthetic peptides containing T-cell epitopes suitable for use as a carrier may include "universal" T cell epitope (Panina-Bordignon et al 1989 Eur J Immunol 19:2237) or non-natural Pan DR Epitope peptides (PADRE) (del Guercio et al 1997 Vaccine 15:441). Other agents, include other proteins, that can function as carriers would be known to those of ordinary skill in the art of immunology.

Exemplary methods for conjugation of the PS derivatives of the invention include, but are not necessarily limited to, the PS conjugated as described in U.S. Pat. Nos. 4,727,136; 5,811,102 (describing a group B meningococcal unsaturated $C_{3-5}$ N-acyl derivative polysaccharide conjugate); U.S. Pat. No. 5,969,130; and U.S. Pat. No. 6,080,589. For example, conjugation can be accomplished by introducing an aldehyde group at the non-reducing end, reducing end, or both of the de-N-acetylated PS derivative, for use in covalent attachment of one or more carrier proteins. Such can be accomplished through periodiation by contacting the PS or PS derivative with, for example, sodium meta periodate.

Where de-N-acetylated PS derivative comprises an underivatized amino group, certain restrictions may be imposed upon the procedures that can be used to couple the de-N-acetylated PS derivative to a carrier, such as a carrier protein. In this embodiment, the carrier is generally modified to contain one or more azide (hydrazide or adipic dihydrazide) groups through the reaction of hydrazide or adipic dihydrazide with the carrier protein activated at carboxyl groups with EDAC (see, e.g., U.S. Pat. No. 6,632,437). Since the pKa of the hydrazide amino group is about 2.5, and since hydrazides are strong nucleophiles, the imine conjugation reaction can be performed at pH of about 5.5-7.5 at which the primary amines on the carrier protein and the polysaccharide are substantially completely protonated and thus unreactive.

The PS derivative-protein conjugate vaccines are purified by size exclusion chromatography (ToyoPerl HW-45F). The protein concentration is determined by Lowry protein assay and the amount of conjugated polysaccharide by resorcinol assay (Svennerholm 1957 Biochim biophys Acta 24:604). To ensure that the protein and polysaccharide are covalently linked, the conjugate vaccines are resolved on SDS-PAGE and protein and polysaccharide are detected separately by Western blot using polyclonal anti-carrier protein antisera and anti-PS mAbs to detect the polysaccharide component.

In one example, where the de-N-acetylated PS derivative comprises dimeric epitopes, the de-N-acetylated PS derivative can be modified to provide for attachment to a carrier and have the following structure:

FORMULA VIII

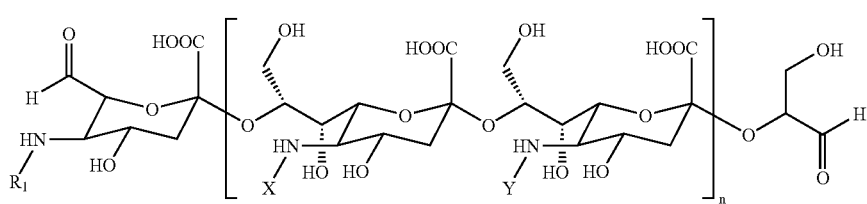

where X, Y, and are as defined above, and $R_1$ is H or an acyl group (e.g., an acetyl group). In other embodiments, R1 is selected independently from H; a saturated or unsaturated acyl group (e.g., a saturated or unsaturated $C_{2-18}$ acyl group, a saturated or unsaturated $C_{2-16}$ acyl group, a saturated or unsaturated $C_{2-12}$ acyl group, a saturated or unsaturated $C_{2-10}$ acyl group, a saturated or unsaturated $C_{2-8}$ acyl group, a saturated or unsaturated $C_{2-6}$ acyl group, a saturated or unsaturated $C_{2-4}$ acyl group, a saturated $C_{2-4}$ acyl group); an N-fatty acyl group (e.g. N-lauroyl, N-oleoyl, and the like); or a fatty amine (e.g. dodecyl amine, oleoyl amine, and the like). In one embodiment R1 is a $C_4$ to $C_8$ acyl group, such as n-butanoyl, isbutanoyl, n-pentanoyl, n-hexyanol, n-heptanoyl or n-octanoyl (as described in, for example U.S. Pat. No. 5,576,002), or an unsaturated $C_3$-$C_5$ acyl group, such as those described in U.S. Pat. No. 6,350,449.

In another embodiment where the de-N-acetylated PS derivative comprises trimeric repeats, the de-N-acetylated PS derivative can be modified to provide for attachment to a carrier and have the following structure:

FORMULA IX

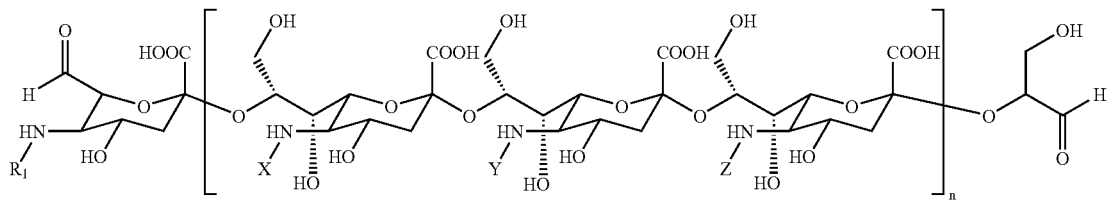

wherein

X, Y and Z are independently H or an amine protecting group; or a saturated or unsaturated acyl group (usually a saturated acyl group), with the proviso that at least one of X, Y, and Z is H or a trihaloacyl group; and at least one of X, Y, and Z is a saturated or unsaturated acyl group, usually a saturated acyl group, with embodiments of particular interest being those in which at least one of X, Y, and Z is H (or an amine protecting group), at least one of X, Y, and Z is an acetyl group, and at least one of X, Y and Z is a propionyl group;

n is at least 1, 2, 3, 4, 5, 6, 7, 8, 9, 10, 11, 12, 13, 14, 15, 16, 17, 18, 19, 20, 25, 30, 35, 40, 45, 50, 55, 60 or more, usually about 4 residues or greater, more usually about 10 residues or greater (e.g., having a degree of polymerization (Dp) of about 2 to about 60, about 10 to about 50, about 30 to about 50, about 10 to 20, or about 12 to about 18, with a Dp of about 2 to about 10 being of particular interest); and $R_1$ is H, an amine protecting group, or an acyl group (e.g., a saturated acyl group, such as an acetyl group). In other embodiments, $R_1$ is selected independently from H; an amine protecting group; a saturated or unsaturated acyl group (e.g., a saturated or unsaturated $C_{2-18}$ acyl group, a saturated or unsaturated $C_{2-16}$ acyl group, a saturated or unsaturated $C_{2-12}$ acyl group, a saturated or unsaturated $C_{2-10}$ acyl group, a saturated or unsaturated $C_{2-8}$ acyl group, a saturated or unsaturated $C_{2-6}$ acyl group, a saturated or unsaturated $C_{2-4}$ acyl group, a saturated $C_{2-4}$ acyl group); an N-fatty acyl group (e.g. N-lauroyl, N-oleoyl, and the like); or a fatty amine (e.g. dodecyl amine, oleoyl amine, and the like). In one embodiment R1 is a $C_4$ to $C_8$ acyl group, such as n-butanoyl, isbutanoyl, n-pentanoyl, n-hexyanol, n-heptanoyl or n-octanoyl (as described in, for example U.S. Pat. No. 5,576,002), or an unsaturated $C_3$-$C_5$ acyl group, such as those described in U.S. Pat. No. 6,350,449.

Immunogenicity of de-N-acetylated PS and de-N-acetylated PS Conjugates

The isolated de-N-acetylated PS, with or without further conjugation or in the presence or absence of a presentation structure, may be immunogenic or, alternatively, the immunogenicity may arise from the conjugation. Methods of measuring immunogenicity are well known to those in the art and primarily include measurement of serum antibody including measurement of concentration, avidity, and isotype distribution at various times after injection of the construct. Greater immunogenicity may be reflected by a higher titer and/or increased life span of the antibodies. Immunogenicity may be measured using in vitro bactericidal assays as well as by the ability of sera from immunized animals to confer passive protection to infection or disease in a suitable animal challenge model. Immunogenicity may be measured in the patient population to be treated or in a population that mimics the immune response of the patient population.

A particularly preferred means of determining the immunogenicity of a given substance is to first obtain sera of an animal (e.g., mouse) both before immunization, and after priming with de-N-acetylated PS and boosting with additional doses of de-N-acetylated PS conjugate. Following this, the strength of the post-immunization sera binding to de-N-acetylated PS is ascertained using an ELISA, and compared to the corresponding results with control mock-immunized animals.

The de-N-acetylated PS of the invention can prime for an immune response to a PS conjugate that both avoids autoantibodies and can provide for enhanced antibody response to PS conjugate, e.g., NmB PS conjugate, vaccine, compared to a response of an individual not primed with the de-N-acetylated PS and who has been vaccinated with the same PS conjugate Antigenic Composition Formulations "Antigen composition", "antigenic composition" or "immunogenic composition" is used herein as a matter of convenience to refer generically to compositions comprising a de-N-acetylated PS or conjugate of the invention. Compositions comprising a N-deacetylated NmB PS or NmB PS conjugate, or both, are of particular interest. Compositions useful for eliciting antibodies against NmB, E. coli K1, or cancer cells are contemplated by the present invention.

Compositions of the invention used as vaccines comprise an immunologically effective amount of antigen, as well as any other compatible components, as needed. By "immunologically effective amount" is meant that the administration of that amount to an individual, either in a single dose, as part of a series of the same or different antigenic compositions, is effective to elicit an antibody response effective for treatment or prevention of a symptom of, or disease caused by, for example, infection by Neisseria, particularly N. meningitidis, more particularly Group B N. meningitidis; or infection by E. coli K1. This amount varies depending upon the health and physical condition of the individual to be treated, age, the taxonomic group of individual to be treated (e.g., human, non-human primate, primate, etc.), the capacity of the individual's immune system to produce antibodies, the degree of protection desired, the formulation of the vaccine, the treating clinician's assessment of the medical situation, and other relevant factors. It is expected that the amount will fall in a relatively broad range that can be determined through routine trials. Dosage treatment may be a single dose schedule or a multiple dose schedule (e.g., including booster doses). The vaccine may be administered in conjunction with other immunoregulatory agents.

The compositions of the invention can be provided in a pharmaceutically acceptable excipient, which can be a solution such as an aqueous solution, often a saline solution, or they can be provided in powder form. The compositions of the invention can comprise a de-N-acetylated PS derivative of the invention and an adjuvant. Examples of known suitable adjuvants that can be used in humans include, but are not necessarily limited to, alum, aluminum phosphate, aluminum hydroxide, MF59 (4.3% w/v squalene, 0.5% w/v Tween 80, 0.5% w/v Span 85), CpG-containing nucleic acid (where the cytosine is unmethylated), QS21, MPL, 3DMPL, extracts from Aquilla, ISCOMS, LT/CT mutants, poly(D,L-lactide-co-glycolide) (PLG) microparticles, Quil A, interleukins, and the like. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogenic antigen.

Further exemplary adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing MTP-PE) formulated into submicron particles using a microfluidizer, (b) SAF, containing 10% Squalane, 0.4% Tween 80, 5% pluronic-blocked polymer L121, and thr-MDP either microfluidized into a submicron emulsion or vortexed to generate a larger particle size emulsion, and (c) RIBI™ adjuvant system (RAS), (Ribi Immunochem, Hamilton, Mont.) containing 2% Squalene, 0.2% Tween 80, and one or more bacterial cell wall components such as monophosphorylipid A (MPL), trehalose dimycolate (TDM), and cell wall skeleton (CWS), preferably MPL+CWS (Detox™); (2) saponin adjuvants, such as QS21 or Stimulon™ (Cambridge Bioscience, Worcester, Mass.) may be used or particles generated therefrom such as ISCOMs (immunostimulating complexes), which ISCOMS may be devoid of additional detergent e.g WO 00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454, optionally in the substantial absence of alum when used with pneumococcal saccharides e.g. WO 00/56358; (6) combinations of 3dMPL with, for example, QS21 and/or oil-in-water emulsions e.g. EP-A-0835318, EP-A-0735898, EP-A-0761231; (7) oligonucleotides comprising CpG motifs (Krieg *Vaccine* 2000, 19, 618-622; Krieg *Curr opin Mol Ther*2001 3:15-24; Roman et al., *Nat. Med,* 1997, 3, 849-854; Weiner et al., *PNAS USA,* 1997, 94, 10833-10837; Davis et al, *J. Immunol,* 1998, 160, 810-876; Chu et al., *J. Exp. Med,* 1997, 186, 1623-1631; Lipford et al, Ear. *J. Immunol.,* 1997, 27, 2340-2344; Moldoveami e/ al., *Vaccine,* 1988, 16, 1216-1224, Krieg et al., *Nature,* 1995, 374, 546-549; Klinman et al., *PNAS USA,* 1996, 93, 2879-2883; Ballas et al, *J. Immunol,* 1996, 157, 1840-1845; Cowdery et al, *J. Immunol,* 1996, 156, 4570-4575; Halpern et al, *Cell Immunol,* 1996, 167, 72-78; Yamamoto et al, *Jpn. J. Cancer Res.,* 1988, 79, 866-873; Stacey et al, *J. Immunol.,* 1996, 157,2116-2122; Messina et al, *J. Immunol,* 1991, 147, 1759-1764; Yi et al, *J. Immunol,* 1996, 157,4918-4925; Yi et al, *J. Immunol,* 1996, 157, 5394-5402; Yi et al, *J. Immunol,* 1998, 160, 4755-4761; and Yi et al, *J. Immunol,* 1998, 160, 5898-5906; International patent applications WO 96/02555, WO 98/16247, WO 98/18810, WO 98/40100, WO 98/55495, WO 98/37919 and WO 98/52581] i.e. containing at least one CG dinucleotide, where the cytosine is unmethylated; (8) a polyoxyethylene ether or a polyoxyethylene ester e.g WO 99/52549; (9) a polyoxyethylene sorbitan ester surfactant in combination with an octoxynol (WO 01/21207) or a polyoxyethylene alkyl ether or ester surfactant in combination with at least one additional non-ionic surfactant such as an octoxynol (WO 01/21152); (10) a saponin and an immunostimulatory oligonucleotide (e.g. a CpG oligonucleotide) (WO 00/62800); (11) an immunostimulant and a particle of metal salt e.g WO 00/23105; (12) a saponin and an oil-in-water emulsion e.g. WO 99/11241; (13) a saponin (e.g QS21)+3dMPL+IM2 (optionally+a sterol) e.g WO 98/57659; (14) other substances that act as immunostimulating agents to enhance the efficacy of the composition. Muramyl peptides include N-acetyl-muramyl-L-threonyl-D-isoglutamine (thr-MDP), N-25 acetyl-normuramyl-L-alanyl-D-isoglutamine (nor-MDP), N-acetylmuramyl-L-alanyl-D-isoglutarninyl-L-alanine-2-(1'-2'-dipalmitoyl-sn-glycero-3-hydroxyphosphoryloxy)-ethylamine MTP-PE), etc.

The antigen compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antigen in these formulations can vary widely, and will be selected primarily based on fluid volumes, viscosities, body weight and the like in accordance with the particular mode of administration selected and the patient's needs. The resulting compositions may be in the form of a solution, suspension, tablet, pill, capsule, powder, gel, cream, lotion, ointment, aerosol or the like.

The concentration of antigens of the invention in the pharmaceutical formulations can vary widely, i.e. from less than about 0.1%, usually at or at least about 2% to as much as 20% to 50% or more by weight, and will be selected primarily by fluid volumes, viscosities, etc., in accordance with the particular mode of administration selected.

Immunization

The de-N-acetylated PS and de-N-acetylated conjugates can be used alone or in combination with conventional PS derivatives and/or PS conjugates. When used in combination, the various compositions can be provided in the same or different formulations. Where administered in different formulations, the compositions can be administered at the same or different dosage regimen (e.g., by the same or different routes, at the same or different time (e.g., on the same or different days)), and the like). In general, administration of the de-N-acetylated PS and de-N-acetylated PS conjugates described herein can be performed serially, at the same time, or as a mixture, as described in more detail below. Preferably, administration is serial, with repeated doses of de-N-acetylated PS conjugate ad ministration. Exemplary immunization regimen are described below in more detail.

In general immunization is accomplished by administration by any suitable route, including administration of the composition orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

It is recognized that de-N-acetylated PS and related compounds described above, when administered orally, should be protected from digestion. This is typically accomplished either by complexing the de-N-acetylated PS or de-N-acetylated PS conjugate with a composition to render it resistant to acidic and enzymatic hydrolysis or by packaging in an appropriately resistant carrier such as a liposome. Means of protecting a compound of interest from digestion are well known in the art.

In order to enhance serum half-life, the antigenic preparations that are injected may also be encapsulated, introduced into the lumen of liposomes, prepared as a colloid, or other conventional techniques may be employed which provide an extended serum half-life of the peptides. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028. The preparations may also be provided in controlled release or slow-release forms for release and administration of the antigen preparations as a mixture or in serial fashion.

The compositions are administered to subject that is at risk from acquiring a Neisserial disease to prevent or at least partially arrest the development of disease and its complications. An amount adequate to accomplish this is defined as a "therapeutically effective dose." Amounts effective for therapeutic use will depend on, e.g., the antigen composition, the manner of administration, the weight and general state of health of the patient, and the judgment of the prescribing physician. Single or multiple doses of the antigen compositions may be administered depending on the dosage and frequency required and tolerated by the patient, and route of administration. In general, immunization is provided to as to elicit an immune response in the subject, where the invention can provide the advantage that immunization does not elicit detectable antibodies that significantly cross-react with polysialic acid in the subject, and can include production of antibodies bactericidal for N. meningitidis as well as for E. coli K1. Stated differently, immunization with the compositions of the invention elicits no clinically relevant autoantibody response directed against host sialic acid.

Immunization Regimen

The de-N-acetylated PS conjugates are administered to a host in a manner that provides for production of selective anti-PS antibodies, particularly anti-NmB PS antibodies, with little or no detectable host autoantibody production.

In particular embodiments, the antigen compositions described herein are administered serially. First, an immunogenically effective dose of a de-N-acetylated PS (which may be conjugated to a carrier, and may be with or without excipients) is administered to a subject. The first dose is generally administered in an amount effective to elicit an immune response (e.g., activation of B and/or T cells). Amounts for the initial immunization generally range from about 0.001 mg to about 1.0 mg per 70 kilogram patient, more commonly from about 0.001 mg to about 0.2 mg per 70 kilogram patient, usually about 0.005 mg to about 0.015 mg per 70 kilogram patient. Dosages from 0.001 up to about 10 mg per patient per day may be used, particularly when the antigen is administered to a secluded site and not into the blood stream, such as into a body cavity or into a lumen of an organ. Substantially higher dosages (e.g. 10 to 100 mg or more) are possible in oral, nasal, or topical administration.

After administration of the first antigen composition of de-N-acetylated PS, a therapeutically effective dose of a second antigen composition (e.g. de-N-acetylated PS, optionally conjugated and with or without excipients) is administered to the subject after the subject has been immunologically primed by exposure to the first dose. The booster may be administered days, weeks or months after the initial immunization, depending upon the patient's response and condition.

The existence of an immune response to the first antigen composition may be determined by known methods (e.g. by obtaining serum from the individual before and after the initial immunization, and demonstrating a change in the individual's immune status, for example an immunoprecipitation assay, or an ELISA, or a bactericidal assay, or a Western blot, or flow cytometric assay, or the like) and/or demonstrating that the magnitude of the immune response to the second injection is higher than that of control animals immunized for the first time with the composition of matter used for the second injection (e.g. immunological priming). Immunologic priming and/or the existence of an immune response to the first antigen composition may also be assumed by waiting for a period of time after the first immunization that, based on previous experience, is a sufficient time for an immune response and/or priming to have taken place—e.g. 2, 4, 6, 10 or 14 weeks. Boosting dosages of the second antigen composition are typically from about 0.001 mg to about 1.0 mg of antigen, depending on the nature of the immunogen and route of immunization.

In certain preferred embodiments, a therapeutically effective dose of a third antigen composition prepared from is administered to the subject after the individual has been primed and/or mounted an immune response to the second antigen composition. The third antigen compositions can be de-N-acetylated PS or de-N-acetylated PS conjugate. The third booster may be administered days, weeks or months after the second immunization, depending upon the subject's response and condition.

The existence of priming and/or an immune response to the second antigen composition may be determined by the same methods used to detect an immune response to the second antigen composition. The existence of priming and/or an immune response to the second antigen composition may also be assumed by waiting for a period of time after the second immunization that, based on previous experience, is a sufficient time for an immune response to have taken place—e.g. 2, 4, 6, 10 or 14 weeks. Boosting dosages of the second antigen composition are typically from about 0.001 mg to about 1.0 mg of antigen, depending on the nature of the immunogen and route of immunization.

The present invention further contemplates the use of a fourth, fifth, sixth or greater booster immunization, using either a fourth, fifth or sixth antigen composition.

In one embodiment, de-N-acetylated PS or de-N-acetylated PS conjugate is administered at least once, usually at least twice, and in some embodiments more than twice.

In one embodiment, de-N-acetylated PS derivative or de-N-acetylated PS derivative conjugate is administered as the first antigen composition so as to prime the immune response. Subsequent antigen compositions administered (e.g., the booster doses) can be de-N-acetylated PS derivative or de-N-acetylated PS derivative conjugate, or can be an antigenic composition that boosts the primed immune response to the first antigen composition, but which antigenic composition is not necessarily designed to avoid or mitigate an autoantibody response in the host. In this embodiment, antigen compositions administered after initial priming dose can be, for example, a vesicle preparation (e.g., an outer membrane vesicle and/or microvesicle preparation), a preparation of one or more isolated proteins of the bacteria of interest (e.g., a preparation comprising PorB of N. meningitidis), and the like. Without being held to theory, the initial priming dose of a de-N-acetylated PS derivative or conjugate thereof of the invention directs the immune response toward production of antibodies that are minimally cross-reactive with host antigen, and away from away from production of autoreactive antibodies. Once the host's immune response is primed in this manner, then exposure to antigens that might otherwise elicit an autoimmune response will not result in substantial production of autoantibodies, even where the booster dose(s) contains N-acetylated PS.

In one embodiment, the antigen compositions can be administered to a mammalian subject (e.g., human) that is immunologically naïve with respect to *Neisseria meningitidis* or *E. coli* K1. In a particular embodiment, the mammal is a human child about five years or younger, and preferably about two years old or younger, and the antigen compositions are administered at any one or more of the following times: two weeks, one month, 2, 3, 4, 5, 6, 7, 8, 9, 10, or 11 months, or one year or 15, 18, or 21 months after birth, or at 2, 3, 4, or 5 years of age.

In general, administration to any mammal is preferably initiated prior to the first sign of disease symptoms, or at the first sign of possible or actual exposure to infection or disease (e.g., due to exposure or infection by *Neisseria* or *E. coli* K1).

Specific Anti-PS Antibody-Based Diagnostics and Therapeutics

De-N-acetylated PS, as well as derivatives and conjugates thereof, as described herein can be used to generate antibodies, which antibodies can be used as reagents for use in diagnostic assays and in antibody-based therapy. Thus, in one aspect, the invention features a composition comprising antibodies that selectively bind *N. meningitidis* PS, particularly NmB PS; or *E. coli* K1 PS, with little or no detectable binding to host polysialic acid (that is, the antibodies are not significantly cross-reactive with host tissue). The anti-PS antibodies (particularly anti-NmB PS, anti-*E. coli* K1 PS, or anti-cancer cell antibodies) can be monoclonal or polyclonal, and can be provided with a suitable excipient. In some embodiments the anti-PS antibodies can be immobilized on a support, or provided in a container such as a vial, particularly a sterile vial, labeled for use in a diagnostic or therapeutic method as described in more detail below.

Diagnostics

Antibodies reactive with the de-N-acetylated PS can be used to detect *N. meningitidis* capsular polysaccharide (PS), or *E. coli* K1 PS in biological samples using immunodiagnostic techniques. In this context, the invention provides the advantage that such anti-de-N-acetylated PS antibodies provide for detection of the bacterial PS in a sample with little or no detectable binding to host-derived PSA, thereby reducing the incidence of false positive results. Suitable immunodiagnostic techniques include, but are not necessarily limited to, assays such as competition, direct reaction, or sandwich type assays. Such assays include Western blots; agglutination tests; enzyme-labeled and mediated immunoassays, such as ELISAs; biotin/avidin type assays; radioimmunoassays; immunoelectrophoresis; immunoprecipitation, and the like. The reactions generally include revealing labels such as fluorescent, chemiluminescent, radioactive, enzymatic labels or dye molecules, or other methods for detecting the formation of a complex between PS in the sample and the antibody or antibodies reacted therewith.

The aforementioned assays generally involve separation of unbound antibody in a liquid phase from a solid phase support to which PS-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a solid phase component (e.g., an anti-PS antibody) under suitable binding conditions such that the component is sufficiently immobilized to the support. Sometimes, immobilization to the support can be enhanced by first coupling the antibody to a protein with better binding properties, or that provides for immobilization of the antibody on the support with out significant loss of antibody binding activity or specificity. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind antibodies the support include polysaccharides, polylactic acids, polyglycolic acids, polymeric amino acids, amino acid copolymers, and the like. Such molecules and methods of coupling these molecules to the antigens, are well known to those of ordinary skill in the art. See, e.g., Brinkley, M. A. Bioconjugate Chem. (1992) 3:2-13; Hashida et al., J. Appl. Biochem. (1984) 6:56-63; and Anjaneyulu and Staros, International J. of Peptide and Protein Res. (1987) 30:117-124.

After reacting the solid support with the solid phase component, any non-immobilized solid-phase components are removed from the support by washing, and the support-bound component is then contacted with a biological sample suspected of containing ligand moieties (e.g., PS, particularly NmB PS or *E. coli* PS) under suitable binding conditions. After washing to remove any non-bound ligand, a secondary binder moiety is added under suitable binding conditions, wherein the secondary binder is capable of associating selectively with the bound ligand. The presence of the secondary binder can then be detected using techniques well known in the art.

More particularly, an ELISA method can be used, wherein the wells of a microtiter plate are coated with anti-de-N-acetyl PS antibody according to the present invention. A biological sample containing or suspected of containing PS (particularly NmB PS or *E. coli* K1 PS), is then added to the coated wells. After a period of incubation sufficient to allow antibody binding, the plate(s) can be washed to remove unbound moieties and a detectably labeled secondary binding molecule added. The secondary binding molecule is allowed to react with any captured antigen, the plate washed and the presence of the secondary binding molecule detected using methods well known in the art.

Thus, in one particular embodiment, the presence of bound PS from a biological sample can be readily detected using a secondary binder comprising an antibody directed against the antibody ligands. A number of anti-bovine immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the antibodies and PS form complexes under precipitating conditions. In one particular embodiment, the antibody can be attached to a solid phase particle (e.g., an agarose bead or the like) using coupling techniques known in the art, such as by direct chemical or indirect coupling. The antibody-coated particle is then contacted under suitable binding conditions with a biological sample suspected of containing PS to provide for formation of particle-antibody-PS complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

The above-described assay reagents, including the antibodies generated by immunization with the de-N-acetylated PS according to the methods described herein, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Passive Immunization and Other Antibody-based Therapies

In addition, antibodies generated using the methods of the invention to treat or prevent N. meningitidis-mediated or E. coli K1-mediated disease in mammalian subjects. Particularly; the antibodies generated using the de-N-acetylated PS or conjugates thereof according to the invention can be provided in a pharmaceutical composition suitable for administration to a subject, so as to provide for passive protection of the subject against N. meningitidis of E. coli K1 disease, or for treatment of cancer.

More particularly, immunoprotective antibodies generated according to the methods described herein and that recognize Neisserial PS or E. coli K1 epitopes can be administered to a subject (e.g. a human patient) to induce passive immunity against a Neisserial disease, either to prevent infection or disease from occurring, or as a therapy to improve the clinical outcome in patients with established disease (e.g. decreased complication rate such as shock, decreased mortality rate, or decreased morbidity, such as deafness). Where the antibodies are administered to effect a cancer therapy, the antibodies can optionally have attached a drug for targeting to the cancer cell to effect tumor killing or clearance, e.g., a toxin (e.g., ricin), radionuclide, and the like).

Antibodies administered to an organism other than the species in which they are raised are often immunogenic. Thus, for example, murine or porcine antibodies administered to a human often induce an immunologic response against the antibody. The immunogenic properties of the antibody are reduced by altering portions, or all, of the antibody into characteristically human sequences thereby producing chimeric or human antibodies, respectively.

Chimeric antibodies are immunoglobulin molecules comprising a human and non-human portion. More specifically, the antigen combining region (or variable region) of a humanized chimeric antibody is derived from a non-human source (e.g. murine), and the constant region of the chimeric antibody (which confers biological effector function to the immunoglobulin) is derived from a human source. The chimeric antibody preferably has the antigen binding specificity of the non-human antibody molecule and the effector function conferred by the human antibody molecule. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431 and 4,975,369). An alternative approach is the generation of humanized antibodies by linking the CDR regions of non-human antibodies to human constant regions by recombinant DNA techniques. See Queen et al., Proc. Natl. Acad. Sci. USA 86: 10029-10033 (1989) and WO 90/07861.

In one preferred embodiment, recombinant DNA vector is used to transfect a cell line that produces an antibody against a peptide of the invention. The novel recombinant DNA vector contains a "replacement gene" to replace all or a portion of the gene encoding the immunoglobulin constant region in the cell line (e.g. a replacement gene may encode all or a portion of a constant region of a human immunoglobulin, or a specific immunoglobulin class), and a "target sequence" which allows for targeted homologous recombination with immunoglobulin sequences within the antibody producing cell.

In another embodiment, a recombinant DNA vector is used to transfect a cell line that produces an antibody having a desired effector function (e.g. a constant region of a human immunoglobulin), in which case, the replacement gene contained in the recombinant vector may encode all or a portion of a region of an antibody and the target sequence contained in the recombinant vector allows for homologous recombination and targeted gene modification within the antibody producing cell. In either embodiment, when only a portion of the variable or constant region is replaced, the resulting chimeric antibody may define the same antigen and/or have the same effector function yet be altered or improved so that the chimeric antibody may demonstrate a greater antigen specificity, greater affinity binding constant, increased effector function, or increased secretion and production by the transfected antibody producing cell line, etc.

In another embodiment, this invention provides for fully human antibodies. Human antibodies consist entirely of characteristically human polypeptide: sequences. The human antibodies of this invention can be produced by a wide variety of methods (see, e.g., Larrick et al., U.S. Pat. No. 5,001,065). In one embodiment, the human antibodies of the present invention are produced initially in trioma cells (descended from three cells, two human and one mouse). Genes encoding the antibodies are then cloned and expressed in other cells, particularly non-human mammalian cells. The general approach for producing human antibodies by trioma technology has been described by Ostberg et al. (1983), *Hybridoma* 2: 361-367, Ostberg, U.S. Pat. No. 4,634,664, and Engelman et al., U.S. Pat. No. 4,634,666. Triomas have been found to produce antibody more stably than ordinary hybridomas made from human cells.

Methods for producing and formulation antibodies suitable for administration to a subject (e.g., a human subject) are well known in the art. For example, antibodies can be provided in a pharmaceutical composition comprising an effective amount of an antibody and a pharmaceutical excipients (e.g., saline). The pharmaceutical composition may optionally include other additives (e.g., buffers, stabilizers, preservatives, and the like). An effective amount of antibody is generally an amount effective to provide for protection against Neisserial disease, or E. coli K1 disease, or symptoms for a desired period, e.g., a period of at least about 2 days to 10 days or 1 month to 2 months).

Methods for Identification of Epitopes of Polysialic Acid

The invention also features methods for identifying a polysialic acid (PSA) epitope bound by an antibody. In general such methods involve contacting a PS derivative (also referred to herein as PSA derivatives) with an antibody under conditions suitable for formation of antigen-antibody complexes of the antibody and the PS derivative. The antigen-antibody complex is then contacted with an appropriate enzyme (e.g., a sialidase, e.g., an endo- or exo-sialidase, with use of neuraminidase being of particular interest) to facilitate removal of neuraminidase enzyme-accessible PSA derivative residues of the antigen-antibody complex. PSA derivative residues remaining in the antigen-antibody complex following sialidase enzyme treatment thus define an epitope bound by the antibody. The resulting antigen-antibody complex can be subjected to analysis to determine the epitope bound by the antibody. Such analysis can involve purification of the antigen-antibody complex, followed mass spectroscopy (e.g., MALDI-TOF).

In some embodiments the method involves screening a plurality of PS derivatives (e.g., a library of different PS derivatives) to facilitate identification of a PS derivative having an epitope bound by an antibody of interest. For example, the antibody can be an anti-PS specific antibody, which minimally or does not detectably cross-react with host PSA.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1

Preparation of N-Acyl NmB PS and Derivatives

N-acyl NmB PS (acyl=acetyl [Ac] or propionyl [Pr]) was prepared by the method of Guo and Jennings, with differences as noted below (Guo, Z. and Jennings, H. in 2001. N-Propionylation. In Meningococcal Vaccines: Methods and Protocols. A. J. Pollard, and C. J. M. Maiden, eds. Humana Press Inc., Totowa, N.J., p. 55.) as follows to produce PS derivatives of the present invention. Colominic acid or NmB PS (231 mg; Sigma-Aldrich Chemical Co., St. Louis, Mo.) and 20 mg of sodium borohydride (Sigma-Aldrich) was dissolved in 10 ml of 2M NaOH and heated to 100° C. in a sealed tube (Pierce Chemical Co., Rockford, Ill.) for 6 h.

The conditions of the de-N-acetylation reaction differ from those described by Guo and Jennings. Instead of producing a completely de-N-acetylated PS derivative as described by Guo and Jennings, the product typically contained 20% N-acetyl residues as determined by resorcinol assay described below. FIG. 1 provides the structure of an exemplary de-N-acetylated PS. The approach described herein has advantages for preparing PS derivatives containing a mixture of N-acetyl and N-acyl residues (e.g. N-propionyl, N-butanoyl, etc.), as well as for preparing PS derivatives containing a mixture of N-acetylated and de-N-acetylated residues, since it ensures that a minimum of 20% of the residues were N-acetylated. Also, the addition of sodium borohydride reduces the ketone at the reducing end of the PS to an alcohol and also, an imine that could be formed between the de-N-acetylated amino group and the C2 ketone of the reducing end residue to a secondary amine. NmB PS derivatives containing residues with N-acetyl groups, de-N-acetyl sites, and a cyclic secondary amine at the reducing end residue were bound by non-autoreactive, anti-NmB PS mAbs ("SEAM" mAbs, FIG. 2) (see Example 3, below) and, therefore, are important antigens for eliciting protective, non-autoreactive anti-NmB capsular antibodies.

After cooling the solution to ambient temperature, the solution was adjusted to pH 8.0 with 2 M HCl, dialyzed against water, and lyophilized. The PS was resuspended in 2 ml of 0.1×PBS (0.1 mM $KH_2PO_4$, 1 mM $Na_2HPO_4$, 13.7 mM NaCl, 0.27 mM KCl, pH 7.0), centrifuged (5000×g) for 10 min. to remove precipitated material. In contrast to the Guo and Jennings methods, the resuspended PS was loaded on to a 1.5 cm×25 cm column of Toyoperl HW-55F (Supelco, Belefonte, Pa.) equilibrated with 0.1×PBS. Fractions eluting with an apparent mass greater than 10 kDa were combined and lyophilized. The HW-55F column was calibrated using blue dextran, bovine serum albumin, ovalbumin, carbonic anhydrase, and the trinitrophenyl derivative of adipic acid dihydrazide as standards (Sigma-Aldrich).

Free amino groups were acylated by resuspending the PS (~100 mg) in 5 ml of 0.1 M NaOH and adding 0.2 ml of acyl anhydride (e.g., acetic acid anhydride or propionic acid anhydride) in 5 aliquots with stirring over several hours. (Acetic anhydride was not included in the derivatives previously prepared by Guo and Jennings.) The pH of the solution was maintained at ~8-9 by adding 2 M NaOH as required. The solution pH was raised to ~12 for 1 h to remove O-acyl groups, then lowered to pH 8 using 2 M HCl, the solution was dialyzed, lyophilized and the product purified and lyophilized as described above.

Although most of the amino groups were acylated in this procedure (≧90%), some amino groups were not derivatized and remain free amino groups. The efficiency of acylation depends on the solubility of the acid anhydride in water. Therefore, acylation with propionic anhydride, which is less soluble in water than acetic anhydride, will result in a greater amount of free amino groups than acetic anhydride. PS containing residues with de-N-acetyl sites was bound by the SEAM mAbs (see Example 3, below) and is, therefore, is an important determinant for eliciting protective, non-autoreactive anti-NmB capsular antibodies.

Smaller fragments of the PS (average degree of polymerization [Dp] 30) were produced by acid treatment. A portion of the N-acyl NmB PS (20 mg) was dissolved in 5 ml of 0.2 M NaOAc, pH 5.1 and heated to 70° C. in a sealed tube for 30 min. The solution was dialyzed, lyophilized, purified and lyophilized again as described above.

In addition to producing PS having a Dp that is on average smaller than that of the starting PS, acid treatment results in the formation of lactones between the C1 carboxyl group and the C9 OH group of the preceding residue (FIG. 3). PS containing small amounts of lactone may occur in NmB bacterial capsule but is unlikely to occur in human polysialic acid. The presence of small amounts of lactone in NmB PS may be important for eliciting protective, non-autoreactive anti-NmB capsular antibodies.

Aldehyde groups were introduced into the non-reducing and reducing ends of the PS for use in covalent attachment to a carrier protein. The PS (20 mg) was dissolved in 1 ml of 0.1 M NaOAc buffer, pH 6.5. Sodium meta periodate (5 mg, Sigma-Aldrich) was added and the solution kept in the dark for 30 min. The remaining $NaIO_4$ was degraded by adding 0.1 ml of 10% (wt/vol) ethylene glycol in water and left for 30 min. This procedure produces aldehyde groups at C8 and/or C7 of the non-reducing end terminal residue and, for PS that contains a reducing end terminal residue in which the C2 ketone was reduced to an alcohol during deacetylation (see above), an aldehyde group on C6 (FIG. 4).

Preparation of Dodecylamine and Protein-PS Derivative Conjugates. Dodecylamine derivatives were prepared by combining 20 milligrams of NmB PS derivative containing non-reducing end or reducing end aldehydes or ketones with 10 milligrams of dodecylamine in 5 milliliters of water. After heating the mixture to about 50 degrees C. for 30 minutes with stirring, 5 mg of sodium cyanoborohydride was added. The mixture was stirred at ambient temperature for 24 hours then dialyzed in water for 3 to 5 days to remove excess dodecylamine.

The reactivity of the dodecylamine derivatives with SEAM mAbs was determined by direct binding ELISA in which the antigen (i,e. the dodecylamine PS derivative) was absorbed to the surface of a microtiter plate by incubating a solution of the antigen in PBS buffer in the well of a microtiter plate overnight at 4 degrees C. The plates were washed with PBS buffer (5×) and blocked with PBS buffer containing 1% (weight/weight) of bovine serum albumin (Sigma; blocking buffer) for 1 hour at ambient temperature. The antibodies were diluted in blocking buffer and added to the plate (100 microliters per well). After incubating the plate for 4 hours at ambient temperature, the plates were washed with PBS buffer (5×) and rabbit anti-mouse-alkaline phosphatase conjugate antibody (Zymed) diluted in blocking buffer was added. After incubating an additional hour, the plates were washed (5×)

with PBS buffer and the bound antibody was detected by adding p-nitrophenyl phosphate substrate in 50 mM sodium carbonate buffer, pH 9, containing 1 mM $MgCl_2$. The absorbance at 405 nm after 30 minutes incubation at ambient temperature was measured using a BioRad Model microtiter plate reader. The results of binding experiments are shown in FIG. 38.

PS derivatives conjugated to a carrier protein were prepared by combining 10 milligrams of bovine serum albumin (BSA, Pierce Chemical Co.) with 20 mg of PS derivative or PS derivative containing a non-reducing end aldehyde group in PBS buffer. 5 milligrams of sodium cyanoborohydride was added and the mixture was stirred in the dark for 5 days. The solution was dialyzed (10-14 kDa cutoff membrane) in PBS buffer. The reactivity of the PS derivative-BSA conjugates with mAbs was determined by direct binding ELISA as described in the previous paragraph. The results of binding experiments are shown in FIG. 39.

The concentration of sialic acid and de-N-acetyl sialic acid in NmB PS derivative stock solutions was determined by the Svennerholm resorcinol reaction (Svennerholm, L. (1957) Biochim. Biophys. Acta 24:604) modified as follows. Resorcinol working reagent was prepared by combining 9.75 milliliters of water, 0.25 milliliters of 0.1 M $CuSO_4.5H_2O$, 10 milliliters of 20 milligram per milliliter solution of resorcinol in water, and 80 milliliters of concentrated HCl. The resorcinol working reagent (300 microliters) was combined with the sialic acid or de-N-acetyl sialic acid sample solution (up to 50 micrograms of sialic acid) or standard stock solution in water (300 microliters) in a polypropylene deep well (2 milliliter) microtiter plate. The plate was sealed with a plate cover and heated in a boiling water bath for 30 minutes. After cooling to ambient temperature, isoamyl alcohol (600 microliters) was added and mixed using a pipette. The phases were allowed to separate and the upper isoamyl alcohol layer was removed to a clean microtiter plate. 250 microliters of the isoamyl alcohol extract and the lower aqueous solution were transferred separately to a polystyrene microtiter plate and the absorbance at 495 nm and 580 nm was measured.

The amount of N-acetyl sialic acid was determined by from the absorbance of the isoamyl alcohol fraction at 580 nm and the amount of de-N-acetyl sialic acid was determined from the absorbance of the aqueous fraction at 495 nm in comparison to a standard curve for each. The amount of de-N-acetyl sialic acid was corrected for the amount of de-N-acetylation that occurs during the acid hydrolysis step of the assay by measuring the amount of de-N-acetylation that occurs in the sialic acid standard.

Reverse-Phase HPLC purification of NmB PS derivatives containing long chain alkyl groups. NmB PS derivatives containing long chain (i.e. $\geq$C8) alkyl groups (e.g. dodecylamine derivatives) were separated by reverse-phase HPLC using a Poros R1/H column and BioCAD Perfusion Chromatography Workstation. Derivatives were eluted with a gradient from 0% to 80% acetonitrile in 20 mM ammonium acetate buffer, pH 6.5 over 30 minutes at a flow rate of 5 milliliters per minute. Fractions (1 milliliter each) were collected.

Fractions containing derivatives that were reactive with mAbs (for example SEAM 3, SEAM 12 Granoff et al. 1998, supra) were determined by adding 100 microliters of each fraction to a well of a 96 well microtiter plate (Immulon II, Dynatech) and incubating the plate at 4 degrees C. overnight. The plates were washed with PBS buffer (5×) and blocked with PBS buffer containing 1% (weight/weight) of bovine serum albumin (Sigma; blocking buffer) for 1 hour at ambient temperature. The antibodies were diluted in blocking buffer and added to the plate (100 microliters per well). After incubating the plate for 4 hours at ambient temperature, the plates were washed with PBS buffer (5×) and rabbit anti-mouse-alkaline phosphatase conjugate antibody (Zymed) diluted in blocking buffer was added. After incubating an additional hour, the plates were washed (5×) with PBS buffer and the bound antibody was detected by adding p-nitrophenyl phosphate substrate in 50 mM sodium carbonate buffer, pH 9, containing 1 mM $MgCl_2$. The absorbance at 405 nm after 30 minutes incubation at ambient temperature was measured using a BioRad Model microtiter plate reader.

Figure 20:
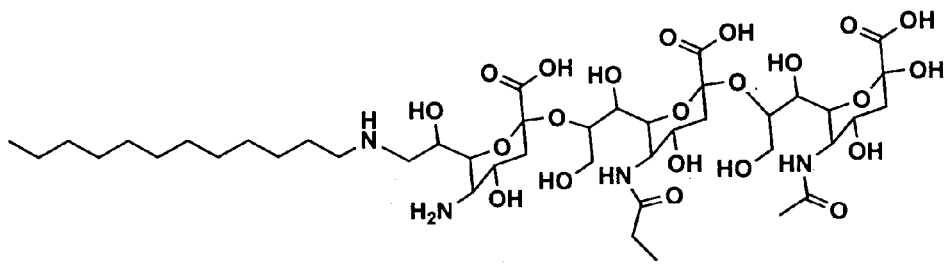
FIGS. 20-22 provide structures of dodecylamine NmB PS derivatives prepared and identified in EXAMPLE 1.
Figure 21:
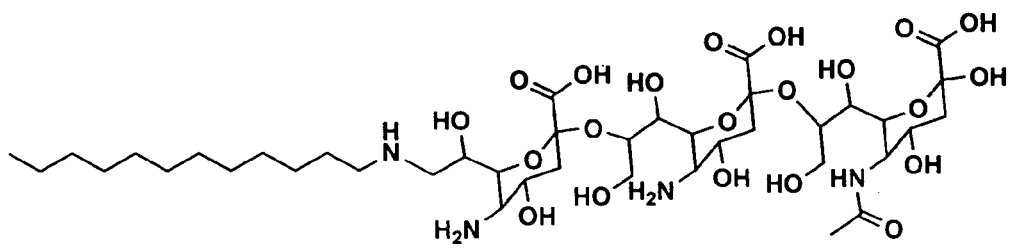
Figure 22:
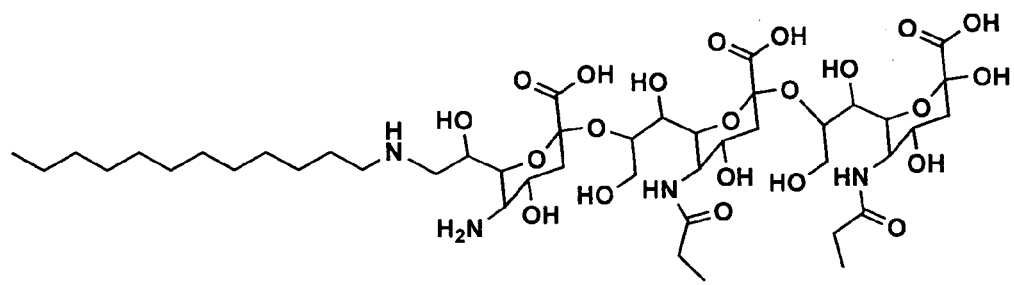
Figure 23:
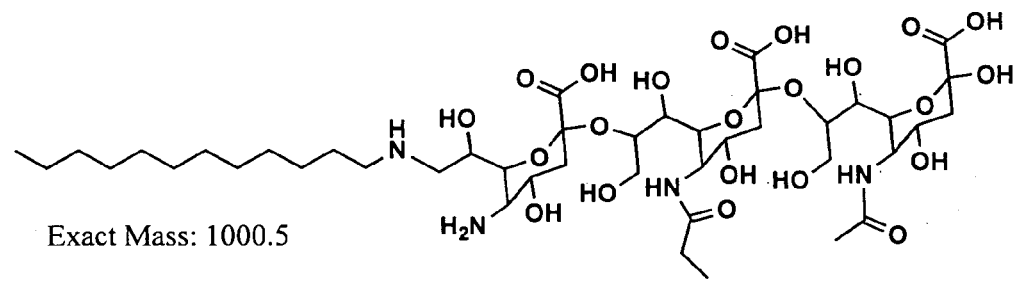
FIGS. 23-37 provide structures of exemplary acyl amine de-N-acetylated PS derivatives of the invention.
Figure 24:
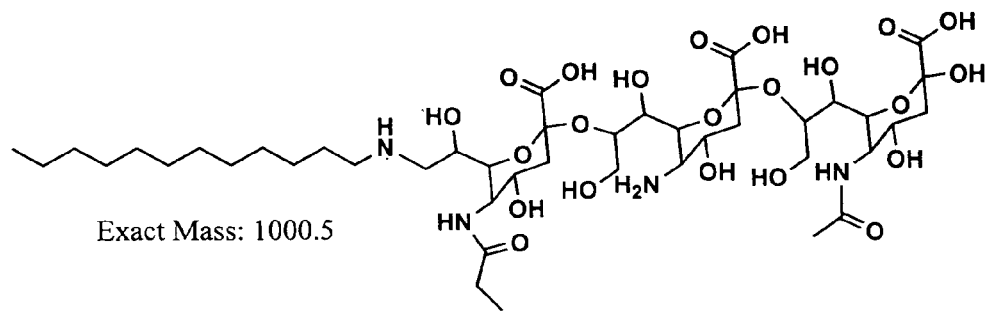
Figure 25:
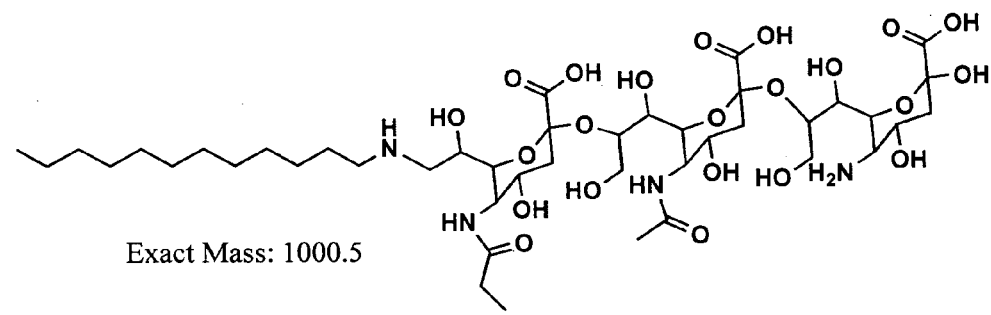
Figure 26:
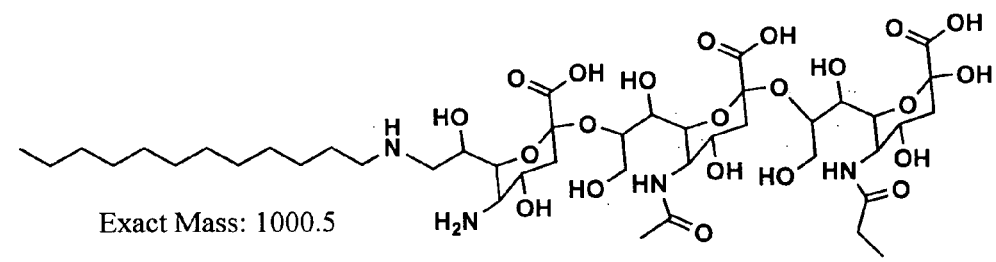
Figure 27:
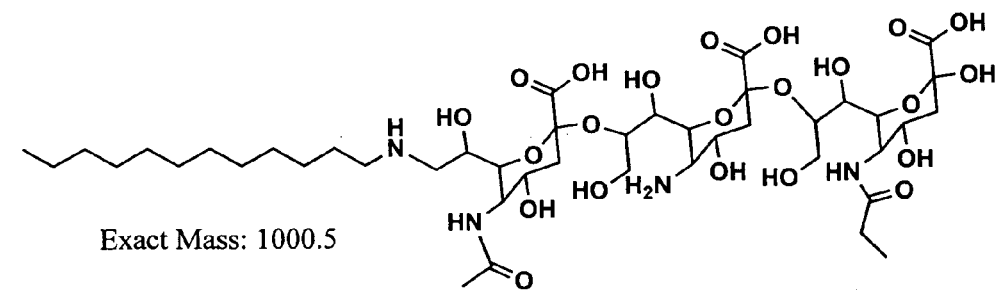
Figure 28:
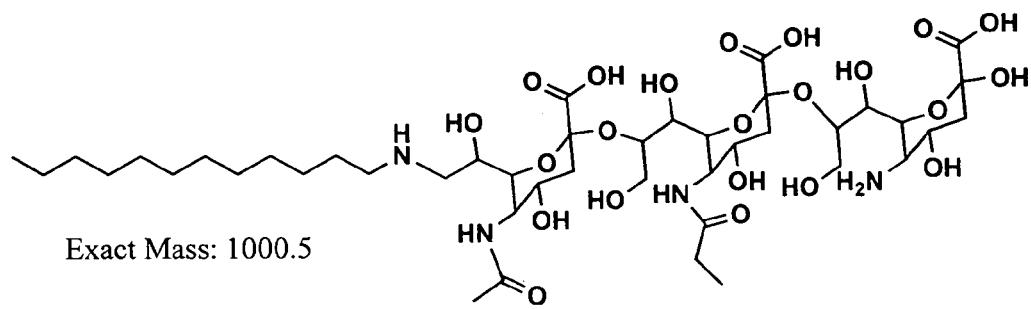
Figure 29:
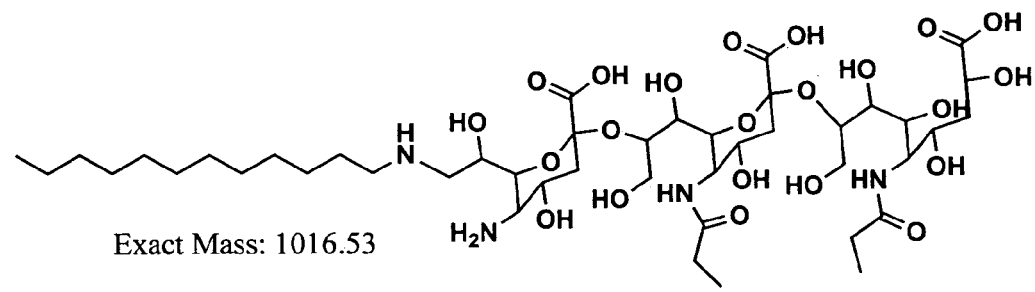
Figure 30:
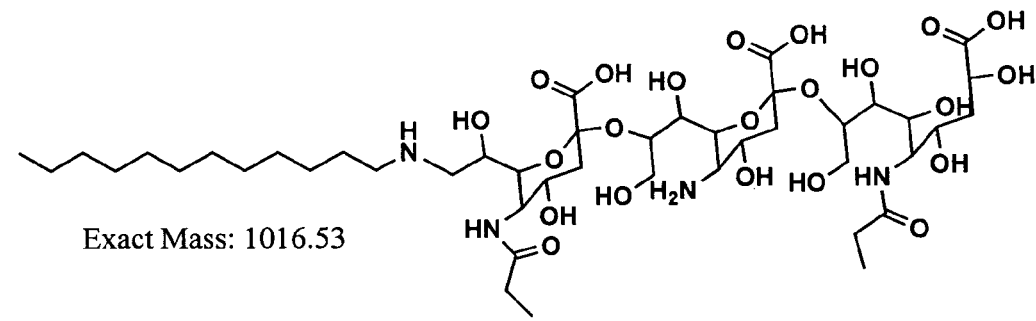
Figure 31:
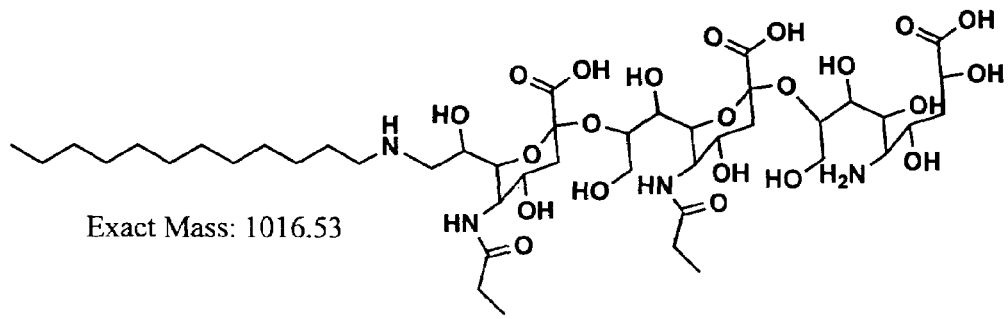
Figure 32:
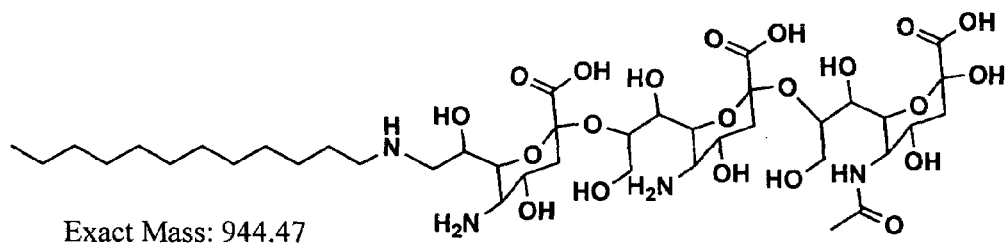
Figure 33:
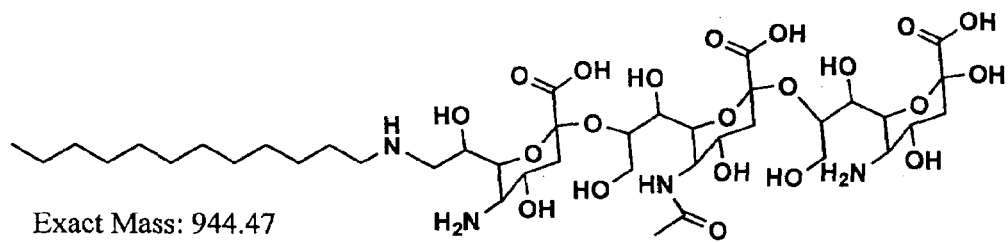
Figure 34:
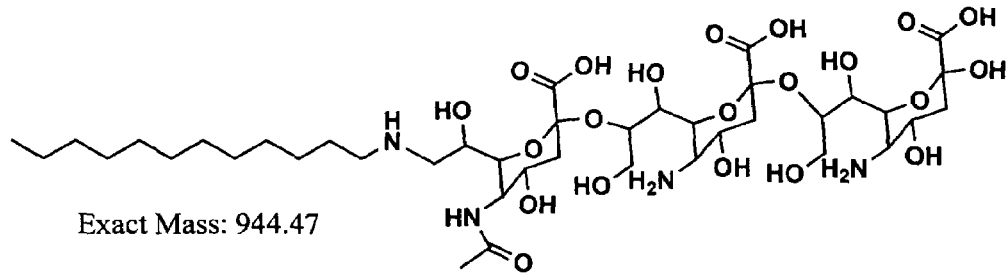
Figure 35:
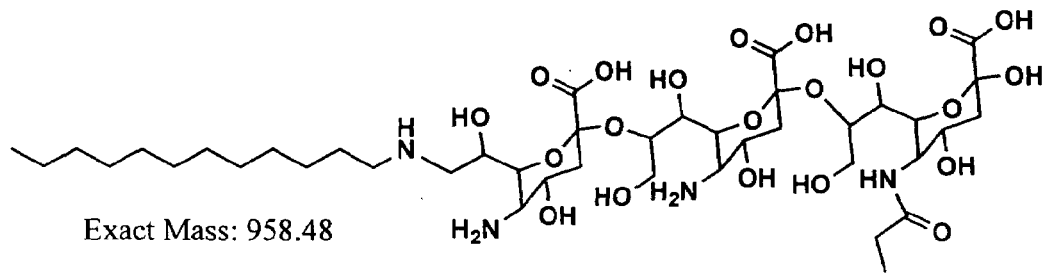
Figure 36:
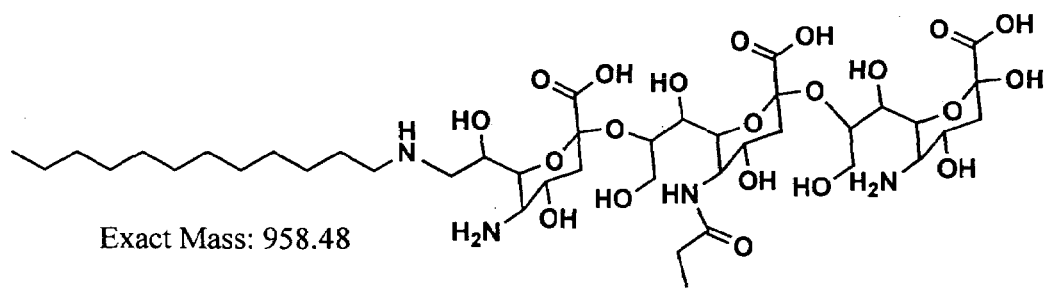
Figure 37:
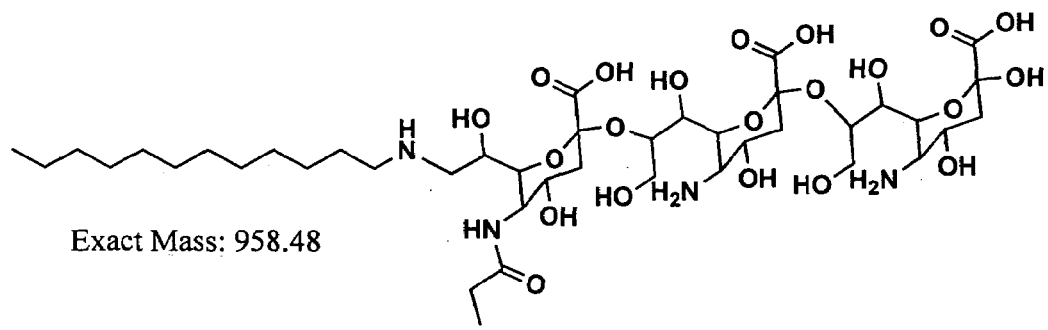

MALDI-TOF mass spectroscopy of non-reducing end dodecylamine derivatives of NmB PS. The solvent in fractions obtained from reverse-phase HPLC were evaporated using a SpinVac (ThermoSavant). The residue was dissolved in acetonitrile/water (1:1). A matrix of trihydroxyacetophenone (THAP) at a concentration of 3 milligrams per milliliter in acetonitrile/water was spotted onto the target (0.5 microliter per spot). After drying the matrix spots under vacuum, the sample was spotted on top of the matrix spot (0.5 microliters). MALDI-TOF (Autoflex, Bruker Daltonics) was performed in the both positive and negative linear modes (30 shots $N_2$ laser, 50% laser power) and in reflector positive and negative modes (30 shots $N_2$ laser, 50% laser power). The mass spectra were calibrated using external peptide (Bruker Daltonics) and sialic acid (EY Scientific) standards. The error of the observed masses were estimated to be $\leq$0.1%. FIGS. 20-22 show structures identified by MALDI-TOF from a preparation of NmB PS that were reactive with protective, non-autoreactive anti-NmB capsular mAb SEAM 3 and purified by reverse-phase HPLC as described above. The derivatives contain a mixture of de-N-acetyl, N-acetyl, and N-propionyl residues with at least one de-N-acetyl residue.

Example 2

Inhibition of Binding of Non-Autoreactive NmB Capsular mAbS to N-PR NmB PS in Elisa by Intermediates in the Synthesis of N-Acyl NmB PS Polysaccharide-protein conjugate vaccines prepared from NmB PS in which the N-acetyl groups of NmB PS have been replaced with propionyl groups (N-Pr NmB PS) elicit serum bactericidal antibodies in mice (patents cited) and non-human primates (Fusco), and a subset of these antibodies have minimal autoreactivity (patents cited). The reasons why anti-N-Pr NmB PS antibodies that do not react with human PS were bactericidal against NmB strains was unknown. In this example, we show that intermediates in the synthesis of N-acyl NmB PS inhibit binding of non-autoreactive anti-NmB capsular mAbs in ELISA. The inhibition solid phase ELISA was performed as follows.

Microtiter plates (Immulon 2; Dynatech Laboratories, Inc.,) containing 100 μl/well of avidin (4 μg/ml; ExtrAvidin; Sigma-Aldrich) in phosphate buffered saline (PBS; pH 7.4) were incubated overnight at 4° C. After washing three times with PBS, 100 μl of biotinylated N-Pr MenB PS diluted 1:800 in PBS, was added to each well and incubated at 37° C. for 2 h. The plates were then washed three times with PBS and the wells were filled with 250 μl of blocking buffer (PBS containing 1% bovine serum albumin [BSA] and 0.1% sodium azide; [pH 7.4]) and then incubated for 30-60 min at room temperature to block nonspecific binding sites. The plates were washed three times with washing buffer (PBS-0.1% Tween 20-0.1% sodium azide; [pH 7.40]). The non-autoreactive anti-NmB capsular monoclonal antibodies were prediluted to concentrations to yield an OD of 0.5 to 1.0 after approximately 30 minutes incubation with substrate. The monoclonal antibodies were added to wells of replica plates, each containing a final inhibitor concentration of 100 μg/ml of high molecular weight N-PrNmB PS, or PS derivative, or buffer alone. The plates were covered and incubated overnight at 4 degrees C. On the following day the wells were washed five times with washing buffer and were incubated for 3 h at 4° C. with 100 µl/well of alkaline phosphatase-conjugated anti-mouse polyclonal antibody (IgA+IgG+IgM; Zymed) diluted 1:2000 in diluting buffer. The plates were then washed with washing buffer, and 100 µl of freshly prepared substrate (p-Nitrophenyl phosphate; Sigma) diluted to 1 mg/ml in substrate buffer (1.0 M diethanolamine, 0.5 mM $MgCl_2$ [pH 9.8]) was added to each well. Absorbance values at 405 nm were measured at approximately 30 min. Percent inhibition was calculated by comparing absorbance values at 405 mm after 30 minutes incubation with substrate in wells that contained the inhibitor and the corresponding wells without inhibitor.

The following NmB PS derivatives were tested for inhibitory activity: Deacetylated NmB PS (deAc NmB PS), resynthesized N-acetyl NmB PS(N-Ac NmB PS), N-propionyl NmB PS(N-Pr NmB PS), periodate oxidized N-Ac NmB PS and N-Pr NmB PS (Ox N-Ac NmB PS and Ox N-Pr NmB PS, respectively), and NmB PS derivatives that were treated with acid to decrease the average Dp ($H^+$N-Ac NmB PS, $H^+$Ox N-Ac NmB PS, $H^+$N-Pr NmB PS, $H^+$Ox N-Pr NmB PS). In addition, as negative controls, NmB PS isolated from *N. meningitidis* group B strain MC58 and colominic acid from isolated from *E. coli* K1 (Sigma-Aldrich) were also tested. NmB PS was isolated as described by Constantino et al. (1999 Vaccine 17:1251). To eliminate the possibility of de-N-acetylated NmB PS resulting from hydrolysis occurring during isolation, NmB PS from *N. meningitidis* was treated with an excess of acetic anhydride in 0.1 M NaOH as described above and was incubated for 1 hr at pH 11 after acetylation to remove O-acetyl groups.

Figure 3:
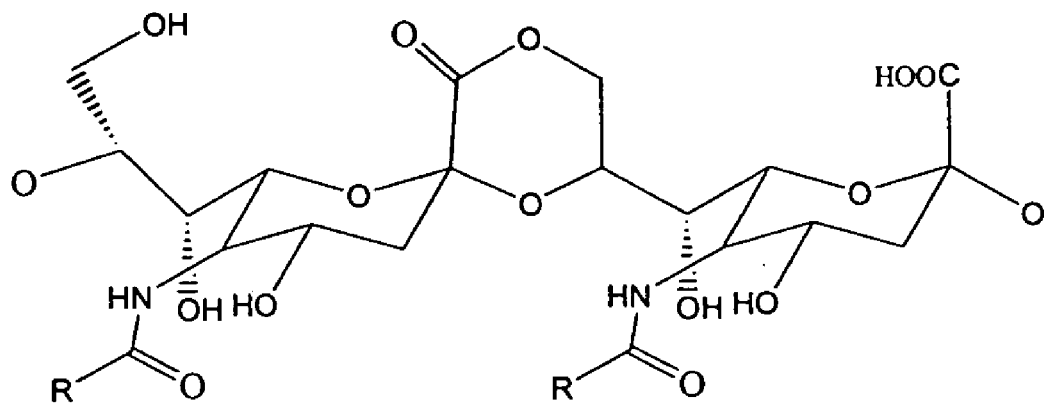
FIG. 3 provides the structure of a lactone moiety formed between the C1 carboxyl group and the C9 hydroxyl group of the preceding residue in NmB PS following acid treatment of NmB PS.
Figure 4:
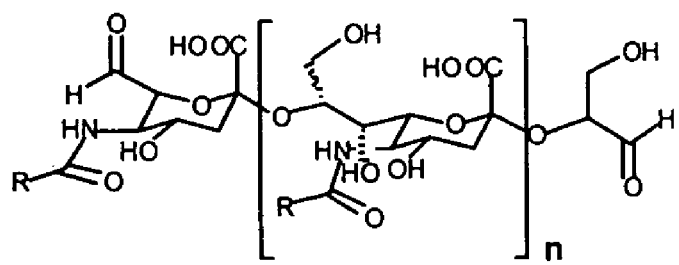
FIG. 4 provides the structure of a PS derivative having an aldehyde group at the non-reducing end terminal residue.
Figure 7:
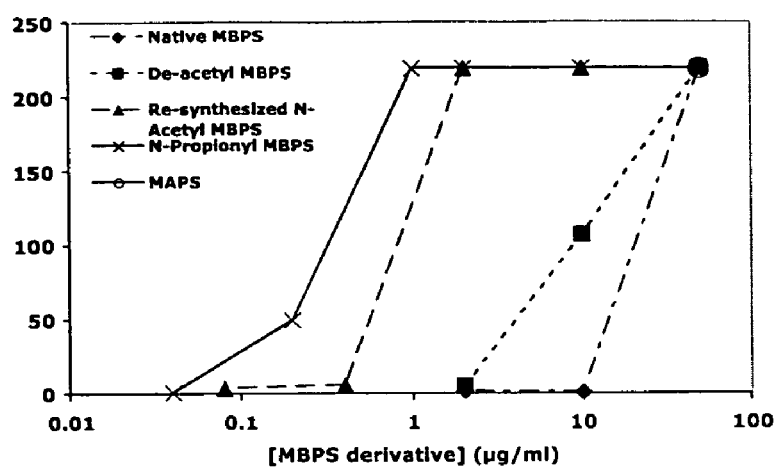
FIG. 7 is a graph showing inhibition of complement-mediated bactericidal activity data for SEAM 3 mAb in the presence of various NmB PS derivatives.

As shown in FIG. 5, N-Pr NmB PS was the best inhibitor of all four SEAM mAbs while colominic acid or NmB PS did not inhibit binding of any of the mAbs. In control experiments, the same solution of colominic acid or NmB PS completely inhibited binding of the anti-NmB PS mAb 2-1-B (class IgM, (Mandrell et al. 1982 J Immunol 129:2172) to N-Ac NmB PS or N-Pr NmB PS in ELISA at inhibitor concentrations less than 0.1 µg/ml. These results were expected since the SEAM mAbs were selected for the ability to bind to N-Pr NmB PS in ELISA, for the binding to be inhibited by soluble N-Pr NmB PS but to not bind to NmB PS (as a adipic dihydrazide derivative) as the surface antigen in ELISA. However, colominic acid does become an inhibitor of SEAM 3 and SEAM 12 after simple deacetylation and of SEAM 12 after re-acetylation. In contrast, acid treatment, which can result in lactone formation (FIG. 3), and oxidation of both N-Ac and N-Pr derivatives (FIG. 4) results in poorer inhibitors than the corresponding unmodified polysaccharides. The results show that the mAbs recognize an epitope that, at least in part, contains a de-N-acylated residue. Further, since the inhibitory concentrations for all derivatives increases after oxidation, it is likely that the epitope recognized by the mAbs is at the non-reducing and/or reducing ends of the polysaccharide which were modified by periodate treatment (FIG. 4).

Example 3

Inhibition of Complement Mediated Bactericidal Activity of Anti-N-PR NmB PS mAbs as Measured Against *N. Meningitidis* Group B Strain 8047.

This example demonstrates that the bactericidal activity of SEAM antibodies can be blocked by PS-derivatives containing de-N-acetyl residues and, thus, demonstrating that de-N-acetyl residues were present in the capsular PS of live NmB bacteria and the antigenic target of protective antibodies.

Complement-mediated bactericidal activity was measured with *N. meningitidis* group B strain 8047 as follows. After overnight growth on chocolate agar, several colonies of *N. meningitidis* were inoculated into in Mueller-Hinton broth (starting $A_{620nm}$ of ~0.1) and the test organism was grown for approximately 2 hrs to an $A_{620nm}$ of 0.6. After washing the bacteria twice in Gey's buffer containing 1% bovine serum albumin (BSA; RIA grade, Sigma-Aldrich), approximately 300 to 400 CFU were added to the reaction mixture. The assays were performed with rabbit complement (pooled infant rabbit serum obtained from Cedarlane, Hornby, Ontario, Canada). The final reaction mixture of 40 μL contained 20% (v/v) complement, mAbs diluted in Gey's 1% BSA buffer with or without inhibitor. CFU/ml in the reaction mixtures were determined after overnight growth on chocolate agar (Remel, Rancho Cordova, Calif.). Bactericidal titers or concentrations were defined as the serum dilution (or antibody concentration) resulting in a 50% decrease in colony forming units (CFU) per mL after 60 minutes incubation of bacteria in the reaction mixture, compared to the control CFU per mL at time 0. Typically, bacteria incubated with the negative control antibody and complement showed a 150 to 200% increase in CFU/mL during the 60 minutes of incubation.

As describe in Example 2, binding of anti-N-Pr NmB PS mAb SEAM 3 to solid phase N-Pr NmB PS in an ELISA was inhibited by soluble de-acetyl colomninic acid or re-N-acetyl NmB PS. FIG. 6 shows the ability of these intermediates to inhibit bactericidal activity of all the anti-N-Pr NmB PS mAbs as measured against *N. meningitidis* group B strain 8047. FIG. 7 shows the inhibition data for SEAM 3. The re-N-acetylated NmB PS was nearly as good an inhibitor of SEAM 3 bactericidal activity as N-Pr NmB PS (0.6 μg/ml compared to 0.2 μg/ml) whereas 7-fold higher concentrations of de-N-Ac NmB PS were required for inhibition and >20-fold higher concentrations of NmB PS. Thus, the capsular epitope recognized by the SEAM 3, a bactericidal non-autoreactive anti-N-Pr NmB PS mAb, was present in intermediates produced during the synthesis of the N-Pr NmB PS derivative that do not contain a propionyl group. Only native NmB PS inhibited the bactericidal activity of the anti-NmB PS mAb, 2-1-B and only N-Pr NmB PS inhibited bactericidal activity of SEAM 2 (FIG. 6). As a further control for specificity, 50 μg/ml of meningococcal A capsular polysaccharide did not inhibit the bactericidal activity of any of the mAbs tested.

Example 4

Determination of the Structure of NmB PS Derivatives Recognized by Protective, Non-Autoreactive Anti-NmB Capsular Monoclonal Antibodies by MALDI-TOF Mass Spectroscopy The protective, non-autoreactive anti-NmB capsular monoclonal antibodies (FIG. 2) were linked to magnetic beads as follows. MagnaBind™ goat anti-mouse IgG beads (20 μl; Pierce) were combined with 5 μg of SEAM 2, SEAM 3, SEAM 12, or SEAM 18 in PBS buffer. The mixture was incubated at ambient temperature on a rotating wheel for 1 hr. The beads were washed 3 times with wash buffer (see Example 2, above). The bound antibody was cross-linked to the beads by adding $BS^3$™(Pierce) to a concentration of 2 mM in PBS buffer and mixing by vortex for 30 min at ambient temperature. Unreacted was degraded by adding Tris to 0.1 M, pH 8.0 for 10 min. The beads were washed 3 times with PBS buffer. N-Pr NmB PS (240 micrograms) prepared in Example 1 was added to the washed beads in PBS buffer. After incubating the mixture on a rotating wheel for 1 h at ambient temperature, the unbound material was removed and the beads washed 2 times with wash buffer and once with PBS buffer then resuspended in 200 μl of PBS buffer. Neuraminidase (0.00175 U, EC3.2.1.18; Sigma) was added to each tube and the mixture incubated overnight at 37 degrees C. on a rotating wheel. The bound PS is heterogeneous with respect to Dp, therefore, the bead-antibody-PS complex was treated with neuraminidase, which sequentially removes residues from the non-reducing end of the polymer, to reduce the size of the polymer to the length that can be protected from further digestion by the antibody. After the neuraminidase treatment, the beads were washed 3 times with 50 mM ammoium carbonate buffer, pH 8.5 and the bound PS was finally eluted with 0.1 M triethylamine in water.

For analysis by matrix assisted laser desorption ionization time of flight (MALDI-TOF) mass spectroscopy, the solution of eluted PS and triethylamine/water was removed by evaporation in a Spin-Vac (Savant). Dried sample was resuspended in 4 µl of 50% (vol/vol) acetonitrile/water. The matrix, a saturated solution of 2',4',6'-trihydroxyacetophenone (THAP, Fluka Chemical) in 50% acetonitrile/water (0.5 µl), was spotted on a stainless steel target plate. PS sample (2 times, 0.5 µl) was spotted on top of the dried THAP spot. The samples were analyzed using a Bruker Autoflex MALDI-TOF mass spectrometer operating in the negative ion reflector mode.

Figure 8:
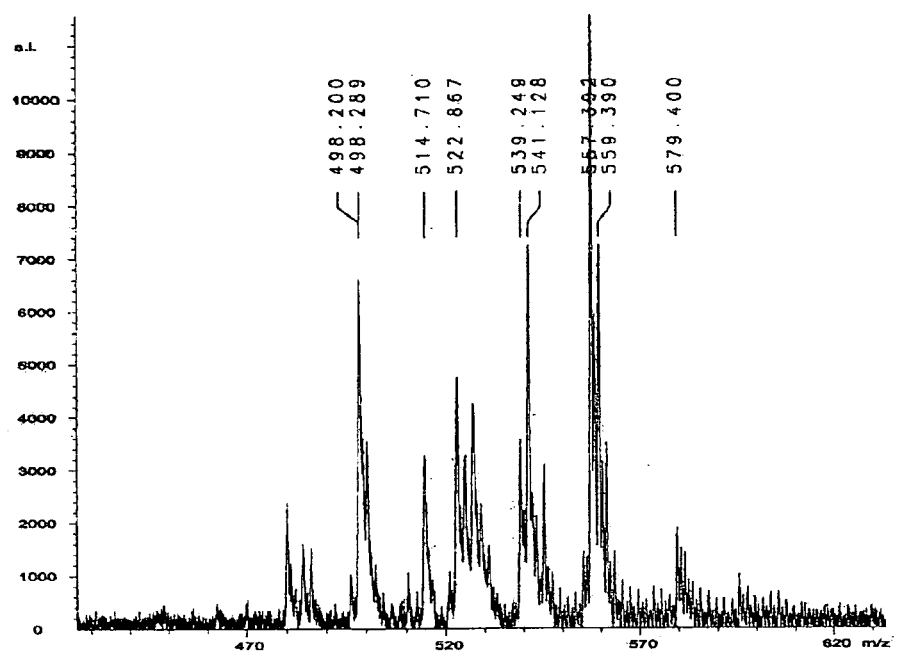
FIG. 8 shows the mass spectrum of PS derivatives selected and protected from neuraminidase cleavage by SEAM 3.
Figure 10:
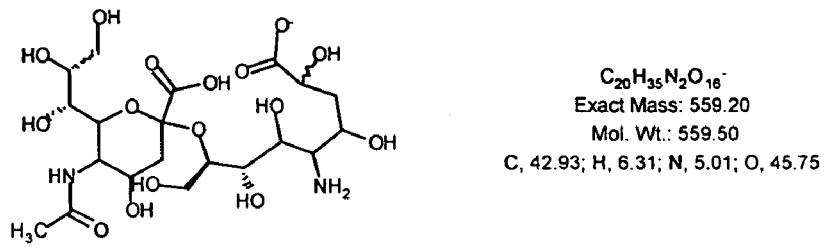
FIGS. 10-19 provide structures of de-N-acetylated PS derivatives identified in FIG. 9.

FIG. 8 shows a representative mass spectrum of PS derivatives bound by SEAM 3 after neuraminidase treatment. FIG. 9 shows the observed masses for each sample and the theoretical masses of corresponding ions that are consistent with the observed masses. The structures of PS derivatives are shown in FIGS. 10 to 19. All of the masses correspond to a disaccharide containing one or more residues in which the N-acetyl group on the C-5 amino group has been removed. Also, disaccharides containing one de-N-acetylated residue contain an N-acetyl group in the second sialic acid residue but not a N-propionyl group. Further, since the exosialidase removes residues processively from the non-reducing end, all of the derivatives bound by the SEAM mAbs and detected by MALDI-TOF are reducing end derivatives. This does not preclude the possibility that similar de-N-acetylated derivatives may also occur at the non-reducing end or interior residues of the polysaccharide as such derivatives would be difficult to detect since the polysaccharide is heterogeneous with respect to Dp.

In summary, the results of the inhibition ELISA for intermediates in the synthesis of N-Pr NmB PS and derivatives of N-Pr NmB PS captured by the SEAM mAbs and identified by MALDI-TOF mass spectroscopy show that the minimal determinant recognized by non-autoreactive, bactericidal anti-NmB group B capsular mAbs is a disaccharide containing one or two de-N-acetylated residues.

Example 5

Preparation of De-N-Acetylated PS Derivatives Using Organic Solvent/Water Suspension of PS and Acylating Agent Preparation of NmB PS Derivatives with C5 Amino Groups Protected as Trichloroacetyl (or Trifluoroacetyl) Amides.

20 milligrams of de-N-acetyl colominic acid was dissolved in 4 milliliters of formamide deionized with AG 501-8× mixed bed resin (BioRad) and containing 2.5% (vol./vol.) water. An amount of sodium methoxide in methanol equal to the 1.1 mole amount of free amino groups was added followed by a mixture (1.2 mole equivalents total) of trichloroacetic anhydride (or ethyl trifluoroacetyl ester) and acetic anhydride (or other activated acyl group, for example, propionic anhydride, lauric N-hydroxysuccinimide ester and the like) where the amount of trihaloacylating reagent is equal to the fraction of de-N-acetyl groups desired in the final product (for example, 10%, 25%, 50%, and so on). The mixture was stirred for several minutes and the pH was adjusted to 8 (determined by spotting the mixture on pH paper) by adding additional sodium hydroxide or methoxide as needed. The reaction mixture was dialyzed in water, and lyophilized. The products can purified by size exclusion (see, e.g., Example 1) and/or ion exchange chromatography according to methods well known in the art. If it is desired, the trichloroacetyl (or trifluoroacetyl) groups were removed by adding sodium borohydride (or ammonium carbonate to a concentration of 0.1 M, pH 9 for trifluroacetyl protected amides) and stirring at ambient temperature for 1 hour before dialysis in water and lyophilization.

Preparation of Reacylated NmB PS Derivatives Containing a Non-Reducing End Aldehyde.

Sodium metaperiodate (1 milligram of periodate per 10 milligrams of polysaccharide) was added to a solution of re-N-acylated NmB PS in which all of the amino groups were in the form of trifluoroacetyl (obtained as described in Example 6) or trichloroacetyl (prepared as described above in Example 5) protected or other amide in 0.1 M sodium acetate buffer, pH 6.5. The reaction was performed in the dark for a period of 30 min to 1 hour and quenched by the addition of excess ethylene glycol in water. The reaction mixture was then dialyzed in water and lyophilized.

The products were then conjugated to a carrier protein (BSA) by reductive amination with sodium cyanoborohydride. The PS derivative containing a non-reducing end aldehyde group was combined with the carrier protein at a ratio of 2:1 in PBS buffer. Sodium cyanoborohydride (1 mg per mg of carrier protein) was added and the mixture stirred in the dark for 5 days, then dialyzed in PBS buffer (10-14 kDa cutoff membrane).

Example 6

Biosynthetic Incorporation of N-Trichloroacetyl (or Trifluoroacetyl) Protected Sialic Acid Residues Into NmB PS and Use of the Resulting Capsular PS to Prepare PS-Protein Conjugate Vaccines 0.5 millimole (108 milligrams) of mannosamine hydrochloride was dissolved in 10 milliliter of methanol containing 0.55 millimole of sodium methoxide and cooled to 4 degrees C. 0.6 millimole of trichloroacetic anhydride (or ethyl trifluoroacetate) was added and the mixture stirred for 2 hrs. The progress of the reaction was monitored by spotting the reaction mixture on a silica gel TLC plate, developing the plate with ethylacetate, methanol, water (5:2:1) and detecting the disappearance of mannosamine at the origin with iodine vapor. At the completion of the reaction, 1.5 milliequivalents of AG 501-8× mixed bed resin (BioRad) and 10 milliliters of water was added, the pH was adjusted to 7 by adding NaOH or HCl as needed and the mixture gently shaking for 1 hour. The solvent mixture and beads were separated and the solvent was removed by lyophilization. Further purification of the product, if necessary, was performed by silica gel chromatography using the same solvent system described for TLC. Solvent from the combined fractions containing the desired material was removed by evaporation. Finally, the dried product was resuspended in water and lyophilized.

The trihaloacetylated mannosamine was incorporated into NmB PS by inoculating colonies of NmB strain M7 grown overnight at 37 degrees C. in 5% carbon dioxide on a freshly streaked chocolate agar plate to an OD620 nm of 0.1 in Muller-Hinton broth supplemented with 5 millimolar N-acyl mannosamine For example, N-acetyl, -trichloroacetyl, -trifluoroacetyl mannosamine. Stain M7 contains a transposon the interrupts the gene encoding N-acetyl-D-glucosamine-6-phosphate 2 epimerase (J. Swartley, J. S. and Stephens, D. S., 1994, J. Bact. 176:1530; Swartley, J. S., Ahn, J. H., Liu, L-J, Kahler, C. M., and Stephens, D. S., 1996, J. Bact. 178:4052). As a result, the bacteria cannot synthesize capsule PS unless the growth media was supplemented with N-acetyl mannosamine. Therefore, the N-acyl content of the capsule PS synthesized in this system can be determined by the N-acyl or mixture of N-acyl mannosamine provided in the growth media. The bacteria were grown at 37 degrees C. to an OD620 nm of overnight).

Figure 40:
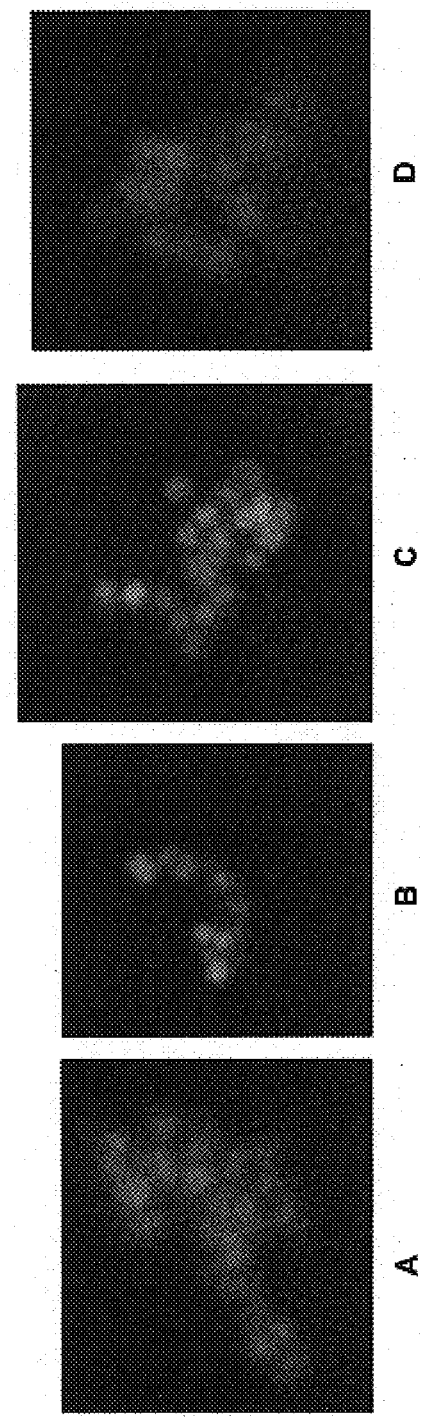
FIG. 40 is panel of photographs illustrating binding of SEAM 12 to NmB strain M7 in which the growth media was supplemented with N-acyl mannosamine derivatives as measured by fluorescence microscopy. Panel A: binding of SEAM 12 mAb to M7 supplemented with N-acetyl mannosamine; Panel B: binding of SEAM 12 to M7 without N-acyl mannosamine supplement; Panel C: binding of SEAM 12 mAb with N-trichloroacetyl mannosamine supplement; Panel D: binding of mAb SEAM 12 to the capsule PS containing N-trifluoroacetyl groups.

The production of capsule PS containing the trihalo acetyl groups was demonstrated by fluorescence microscopy using the mAb SEAM 12 to detect the presence of capsule PS on the M7 producing strain. The results are shown in FIG. 40. Binding of SEAM 12 to M7 supplemented with N-acetyl mannosamine is shown in FIG. 40 (Panel A) where binding is indicated by the presence of red fluorescence of the detecting, rhodamine-labeled secondary antibody (Zymed). The cells are labeled with the DNA stain SYTO (Molecular Probes, Inc.), which appears as green. There is no binding of SEAM 12 to M7 without N-acyl mannosamine or with N-trichloroacetyl mannosamine supplement (FIG. 40, Panels B,C). SEAM 12 does not bind to the capsule PS containing the trichloroacetyl groups because the large size of the trichloromethyl group disrupts binding. However, SEAM 12 does bind to the capsule PS containing N-trifluoroacetyl groups

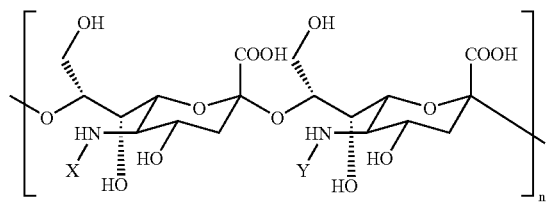

wherein

X and Y are independently H, an acetyl group, or an amine protecting group other than acetyl; and n is at least 1;

wherein the de-N-acetylated PS derivative is conjugated to a carrier protein or further comprises a sialic acid residue having an alkyl secondary amine at a non-reducing end of the de-N-acetylated PS derivative; and wherein the de-N-acetylated PS derivative comprises a minimum of about 20% N-acetyl sialic acid residues and at least one dimer comprising a de-N-acetyl sialic acid residue and an N-acetyl-sialic acid residue.

3. A composition comprising a polysaccharide (PS) derivative comprising a structure represented by the formula:

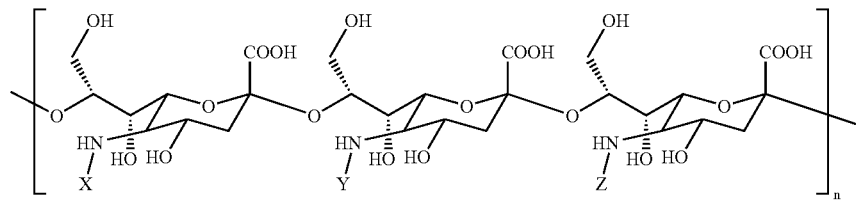

(FIG. 40, Panel D) since the trifluoromethyl group is nearly the same size as the methyl group of the N-acetyl derivative.

The polysaccharide was purified from the growth media as described by Guo and Jennings (Guo, Z. and Jennings, H. in 2001. In Meningococcal Vaccines: Methods and Protocols. A. J. Pollard, and C. J. M. Maiden, eds. Humana Press Inc., Totowa, N.J., p. 41). The purified polysaccharide was oxidized, conjugated to carrier proteins or fatty amines by reductive amination as described above, and the trihaloacetyl groups were removed by reduction with sodium borohydride. The final product was purified by size exclusion chromatography as described above, dialyzed in PBS, and lyophilized.

What is claimed is:

1. A composition comprising an adjuvant and a de-N-acetylated polysaccharide (PS) derivative, wherein the de-N-acetylated PS derivative is a polysialic acid heteropolymer comprising residues of N-acetyl sialic acid, de-N-acetyl sialic acid having a free amine, and re-N-acylated sialic acid having an amine protecting group other than acetyl, and wherein said heteropolymer further comprises a minimum of about 20% N-acetyl sialic acid residues and a least one dimer comprising an N-acetyl sialic acid residue and a de-N-acetyl sialic acid residue having a free amine.

2. A composition comprising a de-N-acetylated polysaccharide (PS) derivative comprising a heteropolymer of N-acetyl sialic acid, de-N-acetyl sialic acid having a free amine, and re-N-acylated sialic acid having an amine protecting group other than acetyl, and a structure represented by the formula:

wherein

X, Y and Z are independently H or a saturated acyl group, with the proviso that at least one of X, Y, and Z is H, at least one of X, Y, and Z is a saturated acyl group; and n is at least one; wherein the PS derivative is optionally conjugated to a carrier protein or further comprises a sialic acid residue having an alkyl secondary amine at a non-reducing end of the PS derivative, wherein said PS derivative further comprises a minimum of about 20% N-acetyl sialic acid residues and at least one dimer comprising an N-acetyl sialic acid residue and a de-N-acetyl sialic acid residue having a free amine.

4. The composition of claim 3, wherein when two of X, Y, and Z are acyl groups, the acyl groups are different acyl groups.

5. The composition of claim 4, wherein at least one of X, Y, and Z is an acetyl group and at least one of X, Y, and Z is a propionyl group.

6. The composition of claim 3, wherein when X is H, Y and Z are different acyl groups; when X is an acyl group, Y and Z are different moieties and are either H or a an acyl group; and when X is an acyl group, Y and Z are different moieties and are either H or an acyl group.

7. The composition of claim 6, wherein when X is H, Y and Z are different acyl groups selected from acetyl and propionyl;

when X is an acetyl group, Y and Z are different moieties and are either H or a propionyl group; and when X is a propionyl group, Y and Z are different moieties and are either H or an acetyl group.

8. The composition of claim 3, wherein the PS derivative comprises an amidated sialic acid residue having an alkyl secondary amine at a non-reducing terminus of the PS derivative.

9. The composition of any one of claims 1-2, wherein the de-N-acetylated PS derivative is conjugated to a carrier protein.

10. The compositions of any one of claims 1-3, wherein the PS derivative comprises a sialic acid residue derivative having a lactone moiety or a cyclic secondary amine.

11. A composition comprising a de-N-acetylated polysaccharide (PS) derivative comprising a heteropolymer of de-N-acetyl sialic acid residues, N-acetyl sialic acid residues, and re-N-acylated sialic acid residues having an amine protecting group other than acetyl, and a structure represented by the formula:

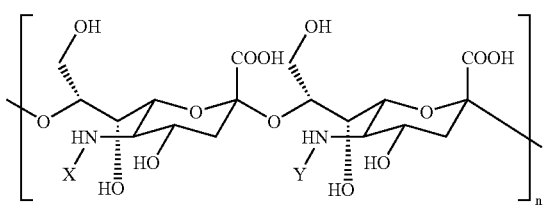

wherein
X and Y are independently an amine protecting group, or a saturated or unsaturated acyl group; and
n is at least 1;
wherein the de-N-acetylated PS derivative optionally further comprises a carrier protein conjugated to a sialic acid residue of the de-N-acetylated PS derivative, or optionally further comprises an amidated sialic acid residue having an alkyl secondary amine at a non-reducing end of the de-N-acetylated PS derivative; and
wherein the de-N-acetylated PS derivative comprises a minimum of about 20% N-acetyl sialic acid residues and at least one dimer comprising a de-N-acetyl sialic acid residue and an N-acetyl sialic acid residue.

12. The composition of claim 11, wherein the acyl group is a saturated acyl group selected from acetyl or propionyl.

13. The composition of claim 11, wherein the PS derivative comprises a structure represented by the formula:

wherein

X, Y and Z are independently an amine protecting group, with the proviso that at least one of X, Y, and Z is an amine protecting group and at least one of X, Y, and Z is a saturated or unsaturated acyl group; and n is at least one.

14. The composition of claim 13, wherein the acyl group is a saturated acyl group and acetyl or propionyl.

15. A method of immunizing a subject, comprising:
administering to a subject an amount of a PS derivative of claim 1 in an amount effective to elicit an immune response;

wherein said administering is effective to elicit an immune response in the subject against *Neisseria meningitidis* group B.

16. A method of immunizing a subject, comprising:
administering to a subject an amount of a PS derivative of claim 1 in an amount effective to elicit an immune response;

wherein said administering is effective to elicit an immune response in the subject against *Escherichia coli* K1.

17. A method for providing passive protection against a bacterial infection, the method comprising:
administering to a subject bactericidal antibodies elicited by immunization of a host with the de-N-acetylated PS derivative of any of claim 1;

wherein said administering provides for protection of the subject against *Neisseria meningitidis* group B or against *Escherichia coli* K1.

18. The composition of claim 1, wherein the PS derivative comprises a structure represented by the formula:

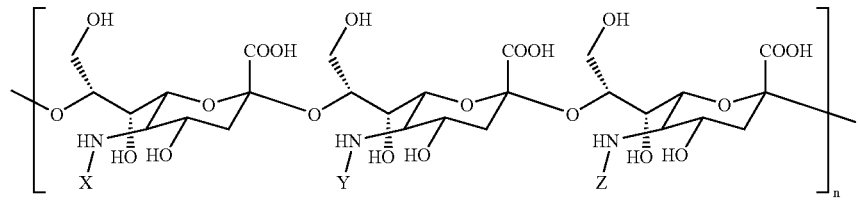

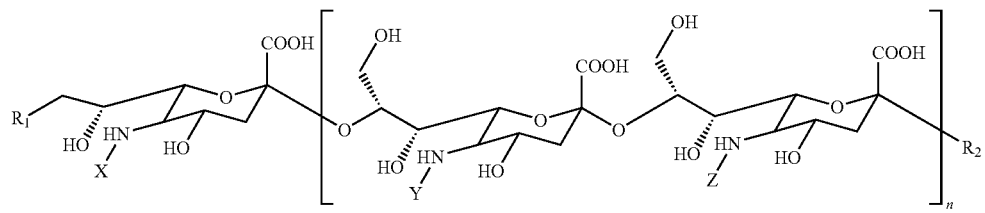

wherein X, Y and Z are independently H, or a saturated or unsaturated acyl group;
n is at least 1;
$R_1$ is a saturated or unsaturated acyl amine; and
$R_2$ is a hydroxyl, one or more acylated amines, a de-N-acetylated sialic acid residue, or a polymer of de-N-acetylated sialic acid residues and acylated sialic acid residues.

19. The composition of claim 18, wherein $R_2$ is polymer of a de-N-acetylated sialic acid residues and sialic acid residues; wherein said sialic acid residues are acetylated sialic acid residues, propionylated sialic acid residues or a combination thereof.

20. The composition of claim 1, wherein the PS derivative comprises a structure represented by the formula:

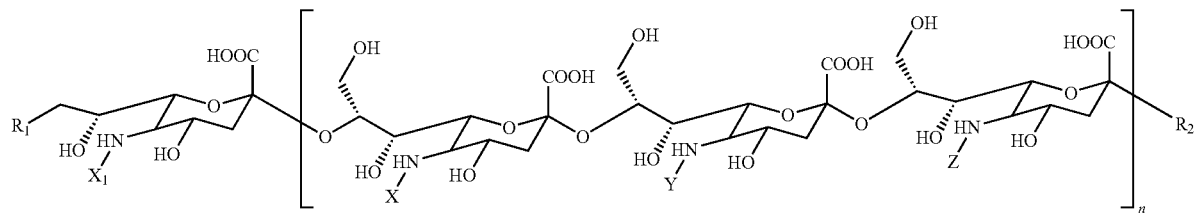

wherein $X_1$, X, Y and Z are independently H, or a saturated or unsaturated acyl group;
n is at least 1;
$R_1$ is a saturated or unsaturated acyl amine; and
$R_2$ is a hydroxyl, one or more acylated amines, a de-N-acetylated sialic acid residue, or polymer of de-N-acetylated sialic acid residues and acylated sialic acid residues.

21. The composition of claim 20, wherein $R_2$ is polymer of a de-N-acetylated sialic acid residues and sialic acid residues; wherein said sialic acid residues are acetlylated sialic acid residues, propionylated sialic acid residues or a combination thereof.

22. The composition of claim 18 wherein:

when X is H, Y and Z are different acyl groups selected from acetyl and propionyl;

when X is an acetyl group, Y and Z are different moieties and are either H or a propionyl group; and when X is a propionyl group, Y and Z are different moieties and are either H or an acetyl group.

23. A composition comprising an adjuvant and a de-N-acetylated polysaccharide (PS) derivative, wherein the de-N-acetylated PS derivative comprises residues of N-acetyl sialic acid and de-N-acetyl sialic acid having a free amine, a minimum of about 20% N-acetyl sialic acid residues, and a least one dimer comprising a N-acetyl sialic acid residue and a de-N-acetyl sialic acid residue having a free amine; and
wherein the de-N-acetylated PS derivative comprises a structure represented by the formula:

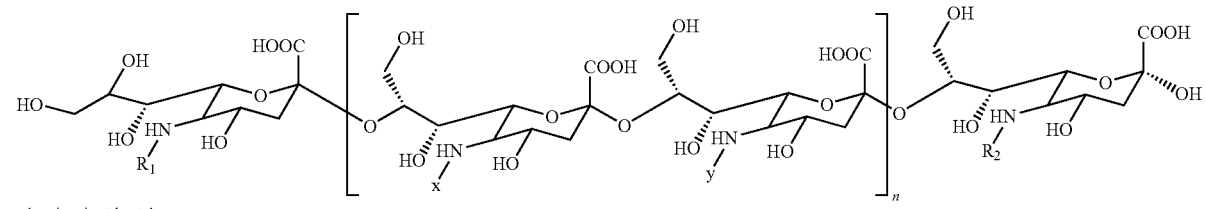

wherein n is at least 1;

wherein n is at least 1;
X and Y are independently H, or a saturated or unsaturated acyl group;
$R_1$ and $R_2$ are independently H, or a saturated or unsaturated acyl group; and wherein the de-N-acetylated PS derivative is further modified to include a carrier protein and/or an acyl amine.

24. The composition of claim 23, wherein n is at least 2, X is an acetyl group, Y is an acetyl group, $R_1$ is H, and $R_2$ is an acetyl group.

25. The composition of claim 24, wherein the de-N-acetylated PS derivative is further modified to include a carrier protein.

26. A composition comprising an adjuvant and a de-N-acetylated polysaccharide (PS) derivative conjugated to a carrier protein, wherein the de-N-acetylated PS derivative is a polysialic acid heteropolymer that comprises residues of N-acetyl sialic acid and de-N-acetyl sialic acid having a free amine, a minimum of about 20% N-acetyl sialic acid residues, and a least one dimer comprising an N-acetyl sialic acid residue and a de-N-acetyl sialic acid residue having a free amine.

27. The composition of claim 26, wherein the carrier protein is conjugated to the non-reducing end of the de-N-acetylated PS derivative.

28. The composition of claim 26, wherein the dimer comprising an N-acetyl sialic acid residue and a de-N-acetyl sialic acid residue having a free amine is at the non-reducing end of the de-N-acetylated PS derivative.

29. The composition of claim 26, wherein the de-N-acetylated PS derivative comprises a re-N-acylated sialic acid residue having an amine protecting group other than acetyl.

30. The composition of claim 26, wherein the de-N-acetylated PS derivative has degree of polymerization of about 2 to about 60.

31. The composition of claim 26, wherein the de-N-acetylated PS derivative has degree of polymerization of about 2 to about 10.

32. The composition of claim 1, wherein said de-N-acetylated PS derivative comprises an epitope recognized by the antibody SEAM 3.

33. The composition of claim 2, wherein said de-N-acetylated PS derivative comprises an epitope recognized by the antibody SEAM 3.

34. The composition of claim 11, wherein said de-N-acetylated PS derivative comprises an epitope recognized by the antibody SEAM 3.

35. The composition of claim 23, wherein said de-N-acetylated PS derivative comprises an epitope recognized by the antibody SEAM 3.

36. The composition of claim 26, wherein said de-N-acetylated PS derivative comprises an epitope recognized by the antibody SEAM 3.

* * * * *

UNITED STATES PATENT AND TRADEMARK OFFICE
CERTIFICATE OF CORRECTION

| | | |
|---|---|---|
| PATENT NO. | : 7,595,307 B2 | Page 1 of 1 |
| APPLICATION NO. | : 11/166781 | |
| DATED | : September 29, 2009 | |
| INVENTOR(S) | : Gregory R. Moe and Dan M. Granoff | |

It is certified that error appears in the above-identified patent and that said Letters Patent is hereby corrected as shown below:

On the cover page,

[*] Notice:    Subject to any disclaimer, the term of this patent is extended or adjusted under 35 USC 154(b) by 239 days Delete the phrase "by 239 days" and insert -- by 341 days --.

Column 50, lines 58 to 59, cancel the text reading "when X is an acyl group, Y and Z are different moieties and are either H or an acyl group;".

Column 53, line 65, "acetlylated" should read "acetylated".

Column 54, lines 48 to 62, cancel the subscript under the chemical formula reading "wherein n is at least 1;".

Signed and Sealed this

Twenty-fourth Day of August, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,595,307 B2 |
| APPLICATION NO. | : 11/166781 |
| DATED | : September 29, 2009 |
| INVENTOR(S) | : Gregory R. Moe |

Page 1 of 1

It is certified that error appears in the above-identified patent and that said Letters Patent is hereby corrected as shown below:

In the Specifications

In column 1, lines 15-19, please replace "This invention was made with government support under grants no. AI46464 and AI45642 awarded by the National Institute of Allergy and Infectious Diseases, and the National Institute of Health. The government may have certain rights in this invention" with -- This invention was made with government support under grant no. AI46464 awarded by the National Institute of Allergy and Infectious Diseases; and with government support under grant no. AI45642 awarded by the National Institute of Health. The government has certain rights in the invention--.

Signed and Sealed this
Sixth Day of May, 2014

Michelle K. Lee
*Deputy Director of the United States Patent and Trademark Office*